(12) United States Patent
Gravel et al.

(10) Patent No.: US 7,105,539 B2
(45) Date of Patent: Sep. 12, 2006

(54) DERIVATIVES OF SUCCINIC AND GLUTARIC ACIDS AND ANALOGS THEREOF USEFUL AS INHIBITORS OF PHEX

(75) Inventors: Denis Gravel, St-Lambert (CA); Elaref S. Ratemi, St-Laurent (CA); Mostafa Hatam, Brossard (CA); Guy Boileau, Brossard (CA); Philippe Crine, Outremont (CA); Isabelle Lemire, Montreal (CA)

(73) Assignee: Enobia Pharma, Montreal (CA)

( * ) Notice: Subject to any disclaimer, the term of this patent is extended or adjusted under 35 U.S.C. 154(b) by 51 days.

(21) Appl. No.: 10/727,119

(22) Filed: Dec. 3, 2003

(65) Prior Publication Data

US 2004/0186301 A1  Sep. 23, 2004

Related U.S. Application Data

(60) Provisional application No. 60/430,382, filed on Dec. 3, 2002.

(51) Int. Cl.
*A61K 31/401* (2006.01)
*A61K 31/164* (2006.01)
*A61K 31/445* (2006.01)
*C07D 207/02* (2006.01)
*C07D 211/04* (2006.01)

(52) U.S. Cl. ............... 514/315; 514/408; 514/613; 546/184; 548/537; 564/152

(58) Field of Classification Search ............ 514/315, 514/408, 613; 546/184; 548/537; 564/152
See application file for complete search history.

(56) References Cited

U.S. PATENT DOCUMENTS

| 4,168,267 A | 9/1979 | Petrillo, Jr. |
| 4,337,201 A | 6/1982 | Petrillo, Jr. |
| 5,362,727 A | 11/1994 | Robl |
| 5,380,921 A | 1/1995 | Ishikawa et al. |

FOREIGN PATENT DOCUMENTS

| CA | WO 00/50580 | 6/2000 |
| EP | 0 254 032 | 1/1988 |
| EP | 0 412 595 | 2/1991 |
| EP | 0 566 157 | 10/1993 |
| FR | 2372804 | 6/1978 |
| FR | 2377374 | 8/1978 |
| WO | WO 97/05865 | 2/1997 |
| WO | WO 99/11606 | 3/1999 |
| WO | WO 00/5080 | 8/2000 |
| WO | WO 02/15918 | 2/2002 |
| WO | WO 02/092128 | 11/2002 |
| WO | WO 03/084997 | 10/2003 |

OTHER PUBLICATIONS

Ovens et al., J. Peptide Sci. (2000), vol. 6, No. 9, pp. 489-495 (Abstract).*
Boileau et al., "Characterization of PHEX endopeptidase catalytic activity: identification of parathyroid-hormone-related peptide$_{107-139}$ as a substrate and osteocalcin, PP$_i$ and phosphate as inhibitors," *Biochem. J.*, 355:707-713, 2001.
Chapman et al., "Inhibition of matrix metalloproteinases by N-carboxyalkyl peptides," *J. Medicinal Chemistry*, abstract, 36(26):4293-4301, 1993.
Elgazwy and Abdel-Sattar, "Facile synthesis of (R,R) and of (R,S) tricarballylic acid anhydride and imide derivatives," *Molecules*, abstract, 5(4):665-673, 2000.
Fourine-Zaluski et al., "Differential recognition of 'enkephalinase' and angiotensin-converting enzyme by new carboxyalkyl inhibitors," *Life Sciences*, 31:2947-2954, 1982.
Mimura et al., "A novel class of enkephalinase inhibitors containing a C-terminal sulfo group," *J. Med. Chem.*, 35:602-608, 1992.
Ovens et al., "Design and synthesis of acidic dipeptide hydroxamate inhibitors of procollagen C-proteinase," *J. Peptide Science*, abstract 6(9):489-495, 2000.
Rinnova et al., "An expedient method for the solid-phase synthesis of alpha-aminoalkyl phosphonopeptides," *Tetrahedron Lett*, abstract, 43(22):4103-4106, 2002.
Rowe, "The role of the phex gene (PEX) in families with X-linked hypophosphataemic rickets," *Curr. Opin Nephrol Hypertens*, 7:367-376, 1998.
Serval et al., "In vitro and in vivo inhibition of N-acetyl-L-aspartyl-L-glutamate catabolism by N-acylated L-glutamate analogs," *J. Pharmacology and Experimental Therapeutics*, abstract, 260(3):1093-1100, 1992.

(Continued)

*Primary Examiner*—Taofiq Solola
(74) *Attorney, Agent, or Firm*—Fulbright & Jaworski L.L.P.

(57) ABSTRACT

The present invention relates to derivatives of succinic and glutaric acids and analogues thereof, having the following general formula:

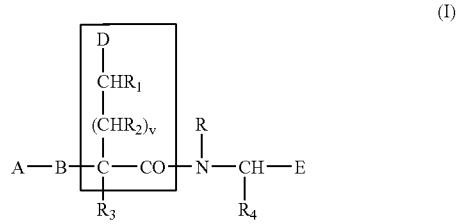

(I)

useful as inhibitors of PHEX. These derivatives are useful for promoting generation of bone mass and treating or preventing diseases or conditions associated with a phosphate metabolism defect. Methods for preparation and intermediates are also disclosed.

26 Claims, 5 Drawing Sheets

OTHER PUBLICATIONS

ADHR Consortium, Nat. Genetics, 26:345-348, 2000.
Atherton and Sheppard, In: The Peptides, Udenfriend and Meienhofer (Eds.), 9:1, Academic Press, NY, 1967.
Beck et al., J. Clin. Invest., 99:1200-1209, 1997.
Balkenhohl et al., Angew. Chem. Int. Ed. Engl., 35:2288-2337, 1996.
Bellows et al., Calcif. Tissue Int., 38:143-154, 1986.
Du et al., Genomics, 36:22-28, 1996.
Ecarot et al., J. Bone. Miner. Res., 7:215-220, 1992.
Econs and Drezner, N. Engl. J. Med., 330:1679-1681, 1994.
Furka. In: Combinatorial Peptide and Nonpeptide Libraries, Jung (Ed.), 4:111-137, VCH Vertagspasellschaft, Weinheim, 1996.
Greene and Wuts, In: Protective Groups in Organic Synthesis, John Wiley & Sons, Inc., NY, 1999.
Grieff et al., Biochem. Biophys. Res. Commun., 231:635-639, 1997.
Guo and Quarles, J. Bone Miner. Res., 12:1009-1017, 1997.
Hermkens et al., Tetrahedron, 52:4527-4554, 1996.
Ikeuchi et al., J. Biomed. Mater Res., 60:61-69, 2002.
Jan de Beur et al., J. Bone Miner. Res., 17:1102-1110, 2002.
Jonsson et al., ASBMR 24th Annual Meeting in San Antonio, Texas, USA, Pres. # 1139, 2002.
Lajeunesse et al., Kidney Int., 50:1531-1538, 1996.
Lipman et al., J. Biol. Chem., 273:13729-13737, 1998.
Nesbitt et al., J. Bone Miner. Res., 14:2027-2035, 1999.
Rivero et al., In:A Practical Guide to Combinatorial Chemistry, Czamik (Eds.), 10:281 307, American Chem. Soc. Pub., Washington DC, 1997.
Roques et al., Pharmacological Reviews, 45:87-146, 1993.
Rowe et al., Genomics, 67:54-68, 2000.
Ruchon et al., J. Histochem. Cytochem., 46:1-10, 1998.
Ruchon et al., J. Bone Miner. Res., 15:1440-1450, 2000.
Schiavi and Moe, Curr. Opin. Nephrol. Hypertens., 11:423-430, 2002.
Shimada et al., Proc. Natl. Acad. Sci. USA, 98:6500-6505, 2001.
Strom et al., Hum. Mol. Genet., 6:165-171, 1997.
Tenenhouse, Nephrol. Dial.. Transplant, 14:333-341, 1999.
Tenenhouse and Econs, In: The Metabolic and Molecular Bases of Inherited Disease. Scriver et al. (Eds.), 197:5039-5067, McGraw Hill Book Co., NY, 2001.
Terrett et al., Tetrahedron, 51:8135-8173, 1995.
The HYP Consortium, Hat. Genet., 11:130-136, 1995.
Thompson and Ellman, Chem. Rev., 96:555-600, 1996.
Turner and Tanzawa, FASEB J., 11:355-364, 1997.
Vehof et al., Plast. Reconstr. Surg., 108:434-443, 2001.
Vu et al., J. Histochem. Cytochem., 47:323-336, 1999.
Whittaker et al., Chem. Rev., 99:2735-2776, 1999.
Yoshida et al., J. Dent. Res., 78:217-220, 1999.

* cited by examiner

DERIVATIVES OF SUCCINIC AND GLUTARIC ACIDS AND ANALOGS THEREOF USEFUL AS INHIBITORS OF PHEX

This application claims the benefit of U.S. Provisional Application No. 60/430,382, filed Dec. 3, 2002. The entire text of the above provisional application is specifically incorporated by reference.

BACKGROUND OF THE INVENTION

A. Field of Invention

The present invention relates to derivatives of succinic and glutaric acids and analogs thereof, useful as inhibitors of PHEX. More specifically, the present invention relates to derivatives of succinic and glutaric acids and analogs thereof useful for promoting faster regeneration of bone mass after bone fractures, implantation of orthopedic and dental prostheses, or after loss of bone mass as a consequence of bone diseases such as osteoporosis.

B. Related Art

The PHEX gene (formerly PEX; Phosphate regulating gene with homologies to endopeptidases on the X chromosome) was identified by a positional cloning approach as the candidate gene for X-linked hypophosphatemia (XLH) (The Hyp Consortium, 1995). XLH is a Mendelian disorder of phosphate homeostasis characterized by growth retardation, rachitic and osteomalacic bone disease, hypophosphatemia, and renal defects in phosphate re-absorption and vitamin D metabolism (Tenenhouse and Econs, 2001).

Several groups have cloned and sequenced the human and mouse PHEX/Phex cDNAs (PHEX/Phex refers to the human and mouse genes, respectively) (Du et al., 1996; Lipman et al., 1998; Grieff et al., 1997; Beck et al., 1997; Guo and Quarles, 1997; Strom et al., 1997). Amino acid sequence comparisons have demonstrated homologies between PHEX/Phex protein and members of the neutral endopeptidase family, as previously observed in the partial sequence of the candidate PHEX gene (The HYP Consortium, 1995). The peptidases of the neutral endopeptidase family are zinc-containing type II integral membrane glycoproteins having a relatively short cytoplasmic N-terminal region, a single transmembrane domain, and a long extracytoplasmic domain containing the active site of the enzyme (Turner and Tanzawa, 1997).

Much of the present knowledge about XLH has been obtained from studies of the Hyp mouse, which harbours a large deletion of the Phex gene (Beck et al., 1997) and which has been used as an animal model of the human disease (Tenenhouse, 1999). In particular, these animals show increased renal phosphate excretion due to a down-regulation of the Npt2 phosphate transporter, which is necessary for the re-absorption of phosphate from the nephron. The serum concentration of $1,25(OH)_2D3$ (calcitriol) was found to be the same in Hyp mice as in normal littermates. However, the Hyp kidney showed an accelerated degradation of the vitamin D metabolite to $1,24,25(OH)_3D3$, a metabolite with reduced activities. In the presence of a phosphate rich diet, Hyp mice were shown to experience an increase in serum $1,25(OH)_2D3$ and a drop in C-24 oxidation products, in contrast to normal mice which experienced no such changes. The renal disorder in vitamin D metabolism in Hyp mice appears to be secondary to the phosphate disorder.

The mechanism by which loss of PHEX function elicits the observed bone and renal abnormalities in XLH patients is not clear. There are no data suggesting the presence of PHEX/Phex mRNA in the kidney (Du et al., 1996; Beck et al., 1997; Grieff et al., 1997). However, considering the similarities between the PHEX protein and the other members of this metallopeptidase family, it has been speculated that PHEX may regulate renal phosphate reabsorption by controlling the activity of a circulating factor. It was demonstrated that the inhibition of Na-dependent phosphate transport in cultured renal cells can be achieved by a factor in conditioned medium from cultured osteoblasts derived from Hyp mice (Lajeunesse et al. 1996; Nesbitt et al., 1999).

Phosphaturic activity(ies) have also been discovered in tumors from patients with tumor-induced osteomalacia (TIO, also known as oncogenic hypophosphatemic osteomalacia), an acquired renal phosphate wasting disorder with the phenotypic features of XLH (Tenenhouse and Econs, 2001). The term "phosphatonin" was designated to depict the phosphaturic tumor factor(s) (Econs and Drezner, 1994) and although the exact nature of "phosphatonin" remains to be determined, several candidates have been proposed (Schiavi and Moe, 2002). It has been shown that mutations in the FGF-23 gene which encodes a novel growth factor, fibroblast growth factor-23 (FGF-23), is responsible for Autosomal Dominant Hypophosphatemic Rickets (ADHR), an inherited disorder that resembles XLH and TIO (ADHR Consortium, 2001). Moreover, it has been demonstrated that overexpression of FGF-23 in animal models elicits renal phosphate wasting, a reduction in serum phosphate levels and osteomalacia (Shimada et al., 2001). Of interest are the findings that FGF-23 is overexpressed in tumors from patients with TIO (Jan de Beur et al., 2002) as well as in XLH patients (Jonsson et al., 2002). In addition to FGF-23, other proteins such as Frizzled-related protein 4 (FRP-4) (Jan de Beur et al., 2002) and MEPE (matrix extracellular phosphoglycoprotein) (Rowe et al., 2000) are overexpressed in TIO tumors.

PHEX/Phex mRNA has been detected in bones by Northern blot hybridization and in other adult and fetal tissues such as lungs, liver, muscles, and ovaries by RT-PCR and RNase protection assays (Du et al., 1996; Beck et al., 1997). In situ hybridization performed on sections of embryos and newborn mice showed the presence of Phex mRNA in osteoblasts and odontoblasts (Ruchon et al., 1998). Phex gene expression was detectable on day 15 of embryonic development, which coincides with the beginning of intracellular matrix deposition in bones. Moreover, Northern blotting analysis of total RNA from calvariae and from teeth of 3-day-old and adult mice showed that the abundance of the Phex transcript had decreased in adult bones and in non growing teeth. This result was confirmed when the presence of the Phex protein in newborn adult bones was investigated by Western blotting using a monoclonal antibody raised against the human PHEX. Immunohistochemical studies on a 2 month-old mouse showed exclusive labeling of mature osteoblasts and osteocytes in bones, and of odontoblasts in teeth (Ruchon et al., 2000). These results suggest that PHEX/Phex is important in both the development and maintenance of mineralization in these tissues. This hypothesis was supported by evidence of intrinsic abnormalities in osteoblasts from Hyp mice (Ecarot et al., 1992; Karaplis 2003). PHEX might thus be involved in the control of bone metabolism, both indirectly at the kidney level by controlling renal phosphate reabsorption, and directly at the bone level by inactivating a trophic peptide factor controlling either osteoblast or osteoclast functions or both.

Osteogenesis is a complex biological process that includes proliferation and differentiation of bone-forming cells (osteoblasts), synthesis of an organic matrix composed mainly of type I collagen, and mineralization of the organic matrix by deposition of hydroxyapatite crystals. Various technologies have been developed to stimulate osteogenesis for bone regeneration in osseous reconstructive surgery. These include the use of bone morphogenetic proteins (BMPs) as osteogenic agents, mostly in combination with a solid support such as metal meshes (Vehof et al., 2001), atelopeptide type I collagen (Ikeuchi et al., 2002) or hydroxyapatite (Yoshida et al., 1999). Hydroxyapatite is an osteoconductive material that maintains an original biocompatible form. During reconstruction of bone defects, its osteoconduction can be enhanced with osteogenic agents such as BMPs. More recently, evidence has emerged that novel and still poorly characterized peptides might also be useful for stimulating osteogenesis. These peptides are thought to be involved in poorly characterized pathways regulating bone mineralization. It is surmised that these pathways could be under the control of PHEX.

There thus remains a need to develop selective PHEX inhibitors to control phosphate metabolism and which can be used as osteogenic agents, as well as methods of administering the PHEX inhibitors.

The present invention seeks to meet these and other needs. The present description refers to a number of documents, the contents of which is herein incorporated by reference in their entirety.

SUMMARY OF THE INVENTION

There are many reports in the patent and scientific literature of compounds useful as inhibitors of zinc metallopeptidases. More specifically, the compounds of relevance in such reports are based on structures comprising a zinc ligand such as a thiolate, carboxylate, hydroxamate, phosphonate or phosphinate, linked directly or tethered to the N-terminal side of a dipeptide or analog thereof. An additional feature of these compounds is the characteristic presence of a hydrophobic side chain on the N-terminal amino acid or analog thereof bearing the zinc ligand. These compounds are useful mainly as ACE, NEP, ACE-NEP, ECE and MMP inhibitors (U.S. Pat. No. 4,337,201; U.S. Pat. No. 5,362,727; U.S. Pat. No. 5,380,921; Roques et al., 1993; Whittaker, et al., 1999). As disclosed in the present invention, it was discovered that when this N-terminal amino acid or analog thereof is characterized by a side chain bearing an ionizable acidic group at physiological pH, an entirely new class of zinc metallopeptidase inhibitors, more specifically zinc metallopeptidase inhibitors selective as PHEX inhibitors, can be delineated.

The present invention relates to derivatives of succinic and glutaric acids and analogs thereof useful as inhibitors of PHEX, as well as to methods of administering them.

More specifically, the present invention relates to succinic and glutaric acids and derivatives or analogs thereof, characterized by the presence of an ionizable acidic group (D) at physiological pH and by the presence of a zinc ligand or zinc ligand bearing moiety (A) linked via a linker (B) to the acid residue, its derivative or analog thereof. The compounds of the present invention can be illustrated by the general structure shown below in Formula I:

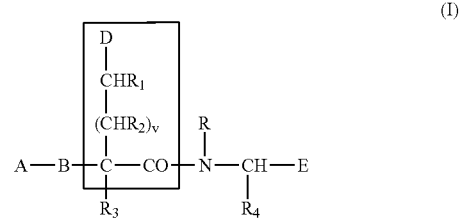

wherein:

A is a zinc ligand or zinc ligand bearing moiety selected from the group consisting of:

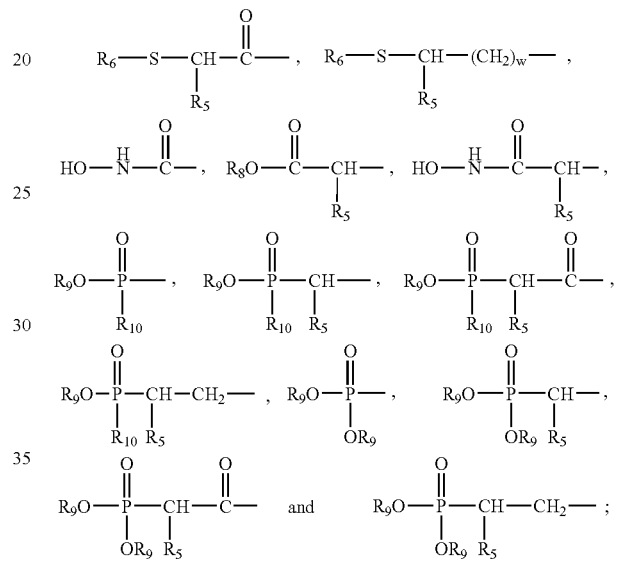

B is

or absent;

R is hydrogen or lower alkyl;

$R_1$ is hydrogen or lower alkyl;

$R_2$ is hydrogen, or lower alkyl;

$R_1$, when v=1, may be connected to the carbon bearing $R_2$ to form an alkylene bridge of 1 carbon atom, representing with the carbon atom to which it is attached a cyclopropane ring;

$R_2$, when v=1, may be connected to the carbon bearing $R_1$ to form an alkylene bridge of 1 carbon atom representing with the carbon atom to which it is attached a cyclopropane ring;

R3 is hydrogen or lower alkyl;

R1, when v=1, may be connected to the carbon bearing R3 to form an alkylene bridge of 1 carbon atom, representing with the carbon atom to which it is attached a cyclobutane ring;

R3, when v=1, may be connected to the carbon bearing R1 to form an alkylene bridge of 1 carbon atom, representing with the carbon atom to which it is attached a cyclobutane ring;

$R_1$ and $R_3$, when v=1, may be connected together to form an alkylene bridge of 2 carbon atoms representing with the carbon atoms to which they are attached a cyclopentane ring;

$R_1$ and $R_3$, when v=0, may be connected together to form an alkylene bridge of 3 carbon atoms representing with the carbon atoms to which they are attached a cyclopentane ring;

$R_1$ and $R_3$, when v=0, may be connected together to form an alkylene bridge of 4 carbon atoms representing with the carbon atoms to which they are attached a cyclohexane ring;

$R_1$ and $R_3$, when v=1, may be connected together to form an alkylene bridge of 3 carbon atoms representing with the carbon atoms to which they are attached a cyclohexane ring;

$R_4$ is lower alkyl, substituted lower alkyl, cycloalkyl-$(CH_2)_w$—, aryl-$(CH_2)_w$—, substituted aryl-$CH_2)_w$— or heteroaryl-$(CH_2)_w$—;

R and $R_4$ may be connected together to form an alkylene bridge of 3 carbon atoms representing with the nitrogen and carbon atoms to which they are attached a pyrrolidine ring;

R and $R_4$ may be connected together to form an alkylene bridge of 4 carbon atoms representing with the nitrogen and carbon atoms to which they are attached a piperidine ring;

$R_5$ is hydrogen, lower alkyl, substituted lower alkyl, cycloalkyl-$(CH_2)_x$—, aryl-$(CH_2)_x$—, substituted aryl-$(CH_2)_x$—, or heteroaryl-$(CH_2)_x$—;

$R_6$ is hydrogen, $R_7$—CO—, or $R_{12}$—S—;

$R_7$ is alkyl, substituted alkyl, cycloalkyl-$(CH_2)_y$, aryl-$(CH_2)_y$—, substituted aryl-$(CH_2)_y$— or heteroaryl-$(CH_2)_y$—;

$R_8$ and $R_9$ are independently selected from the group consisting of hydrogen, alkyl, substituted alkyl, aryl-$(CH_2)_y$—, substituted aryl-$(CH_2)_y$—, heteroaryl-$(CH_2)_y$—,

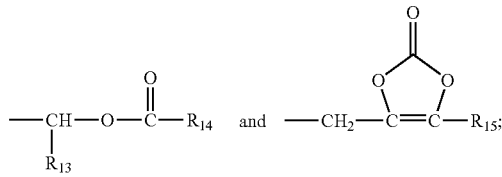

$R_{10}$ is alkyl, substituted alkyl, cycloalkyl-$(CH_2)_y$, aryl-$(CH_2)_y$—, substituted aryl-$(CH_2)_y$— or heteroaryl-$(CH_2)_y$—;

$R_{11}$ is hydrogen or lower alkyl;

the carbon bearing $R_1$ and the nitrogen bearing $R_{11}$, when v=1, may be directly connected together to form an azetidine ring;

$R_1$ and $R_{11}$, when v=0, may be connected together to form an alkylene bridge of 3 carbon atoms representing with the nitrogen and carbon atoms to which they are attached a piperidine ring;

$R_1$ and $R_{11}$, when v=1, may be connected together to form an alkylene bridge of 2 carbon atoms representing with the nitrogen and carbon atoms to which they are attached a piperidine ring;

$R_2$ and $R_{11}$, when v=1, may be connected together to form an alkylene bridge of 2 carbon atoms representing with the nitrogen and carbon atoms to which they are attached a pyrrolidine ring; the alkylene bridge may be substituted by a lower alkyl or alkenyl group at either carbon;

$R_{12}$ is alkyl, substituted alkyl, cycloalkyl-$(CH_2)_y$—, aryl-$(CH_2)_y$—, substituted aryl-$(CH_2)_y$—, heteroaryl-$(CH_2)_y$—,

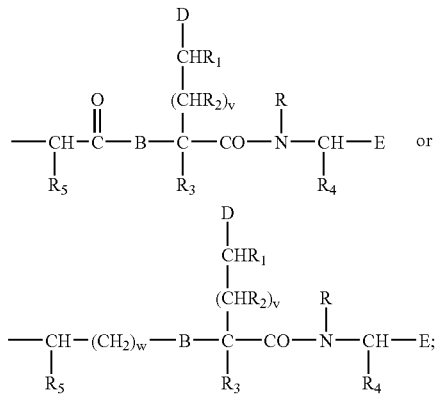

in which case —S—$R_{12}$ completes a symmetrical disulfide;

$R_{13}$ is hydrogen, lower alkyl, cycloalkyl or phenyl;

$R_{14}$ is hydrogen, lower alkyl, lower alkoxy or phenyl;

$R_{15}$ is lower alkyl or aryl-$(CH_2)_y$—;

D is —COOH, —$SO_2H$, —$SO_3H$, —$PO_3H_2$; —$OSO_3H$ or —$OPO_3H_2$;

E is hydrogen, $R_{12}$, —COOH, —$CONH_2$, —CONH (lower alkyl), —CON(lower alkyl)$_2$, —CONH—$(CH_2)_z$-aryl, —CON(—$(CH_2)_z$-aryl)$_2$, —CO-amino acid, —$CH_2$COOH, $CH_2$OH, —$CH_2CH_2$OH, or —COOR$_{16}$;

$R_{16}$ is as previously defined for $R_8$ and $R_9$;

C is carbon;

H is hydrogen;

O is oxygen;

N is nitrogen;

S is sulfur;

P is phosphorus;

v is zero or one;

w is zero or an integer ranging from 1 to 4;

x is an integer ranging from 1 to 4;

y is zero or an integer ranging from 1 to 6; and z is zero, one, two or three.

The present invention also relates to the use of PHEX inhibitors for the identification of PHEX substrates and to methods of identifying PHEX substrates.

In particular, it relates to a method for identifying PHEX substrates comprising contacting a candidate compound with PHEX in the presence and in the absence of a PHEX inhibitor of the present invention; assessing PHEX biological activity on the candidate compound in the presence and in the absence of the PHEX inhibitor, wherein the candidate compound is selected as a PHEX substrate when PHEX biological activity is measurably higher in the absence versus in the presence of the PHEX inhibitor. It also relates to a use of a PHEX inhibitor of the present invention, for identifying PHEX substrates comprising contacting a candidate with PHEX in the presence and in the absence of the PHEX inhibitor; and assessing PHEX biological activity on the candidate in the presence and in the absence of the PHEX inhibitor, wherein the candidate compound is selected as a PHEX substrate when PHEX biological activity is measurably higher in the absence versus in the presence of the compound.

It also relates to a method for stimulating bone mass formation in a mammal comprising inhibiting PHEX with an effective amount of a PHEX inhibitor of the present invention. It also relates to the use of a PHEX inhibitor of the present invention for stimulating bone mass formation in a mammal.

It also relates to a method for treating or preventing a disease or condition associated with a phosphate metabolism defect comprising administering an effective amount of PHEX inhibitor of the present invention to a mammal in need thereof. It also relates to uses a PHEX inhibitor of the present invention for treating or preventing a disease or condition associated with a phosphate metabolism. In specific embodiments, the disease or condition is selected from the group consisting of hyperphosphatemia, hyperparathyroidism and renal insufficiencies.

It also relates to a method for inhibiting PHEX comprising contacting PHEX with an inhibitory amount of a PHEX inhibitor of the present invention. It also relates to a use of a PHEX inhibitor of the present invention for inhibiting PHEX.

In addition, the present invention relates to methods of administration of the PHEX inhibitors as described herein.

Moreover, the present invention relates to the use of pharmaceutical preparations comprising an effective amount of a PHEX inhibitor in medical conditions such as hyperphosphatemia, hyperparathyroidism, in conditions related to renal insufficiencies such as renal osteodystrophy as well as in conditions wherein the metabolism of phosphate needs to be managed. In addition, the present invention relates to the use of inhibitors of PHEX capable of providing for faster bone-mass regeneration following bone-fractures, the implantation of orthopedic prostheses and the implantation of dental prostheses or after loss of bone mass as a result of bone diseases such as osteoporosis.

The present invention also relates to pharmaceutical preparation comprising an effective amount of a PHEX inhibitor in an admixture with a physiologically-acceptable carrier or excipient.

The terms "inhibiting," "reducing" or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Further scope and applicability will become apparent from the detailed description given hereinafter. It should be understood however, that this detailed description, while indicating preferred embodiments of the invention, is given by way of illustration only, since various changes and modifications within the spirit and scope of the invention will become apparent to those skilled in the art.

BRIEF DESCRIPTION OF THE DRAWINGS

Having thus generally described the invention, reference will now be made to the accompanying figures, showing by way of illustration a preferred embodiment thereof, and in which.

Figure 1:
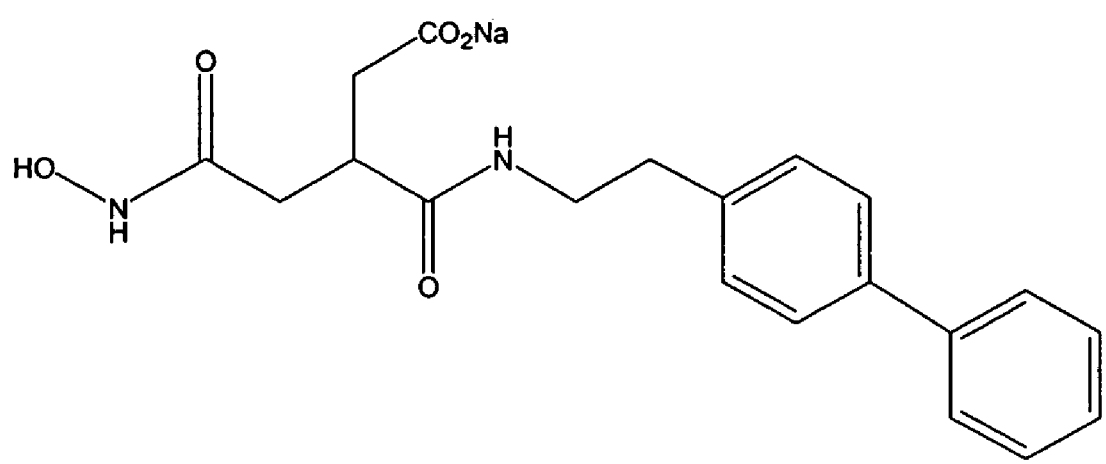
FIG. 1 shows the chemical structure of the PHEX inhibitor MH-2-64C (compound of Example 126)

Other objects, advantages and features of the present invention will become more apparent upon reading of the following non-restrictive description of preferred embodiments with reference to the accompanying drawings, which is exemplary and should not be interpreted as limiting the scope of the present invention.

DETAILED DESCRIPTION OF THE INVENTION

As used herein, "sPHEX" refers to a secreted soluble form of human PHEX which causes the hydrolysis of $PTHrP_{107-139}$ by cleaving peptide bonds on the amino-terminal side of aspartate amino acid residues. The present invention is to be understood as comprising the inhibition of all enzymes having such activity, a non-limiting example of which is membrane-bound PHEX.

As used herein, the term "PHEX inhibitor" comprises any compound that inhibits the enzymatic action of sPHEX.

The term "derivative" as used herein, is understood as being a substance which comprises the same basic carbon skeleton and carbon functionality in its structure as a given compound, but can also bear one or more substituents or rings. Non-limiting examples of derivatives of succinic acid include: 2-amino succinic acid (aspartic acid), dimethyl succinate, 2-benzyl succinic acid, succinic anhydride, 1-aminocyclopentane-1,2-dicarboxylic acid and 2,3-piperidinedicarboxylic acid.

As used herein, the terminology PHEX "biological activity" is meant to include enzymatic activity and binding of PHEX to other molecules including inhibitors and substrates.

The term "analog" as used herein, is understood as being a substance which does not comprise the same basic carbon skeleton and carbon functionality in its structure as a "given compound", but which can mimic the given compound by incorporating one or more appropriate substitutions such as for example substituting carbon for heteroatoms. Non-limiting examples of "analogs" include: cysteic acid is an analog of aspartic acid, O-phosphoserine, serine-O-sulfate and 2-amino-4-phosphobutanoic acid are analogs of glutamic acid.

The term "alkyl" as used herein, is understood as being straight or branched chain radicals having up to seven carbon atoms. The term "lower alkyl" as used herein, is understood as being straight or branched radicals having up to four carbon atoms and is a preferred sub-grouping for the term "alkyl".

The term "substituted alkyl" as used herein, is understood as being such straight or branched chain radicals having up to 7 carbon atoms wherein one or more, preferably one, two, or three hydrogen atoms have been replaced by a substituent selected from the group consisting of hydroxy, amino, cyano, halogen, trifluoromethyl, —NH(lower alkyl), —N(lower alkyl)$_2$, lower alkoxy, lower alkylthio, and carboxy, aryl and heteroaryl.

The terms "lower alkoxy" and "lower alkylthio" as used herein, are understood as being such lower alkyl groups as defined above attached to an oxygen or sulfur atom.

The term "cycloalkyl" as used herein, is understood as being saturated rings of 3 to 7 carbon atoms.

The term "alkenyl" as used herein, is understood as being straight or branched chain radicals of 3 to 7 carbon atoms having one or two double bonds. Preferred "alkenyl" groups are straight chain radicals of 3 to 5 carbon atoms and having one double bond.

The term "substituted alkenyl" as used herein, is understood as being such straight or branched radicals of 3 to 7 carbon atoms having one or two double bonds and wherein a hydrogen atom has been replaced by a substituent selected from the group consisting of hydroxy, amino, halo, trifluoromethyl, cyano, —NH(lower alkyl), —N(lower alkyl)$_2$, lower alkoxy, lower alkylthio, and carboxy.

The term "alkylene" as used herein, is understood as being divalent straight or branched chain radicals having up to seven carbon atoms (i.e. —CH$_2$—, —(CH$_2$)$_2$—, —(CH$_2$)$_3$—, —(CH$_2$)$_4$—, —CH$_2$—CH(CH$_3$)—, etc.).

The term "aryl" as used herein, is understood as being phenyl, 1-naphthyl, and 2-naphthyl. The term "substituted aryl" as used herein, is understood as being phenyl, 1-naphthyl and 2-naphthyl having a substituent selected from the group consisting of phenyl, heteroaryl, lower alkyl, lower alkoxy, lower alkylthio, halo, hydroxy, trifluoromethyl, amino, —NH(lower alkyl), and —N(lower alkyl)$_2$, as well as being mono-, di- and tri-substituted phenyl, 1-naphthyl, and 2-naphthyl comprising substituents selected from the group consisting of methyl, methoxy, methylthio, halo, hydroxy, and amino.

The term triphenylmethyl is herein abbreviated as Trt (trityl).

The term "heteroaryl" as used herein, is understood as being unsaturated rings of five or six atoms containing one or two O- and/or S-atoms and/or one to four N-atoms, provided that the total number of hetero-atoms in the ring is 4 or less. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl, and 2- and 3-furyl. The term "heteroaryl" as used herein, is understood as also including bicyclic rings wherein the five or six membered ring containing O, S and N-atoms as defined above is fused to a benzene or pyridyl ring. Preferred bicyclic rings include but are not limited to 2- and 3-indolyl as well as 4- and 5-quinolinyl. The mono or bicyclic heteroaryl ring can also be additionally substituted at an available carbon atom by a substituent selected from the group consisting of lower alkyl, halo, hydroxy, benzyl and cyclohexylmethyl. Additionally, if the mono or bicyclic ring has an available N-atom, then such an atom can also be substituted by one of the N-protecting groups such as N-carbamates, N-phenylsulfenyl, N-phenylsulfonyl, N-2,4-dinitrophenyl, N-lower alkyl, N-benzyl, or N-benzhydryl or any other applicable group known in the art (T. W. Greene, P. G. M. Wuts: Protective Groups in Organic Synthesis, 2$^{nd}$ Edition, John Wiley & Sons, NY, 1991).

The terms "halogen" or "halo" as used herein, is understood as being chlorine, bromine, fluorine and iodine.

The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps.

Examples of acid addition salts include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate.

Examples of basic salts include but are not limited to ammonium salts; alkali metal salts such as sodium, lithium, and potassium salts; alkaline earth metal salts such as calcium and magnesium salts; salts comprising organic bases such as amines (e.g., dicyclohexylamine, alkylamines such as t-butylamine and t-amylamine, substituted alkylamines, aryl-alkylamines such as benzylamine, dialkylamines, substituted dialkylamines such as N-methyl glucamine (especially N-methyl D-glucamine), trialkylamines, and substituted trialkylamines); and salts comprising amino acids such as arginine, lysine and so forth. The basic nitrogen-containing groups may be quaternized with agents such as lower alkyl halides (e.g. methyl, ethyl. propyl, and butyl chlorides, bromides and iodides), dialkyl sulfates (e.g. dimethyl, diethyl, dibutyl, and diamyl sulfates), long chain halides (e.g. decyl, lauryl, myrtistyl and stearyl chlorides, bromides and iodides), arylalkyl halides (e.g. benzyl and phenethyl bromides), and others known in the art.

Prodrugs and solvates of the PHEX inhibitors of the present invention are also contemplated herein. The term "prodrug" as used herein, is understood as being a compound which, upon administration to a subject, undergoes chemical conversion by metabolic or chemical processes to yield a compound of the Formula I, or a salt and/or solvate thereof (Bundgaard, 1991; Bundgaard, 1985). Solvates of the compounds of Formula I are preferably hydrates.

All possible stereoisomers of the PHEX inhibitors of the present invention are contemplated as being within the scope of the present invention. Individual stereoisomers of the compounds of the present invention may, for example, be substantially free of other stereoisomers, or may be admixed, for example, as racemates or admixed with other selected or all other stereoisomers. The chiral centers of the PHEX inhibitors of the present invention can have the S- or the R-configuration, as defined by the IUPAC 1974 Recommendations.

The compounds of Formula I wherein A, B, D, E, R, $R_1$, $R_2$, $R_3$, $R_4$ and v are as defined above, can be prepared by reacting a compound of Formula II,

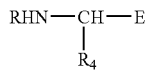
(II)

wherein R, $R_4$ and E are as defined above, and wherein E and $R_4$ (if needed) are suitably protected by a conventional protecting group so as not to interfere with the coupling reaction using conventional peptide synthesis methodology, with a derivative of Formula III

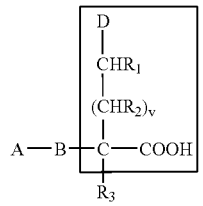
(III)

wherein A, B, D, $R_1$, $R_2$, $R_3$ and v are as defined above, and wherein A and D are suitably protected so as not to interfere with the coupling reaction, using conventional peptide synthesis methodology.

The compound of Formula III wherein B is $NR_{11}$ and wherein A, D, $R_1$, $R_2$, $R_3$ and v are as defined above, can be prepared via a condensation reaction between a compound of Formula IV,

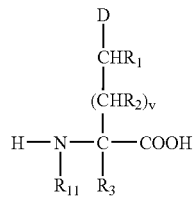
(IV)

suitably protected at the carboxyl and D groups and wherein $R_1$, $R_2$, $R_3$, $R_{11}$, D and v are as defined above, and a suitably protected precursor of A to give a compound of Formula IIIa, suitably protected at the carboxyl and D groups, wherein A, D, $R_1$, $R_2$, $R_3$, $R_{11}$, and v are as described above.

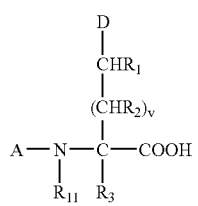
(IIIa)

When the compound of Formula IIIa includes a group A which is $R_6S$—$CHR_5$—$C(=O)$— wherein $R_5$ and $R_6$ are as defined above, it can be prepared by peptidic condensation of carboxy- and D-protected compound IV with an S-protected (and if needed, $R_5$ and $R_6$ protected) thioglycolic acid of Formula:

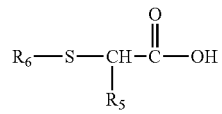

When the compound of Formula IIIa includes a group A which is $R_6S$—$CHR_5$—$(CH_2)_w$— wherein $R_5$ and $R_6$ are as defined above and wherein w=1, it can be prepared by reaction of carboxy- and D-protected compound IV with a thiiran of Formula (protected at $R_5$ if needed).

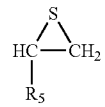

When the compound of Formula IIIa includes a group A which is TrtO—NH—C(=O)— wherein Trt is a trityl protecting group, it can be prepared by reaction of carboxy- and D-protected compound IV with trichloromethyl chloroformate followed by trapping of the resulting chloroformamide with O-tritylhydroxylamine.

When the compound of Formula IIIa includes a group A which is $R_8O$—C(=O)—$CHR_5$— wherein $R_5$ and $R_8$ are as defined above, it can be prepared by reductive amination involving carboxy- and D-protected compound IV and an α-keto ester (or the corresponding acid) protected at $R_8$ and/or $R_5$ (if needed) of Formula:

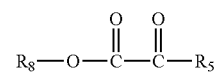

Alternatively, the above-mentioned compound IIIa can be prepared by reaction with a triflate (protected, if needed, at $R_8$ and $R_5$) of formula:

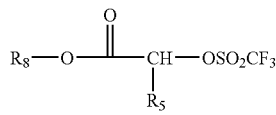

When the compound of Formula IIIa includes a group A which is Trt-O—NH—C(=O)$CHR_5$— wherein Trt is a trityl protecting group and $R_5$ is as defined above, it can be prepared by reaction of compound IIIa, protected at the carboxyl and D groups, wherein A is $R_8$—O—C(=O)—$CHR_5$— and wherein $R_5$ (protected if needed) and $R_8$ are as defined above, with O-trityl-protected hydroxylamine.

When the compound of Formula IIIa includes a group A which is $R_9O$—P(=O)$R_{10}$— wherein $R_9$ and $R_{10}$ are as defined above, it can be prepared by condensation of carboxy- and D-protected compound IV with a phosphonochloridate (with $R_9$ and $R_{10}$ protected, if needed) of the Formula:

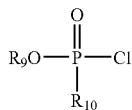

When the compound of Formula IIIa includes a group A which is $(R_9O)_2P(=O)-CHR_5-$ wherein $R_5$ and $R_9$ are as defined above, it can be prepared by reacting compound IV or a salt thereof with an aldehyde of formula $R_5-CHO$ having $R_5$ protected if needed, followed by treating the product of this reaction with a phosphite of Formula:

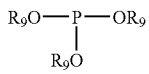

When the compound of Formula IIIa includes a group A which is $R_{10}R_9OP(=O)-CHR_5-C(=O)-$ wherein $R_5$, $R_9$ and $R_{10}$ are as defined above, it can be prepared by reacting carboxy- and D-protected compound IV with a phosphinyl acetic acid derivative of Formula:

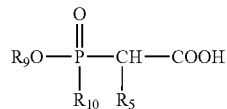

(with $R_5$, $R_9$, and $R_{10}$ protected if needed) following known amide bond forming procedures.

In the preceding set of reactions, a reaction sequence was followed in which compounds of Formula III were assembled by formation of the A-B bond, followed by coupling of the compounds of Formula III to compounds of Formula II to provide compounds of Formula I. The reverse sequence in which the amide bond to compounds of Formula II is first formed, followed by the formation of the A-B bond, is equally feasible.

The compounds of Formula II wherein E, R and $R_4$ are defined as above, can in many cases be obtained from commercial sources, particularly when it is a natural or non-natural α-amino acid or its decarboxylation product or when E is hydrogen or —COOH. In the case where E is a simple primary, secondary or tertiary amide, a peptide bond to an amino acid, an ester or a hydroxymethyl group, these compounds can all be prepared from the compound wherein E is —COOH by procedures well known in the art. Finally, the carbon chain elongated analogs of compound II wherein E is —CH$_2$COOH or —CH$_2$CH$_2$OH can also be prepared from compounds wherein E is —COOH by procedures well known in the art.

Many compounds of Formula IV which are substituted derivatives and analogs of α-aminosuccinic acid (aspartic acid) and α-amino glutaric acid (glutamic acid) are commercially available and can be found in *The Protein Synthesis Database* (PSD) from *The Biotechnology Research Institute* (BRI) of *The National Research Council of Canada* (NRCC). Specific examples of compounds of Formula IV, included herein in their unprotected and variously protected forms are: D-Aspartic acid, L-Aspartic acid, DL-Aspartic acid, N-Methyl-D-aspartic acid, N-Methyl-L-aspartic acid, alpha-Methyl-D-aspartic acid, DL-threo-beta-Methylaspartic acid, D-(+)-threo-beta-Hydroxyaspartic acid, DL-threo-beta-Hydroxyaspartic acid, L-(+)-threo-beta-Hydroxyaspartic acid, L-Cysteinesulfinic acid, L-Cysteic acid, L-(+)-2-Amino-3-phosphonopropionic acid, D-(−)-2-Amino-3-phosphonopropionic acid, Cis-2,3-Piperidinedicarboxylic acid, (±)-1-Aminocyclopentane-cis-1,2-dicarboxylic acid, (±)-1-Aminocyclopentane-trans-1,2-dicarboxylic acid, (±)-1-Aminocyclohexane-cis-1,2-dicarboxylic acid, (±)-1-Aminocyclohexane-trans-1,2-dicarboxylic acid, L-Glutamic acid, D-Glutamic acid, DL-Glutamic acid, (2R, 4R)-(+)-Azetidine-2,4-dicarboxylic acid, (2S, 4S)-(+)-Azetidine-2,4-dicarboxylic acid, γ-Methylene-DL-glutamic acid, 1-Aminocyclobutane-cis-1,3-dicarboxylic acid, 1-Aminocyclobutane-trans-1,3-dicarboxylic acid, (2S, 1'R, 2'S)-2-(Carboxycyclopropyl)glycine, (2S, 1'S, 2'R)-2-(Carboxycyclopropyl)glycine, (2S, 1'S, 2'S)-2-(Carboxycyclopropyl)glycine, N-Methyl-L-Glutamic acid, α-Methyl-DL-Glutamic acid, (2S, 4R)-4-Methylglutamic acid, 4-Fluoroglutamic acid, cis-2,4-Piperidinedicarboxylic acid, (1R, 3R)-1-Aminocyclopentane-1,3-dicarboxylic acid, (1R, 3S)-1-Aminocyclopentane-1,3-dicarboxylic acid, (1S, 3R)-1-Aminocyclopentane-1,3-dicarboxylic acid, (1S, 3S)-1-Aminocyclopentane-1,3-dicarboxylic acid, (2S)-α-Ethylglutamic acid, D-Homocysteic acid, L-Homocysteic acid, L(+)-2-Amino-4-phosphonobutanoic acid, D(+)-2-Amino-4-phosphonobutanoic acid, L-Serine O-sulfate, O-Phospho-L-serine, O-Phospho-D-serine, (±)-1-Aminocyclohexane-cis-1,3-dicarboxylic acid, L-γ-carboxyglutamic acid, D-γ-carboxyglutamic acid, (S)-2-Amino-2-methyl-4-phosphonobutanoic acid, O-Phospho-L-threonine, O-Phospho-DL-threonine, Kainic acid, and Dihydrokainic acid.

The compound of Formula III wherein B is CH$_2$, A is $R_6S-CHR_5-(CH_2)_w-$, D, $R_5$ and $R_6$ are as defined above, wherein $R_1$, $R_2$ and $R_3$ are hydrogen, w=0 and v=0 or 1, and which is hereinafter specified as compound of Formula IIIb, can be prepared according to the reaction sequence illustrated in Scheme 1 (appropriate protecting groups are used as needed). The sequence begins with succinic acid monomethyl ester, the dianion of which is alkylated with electrophile V or VI to give compound of the formula VII. The latter is reduced to the corresponding aldehyde VIII using 9-BBN. Grignard reaction on aldehyde VIII gives compound IX which is converted to the corresponding thioester X under Mitsunobu conditions. Finally, compound IIIb wherein B is CH$_2$, A is $R_6-S-CHR_5-(CH_2)_w-$, D, $R_5$ and $R_6$ are as defined above, wherein $R_1$, $R_2$ and $R_3$ are hydrogen and wherein w=0 and v=0 or 1, is obtained by basic hydrolysis of thioester X followed by the introduction of $R_6$ by standard methods.

Scheme 1

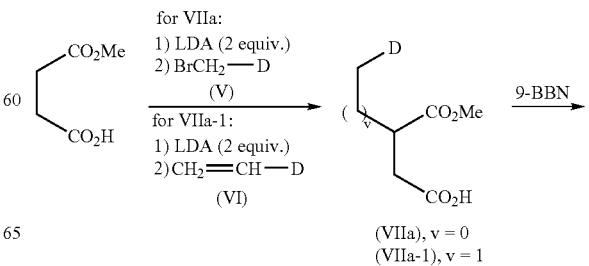

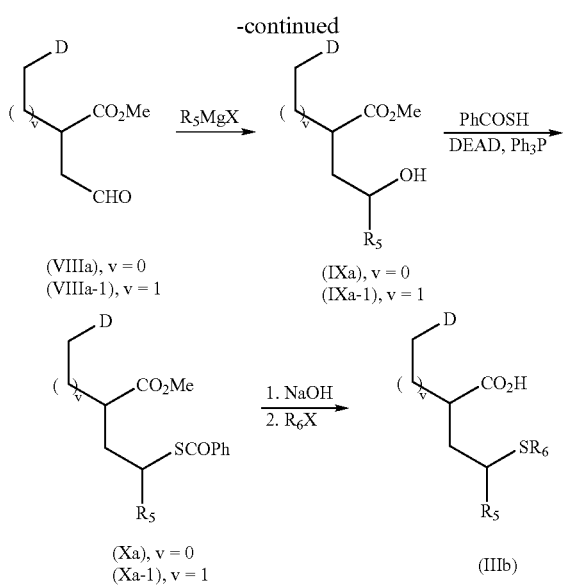

(VIIIa), v = 0
(VIIIa-1), v = 1

(IXa), v = 0
(IXa-1), v = 1

(Xa), v = 0
(Xa-1), v = 1

(IIIb)

The compound of Formula III wherein B is CH$_2$, A is R$_6$S—CHR$_5$—(CH$_2$)$_w$—, D, R$_5$ and R$_6$ are as defined above, wherein R$_1$, R$_2$ and R$_3$ are hydrogen and wherein w=1 and v=0 or 1, and which is hereinafter referred to as compound of Formula IIIc, can be prepared according to the reaction sequence illustrated in Scheme 2. Scheme 2 involves the same reaction sequence as the one previously illustrated in Scheme 1, except that it starts from the next higher carbon homologue, i.e., glutaric acid monomethyl ester.

Scheme 2

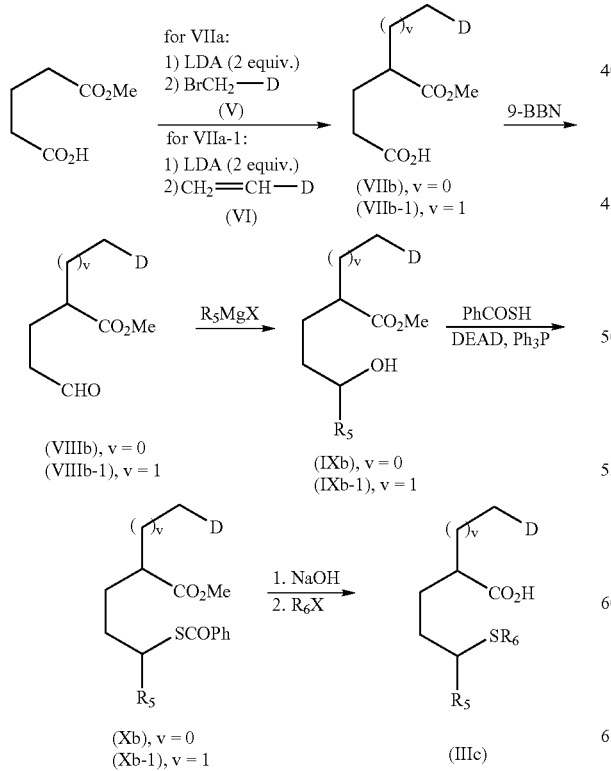

(VIIIb), v = 0
(VIIIb-1), v = 1

(IXb), v = 0
(IXb-1), v = 1

(Xb), v = 0
(Xb-1), v = 1

(IIIc)

The compound of Formula III wherein B is CH$_2$, A is TrtO—NH—C(=O)—, D is as defined above, wherein R$_1$, R$_2$ and R$_3$ are hydrogen and wherein v=0 or 1 and which is hereinafter specified as compound of Formula IIId, can be prepared by reacting compound VIIa or VIIa-1 with O-tritylhydroxylamine under peptide bond forming conditions, followed by base hydrolysis of the methyl ester.

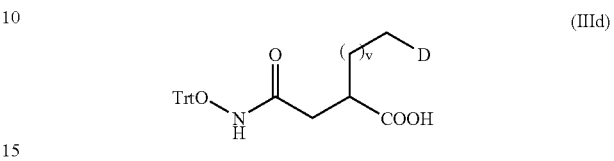

(IIId)

The compound of Formula III wherein B is CH$_2$, A is R$_8$—O—C(=O)—CHR$_5$—, D, R$_5$ and R$_8$ are as defined above, wherein R$_1$, R$_2$ and R$_3$ are hydrogen and wherein v=0 or 1, and which is hereinafter referred to as compound of Formula IIIe, can be prepared by the reaction sequence illustrated in Scheme 3, starting from aldehyde VIIb or VIIIb-1 and where R$_5$ and R$_8$ are protected if needed.

Scheme 3

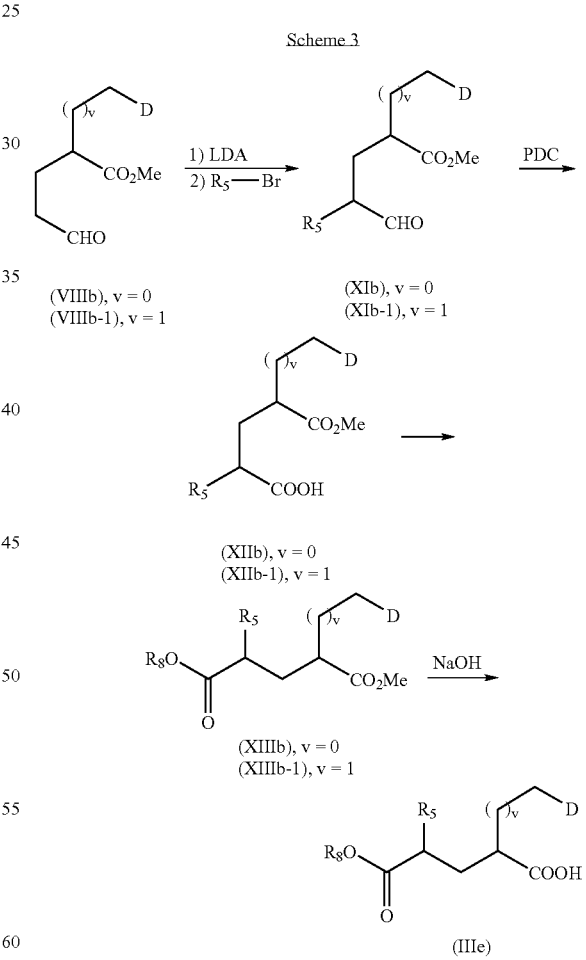

(VIIIb), v = 0
(VIIIb-1), v = 1

(XIb), v = 0
(XIb-1), v = 1

(XIIb), v = 0
(XIIb-1), v = 1

(XIIIb), v = 0
(XIIIb-1), v = 1

(IIIe)

The sequence begins with the alkylation of aldehyde VIIIb or VIIIb-1 with R$_5$—Br to give compound XI. Pyridinium dichromate (PDC) oxidation of the aldehyde gives the corresponding acid XII. The latter is then converted to its tert-butyl ester using tert-butyl 2,2,2-trichloroacetimidate, followed by the selective hydrolysis of the methyl ester using aqueous base to give compound IIIe.

The compound of Formula III wherein B is $CH_2$, A is $TrtO-NH-C(=O)-CHR_5-$, D and $R_5$ are as defined above, wherein $R_1$, $R_2$ and $R_3$ are hydrogen and wherein v=0 or 1 and which is hereinafter referred to as compound of Formula IIIf, can be prepared by reacting compound XIIb or XIIb-1 (Scheme 3) (having $R_5$ protected if needed) with O-tritylhydroxylamine under peptide bond forming conditions, followed by base hydrolysis of the methyl ester.

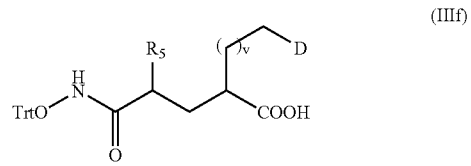

(IIIf)

The compound of Formula III wherein B is $CH_2$, A is $R_{10}R_9OP(=O)-$, wherein D, $R_9$ and $R_{10}$ are as defined above, wherein $R_1$, $R_2$ and $R_3$ are hydrogen and wherein v=0 or 1, and which is hereinafter specified as compound of Formula IIIg, can be prepared according to known procedures (U.S. Pat. No. 4,168,267).

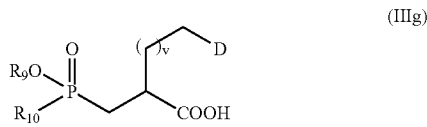

(IIIg)

The compound of Formula III wherein B is $CH_2$, A is $(R_9O-)_2P(=O)-CHR_5-$, wherein D, $R_5$ and $R_9$ are as defined above, wherein $R_1$, $R_2$ and $R_3$ are hydrogen and wherein v=0 or 1 and which is hereinafter specified as compound of Formula IIIh, can be prepared according to Scheme 4 where $R_5$ and $R_9$ can be protected if needed.

Scheme 4

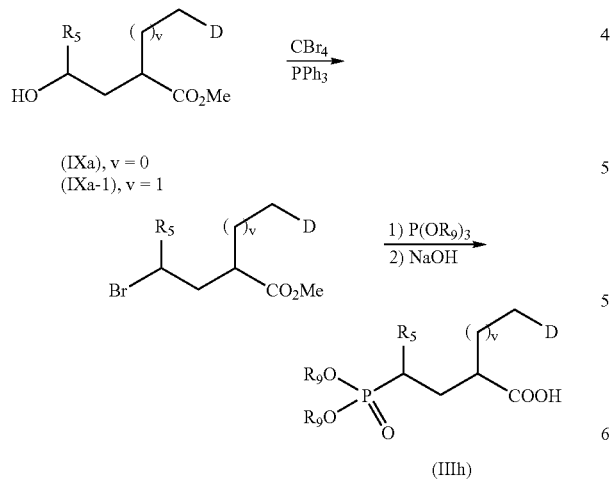

The synthetic sequence involves the conversion of alcohol IXa or Ixa-1 (Scheme 1) to its corresponding bromide using $CBr_4/PPh_3$ followed by an Arbuzov reaction and basic hydrolysis of the methyl ester.

The compound of Formula III wherein B is absent, A is $R_6-S-CHR_5-(CH_2)_w-$, wherein D, $R_5$ and $R_6-$ are as defined above, wherein $R_1$, $R_2$ and $R_3$ are hydrogen and wherein w=0 and v=0 or 1, and which is hereinafter specified as compound of Formula IIIi, can be prepared according to the reaction sequence illustrated in Scheme 5 starting from diethyl malonate and where $R_5$ and $R_6$ can be protected if needed.

Scheme 5

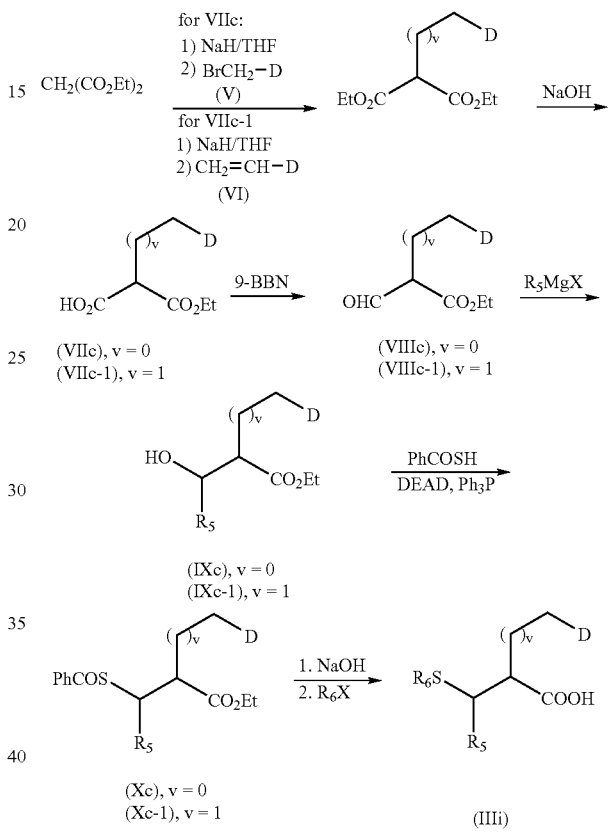

This sequence involves the same reactions as those previously described in Schemes 1 and 2 to prepare the higher homologues IIIb and IIIc.

The compound of Formula III wherein B is absent, A is $TrtONH-C(=O)-$, D is as defined above, wherein $R_1$, $R_2$ and $R_3$ are hydrogen and wherein v=0 or 1, and which is hereinafter referred to as compound of Formula IIIj, can be prepared by reacting compound VIIc or VIIc-1 (Scheme 5) with O-trityl hydroxylamine under peptide bond forming conditions followed by base hydrolysis of the ethyl ester.

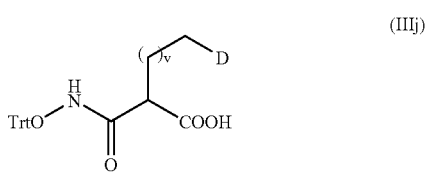

(IIIj)

The compound of Formula III wherein B is absent, A is $R_8-O-C(=O)-CHR_5-$, wherein D, $R_5$ and $R_8$ are as defined above, wherein $R_1$, $R_2$ and $R_3$ are hydrogen and wherein v=0 or 1, and which is hereinafter specified as compound of the Formula IIIk, can be prepared according to the reaction sequence illustrated in Scheme 6, where $R_5$ and $R_8$ can be protected if needed.

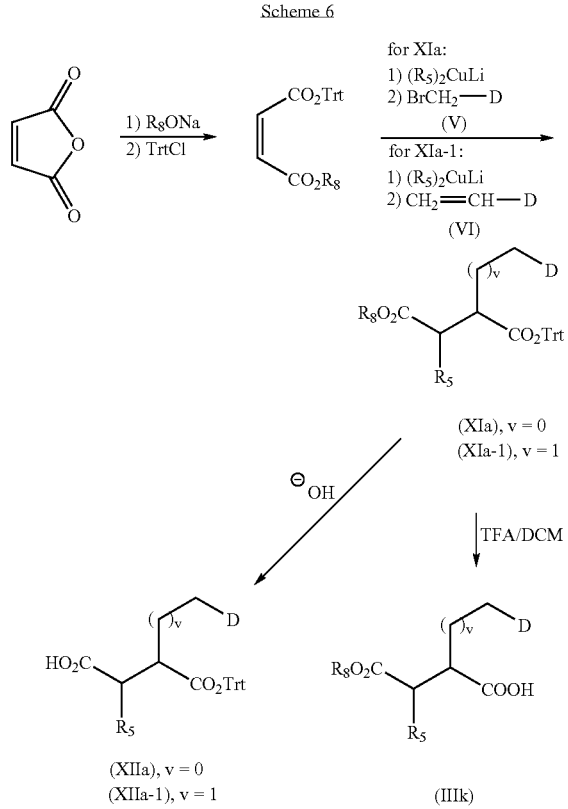

Thus, opening of maleic anhydride with the sodium alkoxide $R_8$ONa gives the half ester which upon treatment with trityl chloride affords the mixed maleic diester. Conjugate addition/enolate trapping gives predominantly the correct succinate regioisomer as predicted based on steric control grounds. Finally, selective hydrolysis of the trityl ester affords the target compound IIIk.

The compound of Formula III wherein B is absent, A is BnO—NH—C(=O)—$CHR_5$—, wherein D and $R_5$ are as defined above, wherein $R_1$, $R_2$ and $R_3$ are hydrogen and wherein v=0 or 1, and which is hereinafter referred to as compound of Formula IIII, can be prepared by reacting compound XII, obtained by selective hydrolysis of XI (Scheme 6), with O-benzylhydroxylamine under peptide bond forming conditions followed by cleavage of the trityl ester.

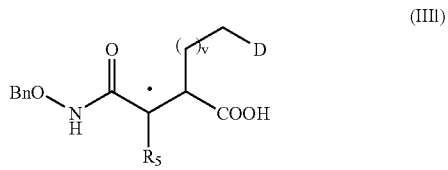

(IIIl)

The compound of Formula III wherein B is absent, A is $R_{10}R_9$O—P(=O)—, wherein D, $R_9$ and $R_{10}$ are as defined above, wherein $R_1$, $R_2$ and $R_3$ are hydrogen and wherein v=0 or 1, and which is hereinafter specified as compound of Formula IIIm, can be prepared according to known procedures (U.S. Pat. No. 4,168,267).

The compound of Formula III wherein B is absent, A is $(R_9$—O—$)_2$P(=O)—$CHR_5$—, wherein D, $R_5$ and $R_9$ are as defined above, wherein $R_1$, $R_2$ and $R_3$ are hydrogen and wherein v=0 or 1, and which is hereinafter specified as compound of Formula IIIn, can be prepared according to Scheme 7 where $R_5$ can be protected if needed.

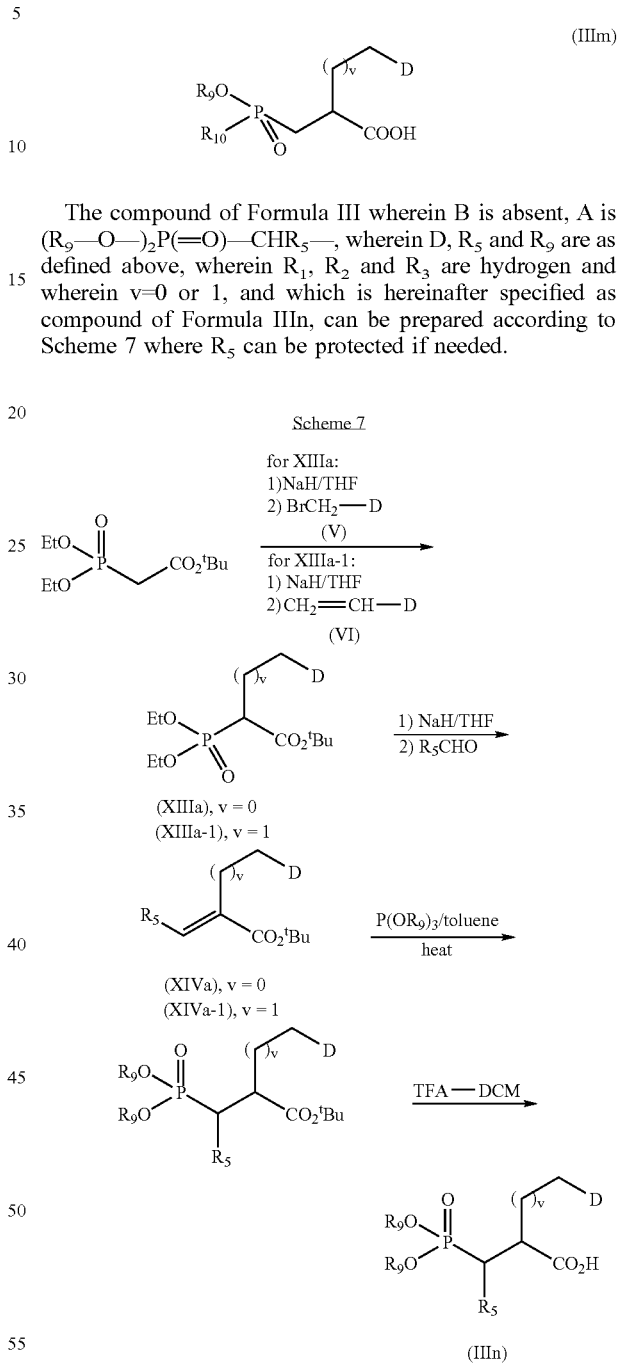

The synthetic sequence in scheme 7 involves the alkylation of commercially available tert-butyl diethylphosphonoacetate to give the mixed ester XIII. Condensation of the in-situ generated anion of XIII with aldehyde $R_5$CHO affords the substituted acrylate derivative XIV. Arbuzov-type conjugate addition to acrylate XIV followed by TFA removal of the tert-butyl ester group furnishes target compound IIIn.

The compound of Formula III wherein B is $CH_2$, A is $R_{10}R_9$OP(=O)—$CHR_5$—, wherein D, $R_5$, $R_9$ and $R_{10}$ are as defined above, wherein $R_1$, $R_2$ and $R_3$ are hydrogen and wherein v=0 or 1, and which is hereinafter specified as compound of Formula IIIo, can be prepared according to Scheme 8 where $R_5$, $R_9$ and $R_{10}$ can be protected if needed.

The synthetic sequence in Scheme 8 involves first halogenation of the starting alcohol IXa or IXa-1 to give the corresponding bromoester XV. The later is converted to the monosubstituted phosphinic acid which is then protected as its ester XVI by reacting with $R_9OH$. Finally, Arbuzov reaction with alkyl bromide $R_{10}Br$ on diester XVI followed by hydrolysis of the methyl ester gives the target compound IIIo.

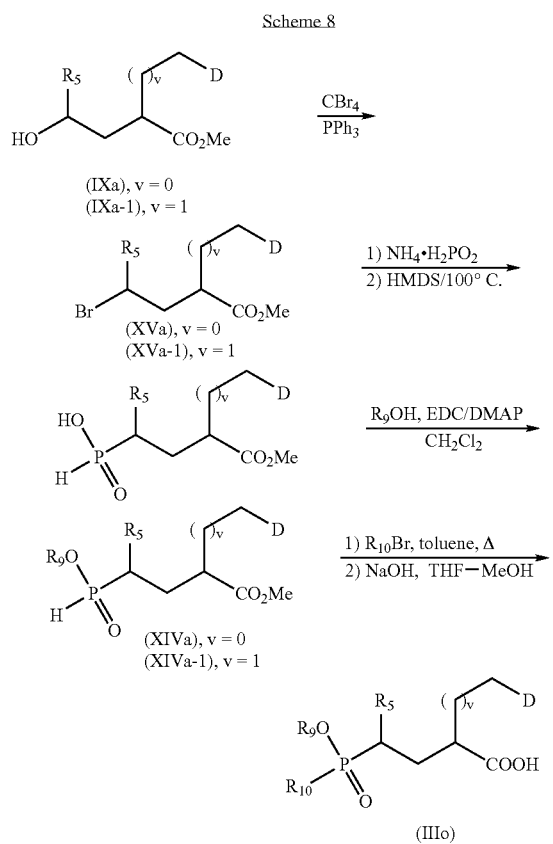

The compound of Formula III wherein B is $CH_2$, A is $R_{10}R_9OP(=O)$—$CHR_5$—$CH_2$, wherein D, $R_5$, $R_9$ and $R_{10}$ are as defined above, wherein $R_1$, $R_2$ and $R_3$ are hydrogen and wherein v=0 or 1, and which is hereinafter specified as compound of Formula IIIp, can be prepared according to Scheme 9, where $R_5$, $R_9$ and $R_{10}$ can be protected if needed. Scheme 9 involves the same reaction sequence as the one previously illustrated in Scheme 8, except that it starts from alcohol IXb or IXb-1 instead of IXa or IXa-1.

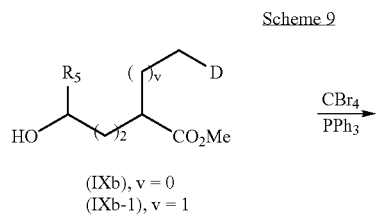

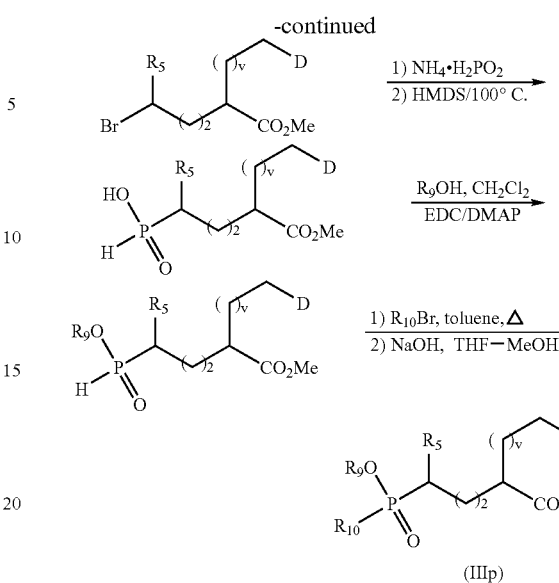

The compound of Formula V wherein D is —$COOR_5$ can in some cases be obtained from commercial sources or simply prepared by reacting the corresponding alcohol $R_5OH$ with commercially available bromoacetyl bromide or chloride.

$$\underset{Br}{\overset{D}{\underset{|}{CH_2}}} \quad (V)$$

The compound of Formula V wherein D is —P(=O)(OR$_5$)$_2$ can in some cases be obtained from commercial sources or simply prepared by reacting the corresponding alcohol $R_5OH$ with commercially available chloromethylphosphonic dichloride followed by exchanging the chloride of the chloromethyl group for bromide using sodium bromide.

In those cases where D is $SO_3H$, its introduction into the compounds of Formula I and III, as well as in their precursors, can be achieved by a sequence of reactions that does not involve the use of a compound of Formula V to reach intermediate (VIIa), v=0. The intermediate of Formula (VIIa), v=0, can be prepared according to the reaction sequence illustrated in Scheme 10.

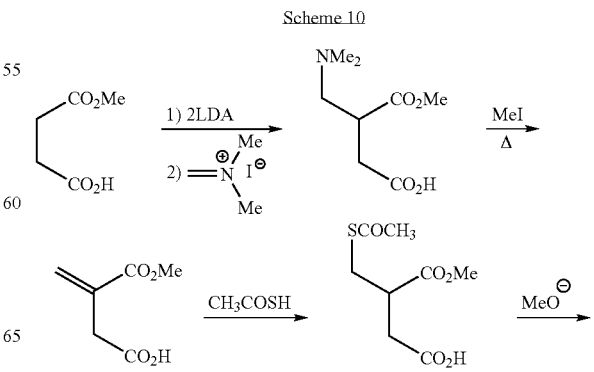

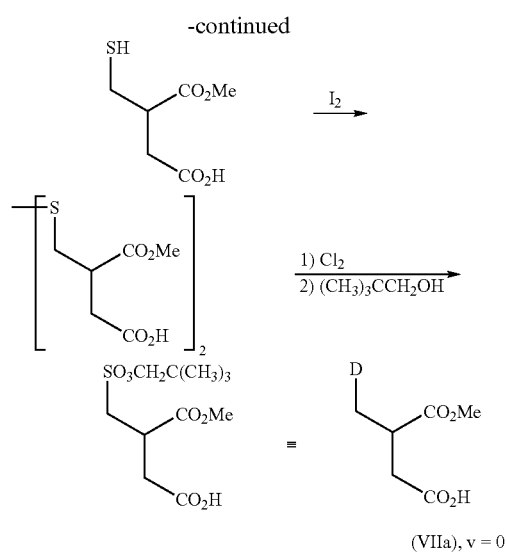

wherein D is —SO₃CH₂C(CH₃)₃

Scheme 10, which is based on known literature precedents, involves the use of an α-methylenation reaction followed by conjugate addition of a thiocarboxylic acid to the resulting acrylate ester (See for example Roques et al. U.S. Pat. No. 4,513,009; Ondetti et al. U.S. Pat. Nos. 4,105,776 and 4,339,600; Haslanger et al. U.S. Pat. No. 4,801,609 and Delaney et al. U.S. Pat. No. 4,722,810). Methanolysis of the resulting thioester gives the corresponding thiol which is oxidized to its disulfide dimer. The latter is then oxidatively cleaved by chlorine to give the corresponding sulfonyl chloride compound which is converted to its neopentyl ester (VIIa), v=0 wherein D is —SO₃CH₂C(CH₃)₃, a protected form of —SO₃H.

The compounds of formula (VI) (see for example Scheme 1) can be obtained from commercial sources and can be protected using methods known in the art.

The compounds of the present invention may be prepared by standard techniques known to those skilled in the art. Preferred procedures for the synthesis of these compounds are described below.

Amide bonds in the following examples are generally prepared by condensation between carboxylic acids and amines. Reagents capable of effecting this condensation include, but are not limited to, oxalyl chloride, thionyl chloride, phosphoryl chloride, diarylphosphoryl azides, diarylphosphoryl cyamide and carbodiimides. Carbodiimides in conjunction with 1-hydroxybenzotriazole, N-hydroxysuccinimide, and other reagents well known in the synthesis of amide bonds and peptides may also be utilized. Salts of the described carboxylic acids may generally be used in place of the carboxylic acids. Likewise, salts of the described amines may frequently be used in place of the amines.

In some examples, alkyl and arylalkyl esters have been utilized to protect carboxylic acids, hydroxamic acids, phosphonic acids and phosphinic acids. The protecting groups can be removed by well-established procedures. Thus t-butyl esters can be cleaved by mineral or organic acids such as HCl, HBr, or trifluoroacetic acid. Primary alkyl esters can be hydrolyzed with base. Benzyl esters can also be removed by hydrogenolysis (Greene, 1999).

Various peptide libraries are prepared by manual and/or automated liquid and solid phase synthesis techniques known in the art of combinatorial chemistry (Thompson et al.; 1996; Hermkens et al., 1996; Balkenhohl et al., 1996; Furka et al., 1996; Terrett et al., 1995). Instruments such as the Advanced ChemTech 440 Multiple Organic Synthesizer (440 MOS) were used to generate compound libraries in an automated fashion (Rivero et al., 1997). Among the various solid phase supports, the Wang and 2-Cl-Trityl resins were most often used. Non-limiting examples of the side chain protecting groups used in the present invention include: Asp (ᵗBu), Asn (Trt), Arg (Pmc), Glu (ᵗBu), His (Trt), Ser (ᵗBu), Thr (ᵗBu), Trp (Boc), and Tyr (ᵗBu).

General Procedures for the Solid Phase Peptide Synthesis:

In the solid-phase peptide synthesis techniques using Fmoc/ᵗBu chemistry (Atherton and Sheppard, 1987), the N-α-Fmoc group was cleaved with 25% (v/v) of piperidine in DMF for 5 min with continuous mixing followed by another treatment with fresh reagent for 25 min with continuous mixing. The resin was then filtered and washed sequentially with DMF (3×), DCM (3×), MeOH (3×), DCM (3×), and finally with MeOH (3×). The coupling reactions were done twice using a 4-fold and then a 2-fold molar excess of reagents in order to maximize efficiency. After washing and drying, cleavage was done using different cocktail mixtures depending on the type of resin and peptide sought. For example, cocktail A: TFA (94%): $H_2O$ (2.5%): EDT (2.5%): TIS (1.0%) was added to the resin with mixing for 2 h at room temperature. After filtration, the resin was washed by a fresh aliquot of the cleavage cocktail.

The cleaved samples were obtained by evaporation on a speed-vac machine and the remaining residues were precipitated with a cold mixture of ether:hexane (1:2). The isolated peptides were washed with cold ether:hexane (1:2, 2×), dissolved in $H_2O$ and then lyophilized. In those cases where some peptides gave fine crystals, centrifugation was used to isolate the products. Those samples which did not provide any precipitate were portioned between $H_2O$ and the above organic mixture and the aqueous layers were extracted (3×) with the above mixture and were then lyophilized. In those cases where a particular protected peptide with free carboxy terminus is needed for further elaboration, the cleavage was done using a mixture of $CH_2Cl_2$ (DCM) and hexafluoroisopropanol (HFIP), cocktail B, (DCM:HFIP, 4:1).

The library samples were checked for purity by HPLC and MS.

The names of the compounds described in the examples below were generated using the "Chemdraw Ultra™" (version 7.0.1) software of CambridgeSoft.

EXAMPLE 1

(R)-2-Bromo-3-phenyl-propionic acid

Potassium bromide (24.49 g, 0.21 moles) was first dissolved in a 2.50 N aqueous solution of sulfuric acid (120 mL). To this stirring solution was then added D-phenylalanine (10.00 g, 60.54 mmoles). After the addition, the mixture was cooled down to 0° C. and sodium nitrite (6.27 g., 90.87 mmoles) was added in small portions during 30 minutes. A strong bubbling was observed. The reaction was kept at this temperature for 50 minutes, and it was then allowed to proceed at room temperature for another 60 minutes. The crude product was isolated using standard work up and the obtained residue was purified by flash chromatography ($SiO_2$, 30% ethyl acetate–70% hexanes) to give 7.20 g (51.9% yield) of the title compound as a yellowish oil: ¹H NMR (CDCl$_3$, 300 MHz) ☐ 10.86 (br s, 1H), 7.31 (m, 5H), 4.48 (t, 1H), 3.51 (dd, 1H), 3.29 (dd, 1H); $^{13}$C NMR (CDCl$_3$, 75 MHz) ☐175.29, 136.26, 129.10, 128.69, 127.42, 44.83, 40.62.

EXAMPLE 2

(R)-2-Acetylsulfanyl-3-phenyl-propionic acid

The cesium thioacetate, prepared from 10.75 g of cesium carbonate and 2.51 g of thioacetic acid, was taken into dry DMF (25 mL) and to this solution was transferred the compound of example 1 (31.43 mmoles) previously dissolved in anhydrous DMF (25 mL). The mixture was shaken for 20 hours at room temperature and the product was isolated using standard work up to give 6.68 grams (94.8% yield) of the crude thioacetate. The compound was directly used in the next step without any further purification.

EXAMPLE 3

(S)-2-Mercapto-3-phenyl-propionic acid

To a stirring solution of the compound of example 2 (6.68 g, 29.78 mmoles) in degassed methanol (350 mL) was added dropwise a degassed 10% aqueous solution of potassium carbonate (9.61 g, 69.56 mmoles). The mixture was shaken at room temperature for 3 hours and the product was isolated using standard work up to give 5.26 g (96.9% yield) of a yellow oil which was used immediately in the next step without any further purification.

EXAMPLE 4

(S)-3-Phenyl-2-tritylsulfanyl-propionic acid

To a stirring solution of the above thioacid (5.26 g, 28.86 mmoles) in dry THF (20 mL) was transferred drop-wise a solution of triphenylmethyl chloride (12.07 g, 43.30 mmoles) in dry THF (20 mL). The mixture was stirred at room temperature for 24 hours and was then evaporated under vacuum. The crude residue was purified by flash chromatography (SiO$_2$, 20% EtOAc:80% Hexanes) to afford 6.02 g (49.1% yield) of the desired compound as a white solid: $^1$H NMR (CDCl$_3$, 300 MHz) ☐ 7.40 (m, 6H) 7.20 (m, 12H), 6.88 (d, 2H), 3.14 (dd, 1H), 2.92 (dt, 1H), 2.48 (dd, 1H); $^{13}$C NMR (CDCl$_3$, 75 MHz) ☐ 178.93, 144.47, 137.81, 130.11, 129.58, 129.11, 128.46, 127.42, 127.31, 68.98, 49.57, 39.54.

The following 2-tritylsulfanyl acids (compounds of examples 5–20) were prepared following the same sequence as that described in examples 1–4, where the starting 2-bromo carboxylic acid is obtained by nitrous acid deamination of the corresponding α-amino acid in the presence of HBr.

EXAMPLE 5

4-Phenyl-2-tritylsulfanyl-butyric acid $^1$H NMR (CDCl$_3$, 400 MHz) δ 7.49 (m, 6H), 7.31–7.16 (m, 12H), 7.02 (m, 2H), 2.99 (dd, 1H), 2.56–2.39 (m, 2H), 2.05–1.95 (m,1H), 1.66–1.59 (m, 1H); $^{13}$C NMR (CDCl$_3$, 400 MHz) δ 178.6, 144.0, 140.4, 129.5, 128.2, 127.8, 126.8, 125.9, 114.3, 95.7, 68.3, 46.8, 34.6, 33.4; MS (FAB-/LR/NBA) 437.0.

EXAMPLE 6

Phenyl-tritylsulfanyl-acetic acid $^1$H NMR (CDCl$_3$, 400 MHz) δ 7.41–7.09 (m, 20H), 4.11 (s, 1H); $^{13}$C NMR (CDCl$_3$, 400 MHz) δ 177.0, 143.6, 135.9, 129.6, 128.5, 128.1, 128.0, 127.8, 126.8, 69.0, 52.3; MS (MAB/HR/N2) 409.1271 HRMS calcd for C$_{27}$H$_{21}$O$_2$S 409.126227. found 409.127133.

EXAMPLE 7

3-Biphenyl-4-yl-2-tritylsulfanyl-propionic acid $^1$H NMR (CDCl$_3$, 400 MHz) δ 11.40 (br s, 1H), 7.59–7.06 (m, 24H), 3.24 (dd, 1H), 3.05 (dd, 1H), 2.60 (dd, 1H); $^{13}$C NMR (CDCl$_3$, 400 MHz) δ 178.4, 144.0, 140.7, 139.7, 136.4, 129.6, 129.5, 128.7, 127.9, 127.1, 127.0, 126.9, 68.5, 49.1, 38.7; MS (FAB-/NBA) 499.0.

EXAMPLE 8

3-Naphthalen-2-yl-2-tritylsulfanyl-propionic acid $^1$H NMR (CDCl$_3$, 400 MHz) δ 11.50 (br s, 1H), 7.86–7.73 (m, 3H), 7.53–7.09 (m, 19H), 3.33 (dd, 1H), 3.21 (dd, 1H), 2.75 (dd, 1H); $^{13}$C NMR (CDCl$_3$, 400 MHz) δ 178.5, 144.0, 134.9, 133.3, 132.3, 129.6, 128.0, 127.8, 127.6, 127.5, 127.2, 126.9, 126.0, 125.7, 68.6, 49.1, 39.2; MS (FAB-/NBA) 473.0.

EXAMPLE 9

3-(4-Fluoro-phenyl)-2-tritylsulfanyl-propionic acid $^1$H NMR (CDCl$_3$, 400 MHz) δ 7.50 (d, 6H), 7.30–7.20 (m, 9H), 6.92–6.83 (m, 4H), 3.08 (dd, 1H), 2.88 (dd, 1H), 2.41 (dd, 1H); $^{13}$C NMR (CDCl$_3$, 400 MHz) δ 177.9, 143.8, 132.9, 130.6, 130.5, 129.5, 127.9, 126.9, 115.2, 114.9, 95.7, 68.6, 49.0, 38.1; MS (FAB-/LR/NBA) 441.0.

EXAMPLE 10

3-(4-Methoxy-phenyl)-2-tritylsulfanyl-propionic acid

MS (FAB-/NBA) 453.0.

EXAMPLE 11

3-(4-Benzyloxy-phenyl)-2-tritylsulfanyl-propionic acid $^1$H NMR (CDCl$_3$, 400 MHz) δ 7.50–7.20 (m, 21H), 6.89 (s, 3H), 5.02 (s, 2H), 3.14 (dd, 1H), 2.92 (dd, 1H), 2.48 (dd, 1H); $^{13}$C NMR (CDCl$_3$, 400 MHz) δ 178.7, 157.7, 144.1, 136.9, 130.2, 129.8, 129.7, 128.5, 128.0, 127.9, 127.4, 127.0, 114.7, 69.9, 68.5, 49.4, 38.3; MS (FAB-/LR/NBA) 528.8.

EXAMPLE 12

3-Cyclohexyl-2-tritylsulfanyl-propionic acid

MS (FAB-/LR/NBA) 429.0.

EXAMPLE 13

2-Tritylsulfanyl-propionic acid

MS (MAB/HR/N2) 348.1194 HRMS calcd for $C_{22}H_{20}O_2S$ 348.118402. found 348.119379.

EXAMPLE 14

2-Tritylsulfanyl-hexanoic acid $^1$H NMR (CDCl$_3$, 400 MHz) δ 10.97 (br s, 1H), 7.58 (m, 6H), 7.37–7.21 (m, 9H), 2.99 (dd, 1H), 1.80–1.74 (m, 1H), 1.43–1.21 (m, 5H), 0.89 (t, 3H); $^{13}$C NMR (CDCl$_3$, 400 MHz) δ 179.6, 144.2, 129.6, 127.9, 126.8, 68.2, 47.3, 32.7, 29.3, 22.1, 13.7; MS (FAB-/LR/NBA) 389.0.

EXAMPLE 15

4-Methyl-2-tritylsulfanyl-pentanoic acid

MS (thio FAB) 389.

EXAMPLE 16

3-Methyl-2-tritylsulfanyl-butyric acid

MS (FAB-/LR/NBA) 375.1.

EXAMPLE 17

3,3-Dimethyl-2-tritylsulfanyl-butyric acid $^1$H NMR (CDCl$_3$, 400 MHz) δ 11.59 (br s, 1H), 7.56 (d, 6H), 7.33–7.18 (m, 9H), 2.62 (s, 1H), 0.97 (s, 9H); MS (FAB-/NBA) 389.1.

EXAMPLE 18

3-tert-Butoxy-2-tritylsulfanyl-propionic acid $^1$H NMR (CDCl$_3$, 400 MHz) δ 7.49 (d, 6H), 7.32–7.21 (m, 9H), 3.26 (t, 1H), 3.16 (dd, 1H), 2.83 (dd, 1H), 1.02 (s, 9H); MS (MAB/HR/N2) 420.1755 HRMS calcd for $C_{26}H_{28}O_3S$ 420.175917. found 420.175534.

EXAMPLE 19

3-tert-Butoxy-2-tritylsulfanyl-butyric acid $^1$H NMR (CDCl$_3$, 400 MHz) δ 7.54–7.47 (m 6H), 7.33–7.20 (m, 9H), 3.23 (m,1H), 2.96 (d, 1H), 1.19 (s, 9H), 0.99 (m, 3H); $^{13}$C NMR (CDCl$_3$, 400 MHz) δ 172.4, 143.9, 129.5, 127.9, 126.8, 69.3, 68.6, 53.7, 28.5, 28.4, 21.2; MS (FAB-/LR/NBA) 432.9.

EXAMPLE 20

3-(2-Carboxy-2-tritylsulfanyl-ethyl)-indole-1-carboxylic acid tert-butyl ester.

$^1$H NMR (CDCl3, 400 MHz) δ 7.45–7.12 (m, 20H), 3.27 (dd, 1H), 3.14 (dd, 1H), 2.67 (dd, 1H), 1.65 (s, 9H); $^{13}$C NMR (CDCl$_3$, 400 MHz) δ 178.1, 149.4, 143.9, 129.5, 127.8, 126.8, 124.3, 124.2, 122.3, 118.8, 116.3, 115.0, 83.5, 68.5, 60.3, 47.4, 28.6, 28.1; MS (FAB-/NBA) 562.0.

EXAMPLE 21

2-Ethoxycarbonyl-succinic acid 4-tert-butyl ester 1-ethyl ester

Diethyl malonate (31.15 g, 194.48 mmoles) was first transferred at 0° C. to a stirring suspension of sodium hydride (4.67 g, 194.58 mmoles) in dry THF (200 mL). To this resulting mixture, was added dropwise (at 0° C.) a solution of t-butyl bromoacetate (23.00 g, 117.91 mmoles). Formation of a white precipitate was instantly observed. The mixture was then stirred at room temperature until complete consumption of the starting material (1.5 hours as confirmed by TLC: 20% ethyl acetate:80% hexanes). The solvent was then evaporated and the residue was taken-up in 500 mL diethyl ether. This organic phase was washed with water (3×300 mL) and washed once with brine (200 mL) before being dried (anhydrous MgSO$_4$) and evaporated. The obtained residue was first purified by distillation to remove excess malonate and then by flash chromatography (SiO$_2$, 15% ethyl acetate:85% hexanes) to afford 30.00 g (92.8% yield) of the desired compound as an oil: IR (film) 2982, 1733, 1258, 1152, 1037 cm$^{-1}$; $^{13}$C NMR (CDCl$_3$, 100 MHz) 169.5, 168.1, 80.8, 61.2, 47.7, 33.9, 27.6.

EXAMPLE 22

2-Carboxy-succinic acid 4-tert-butyl ester

To a stirring solution of the compound of example 21 (20.00 g, 72.91 mmoles) in ethanol (250 mL) was added a 10% aqueous solution of potassium hydroxide (9.65 g, 172.07 mmoles). The resulting mixture was then stirred at reflux for eight hours. When the reaction was completed (as confirmed by TLC: 20% ethyl acetate:80% hexanes), the mixture was first cooled down and the solvent was evaporated. The obtained residue was taken-up in water (200 mL) and washed with diethyl ether (2×200 mL) before being acidified with a 10% aqueous solution of hydrochloric acid. The product was then extracted from the aqueous phase with ethyl acetate (4×200 mL). The organic layers were combined, dried (anhydrous MgSO$_4$), filtered and evaporated under vacuum to yield 13.30 g (83.6% yield) of the desired diacid as an oil. This product was used directly in the next reaction without further purification: $^1$H NMR (CDCl$_3$, 400 MHz) 11.11 (br s, 2H), 3.81 (t, 1H), 2.87 (d, 2H), 1.40 (s, 9H); $^{13}$C NMR (CDCl$_3$, 100 MHz) 173.0, 169.7, 81.9, 47.3, 33.9, 27.7.

EXAMPLE 23

2-Methylene-succinic acid 4-tert-butyl ester

To a stirring solution of the compound of example 22 (13.30 g, 60.95 mmoles) in ethanol (500 mL) at 0° C. were sequentially added diethylamine (11.17 g, 152.72 mmoles) and a 37% aqueous solution of formaldehyde (4.57 g, 152.18 mmoles). The resulting mixture was stirred at room temperature for 12 hours. The solvent was then directly evaporated under vacuum and the obtained residue was dissolved in a saturated aqueous solution of sodium bicarbonate (400 mL). The aqueous phase was twice washed with ethyl acetate and then acidified with a 10% aqueous solution of hydrochloric acid. The aqueous layer was extracted with ethyl acetate (4×400 mL) to afford, after concentration, 3.00 g (26.4% yield) of the desired decarboxylated product. This compound was used directly in the next reaction without further purification: $^1$H NMR (CDCl$_3$, 400 MHz) δ 6.41 (s, 1H), 5.78 (s, 1H), 3.25 (s, 2H), 1.43 (s, 9H); $^{13}$C NMR (CDCl$_3$, 300 MHz) δ 171.6, 169.8, 133.6, 130.1, 81.2, 38.5, 27.8.

EXAMPLE 24

2-Acetylsulfanylmethyl-succinic acid 4-tert-butyl ester

To a stirring solution of the compound of example 23 (3.00 g, 16.11 mmoles) in anhydrous THF (16 mL), was added drop wise thiolacetic acid (3.68 g, 48.34 mmoles). The mixture was stirred at room temperature for 24 hours. The solvent was then evaporated under vacuum and the residue was directly purified by flash chromatography (SiO$_2$, 20% ethyl acetate:80% hexanes) to afford 1.80 g (42.6% yield) of the desired product as a yellow oil. IR (film) 2980, 2652, 1729, 1255, 1152 cm$^{-1}$; HRMS (EI) Calcd for C$_{11}$H$_{19}$O$_5$S: 263.0953. Found: 263.0944.

EXAMPLE 25

2-Mercaptomethyl-succinic acid 4-tert-butyl ester

To a stirring solution of the crude compound of example 24 (6.87 g; 26.19 mmoles) in degassed methanol (270 mL) at room temperature was added drop wise a 10% aqueous solution of potassium carbonate (7.24 g; 52.38 mmoles). The mixture was stirred for three hours at room temperature. After complete consumption of the starting material (as confirmed by TLC: 30% ethyl acetate-70% hexanes), the reaction mixture was poured into degassed water (500 mL) and was extracted with degassed dichloromethane (2×200 mL) and then was acidified with a 10% aqueous hydrochloric acid solution. The aqueous layer was finally extracted with ethyl acetate (4×500 mL). The organic extracts were combined, dried (anhydrous MgSO$_4$), filtered and evaporated to yield 8.10 g of the crude desired compound. This residue was used directly in the next step without any further purification.

EXAMPLE 26

2-Tritylsulfanylmethyl-succinic acid 4-tert-butyl ester

To a stirring solution of the compound of example 25 (8.10 g; 36.77 mmoles) in dry THF (25 mL) at room temperature, was transferred dropwise a solution of triphenylmethyl chloride (12.30 g; 44.13 mmoles) in dry THF (25 mL). The mixture was stirred at room temperature for 24 hours. The solvent was then evaporated under vacuum and the residue was directly subjected to flash chromatography (SiO$_2$, gradient of 15% ethyl acetate in hexanes to 50% ethyl acetate in hexanes) to give 3.50 g (20.6% yield) of the pure desired protected compound: $^1$H NMR (CDCl$_3$, 400 MHz) δ 7.50 (d, 6H), 7.29 (m, 9H), 2.58 (m, 5H), 1.45 (S, 9H); $^{13}$C NMR (CDCl$_3$, 100 MHz) δ 179.31, 170.32, 144.34, 129.47, 127.93, 127.81, 126.75, 81.03, 66.93, 40.73, 36.13, 32.66, 27.90.

EXAMPLE 27

5-Tritylsulfany-pentanoic acid ethyl ester

To a suspension of sodium hydride (989 mg, 24.47 mmol) in anhydrous DMF (60 mL) was added portion wise triphenylmethanethiol. After 15 minutes of stirring, ethyl 5-bromovalerate (2.8 mL, 17.48 mmol) was injected and the mixture was stirred at ambient conditions for 24 h. The reaction mixture was portioned between ether and saturated ammonium chloride. The water phase was extracted several times with ether. The recombined organic layer was washed with brine, dried, filtered and evaporated. The crude was flashed using 5–10% ethyl acetate in hexanes. $^1$H-NMR (CDCl$_3$, 400 MHz): 1.23(t, J=7.0 Hz, 3H); 1.42(m, 2H); 1.59(m, 2H); 2.16(m, 4H); 4.09(q, J=7.0 Hz, 2H), 7.21–7.30, 7.42(m, 15H).

EXAMPLE 28

2-(3-Tritylsulfanyl-propyl)-succinic acid 4-tert-butyl ester 1-ethyl ester

To a solution of LDA (2M, 9.1 mL, 18.17 mmol) at −70° C. was added HMPA(10 mL) followed by the drop wise addition of a solution of the compound of example 27 (6.12 g, 15.14 mmol) in anhydrous THF (10 mL). The reaction mixture was allowed to warm up to −40° C. and was stirred for another 30 minutes, after which, a solution of tert-butyl bromoacetate (2.5 mL, 16.65 mmol) in anhydrous THF (10 mL) was added. The reaction mixture was stirred for 1 h at the same temperature and then allowed to warm up to room temperature followed by stirring for 24 h. The reaction mixture was portioned between ether and saturated ammonium chloride. The water phase was extracted several times with ether. The recombined organic layer was washed with brine, dried, filtered and evaporated. Silica gel chromatography using 5% ethyl acetate in hexanes provided the product as a light yellow oil. $^1$H-NMR(CDCl$_3$, 400 MHz: 1.24(t, J=7.1 Hz, 3H); 1.43(s, 9H); 1.40–1.57(m, 4H); 2.15 (m, 2H); 2.24(m, 1H); 2.58(m, 2H); 4.12(q, J=7.1 Hz, 2H), 7.19–7.23, 7.26–7.30, 7.41(m, 15H).

EXAMPLE 29

2-(3-Tritylsulfanyl-propyl)-succinic acid 4-tert-butyl ester

To a solution of the compound of example 28 (3.00 g, 5.78 mmol) in methanol (30 mL) and water (10 mL) was added NaOH (1N, 11.6 mL, 11.6 mmol). The mixture was stirred vigorously under ambient conditions. After 24 hours, most of the methanol has evaporated. The residue was portioned between water and ether. The water phase was extracted two times with ether, then acidified with HCl (1N) to pH 1. The water phase was extracted three times with ethyl acetate. The recombined organic phase was dried over sodium sulfate, filtered, and evaporated. The residue was flashed using 5% methanol in chloroform to give the product as a white solid. $^1$H-NMR(CDCl$_3$, 400 MHz: 1.45(s, 9H); 1.35–1.64(m, 4H); 1.58(m, 1H); 2.16(m, 2H); 2.26(m, 1H); 2.64(m, 1H); 4.12(q, J=7.1 Hz, 2H), 7.19–7.29, 7.40(m, 15H).

EXAMPLE 30

2-Hydroxymethyl-acrylic acid ethyl ester

To a mixture of triethylphosphonoacetate (44.80 g, 0.20 mol) and a 37% aqueous solution of formaldehyde (59.95 mL, 0.80 mol) stirred at room temperature was slowly added a saturated solution of potassium carbonate (48.4 g, 0.35 mol). At the end of the addition, the temperature reached 30–35° C. and stirring was continued for an additional 2 hours. The mixture was extracted with ether (3×100 ml) and the combined organic extracts were dried (anhydrous MgSO$_4$) and the solvent was evaporated in vacuo. The remaining oil was purified by flash chromatography (SiO$_2$, 15% ethyl acetate–85% hexanes) to afford 18.42 g (70.8%) of the desired compound as an oil: $^1$H NMR (CDCl$_3$, 400 MHz) δ 1.19 (t, 3H), 3.50 (s, 1H), 8.85 (q, 2H), 5.7, 6.31 (s, 1H); $^{13}$C NMR (CDCl$_3$, 400 MHz) ☐166.7, 140.1, 125.3, 61.1, 53.9, 14.4.

EXAMPLE 31

2-Bromomethyl-acrylic acid ethyl ester

Phosphorus tribromide (17.16 g, 63.41 mmol) was added to a stirred solution of the compound of example 30 (17.92 g, 138.1 mmol) in dry ether (132 mL) at −10° C. The temperature was allowed to rise to 20° C. and stirring was continued for 3h. Water (80 mL) was then added at −10° C. and the mixture was extracted with hexane (3×45 mL). The organic extracts were washed with saturated sodium chloride solution (2×45 mL) and dried with anhydrous MgSO$_4$. Evaporation of solvent under vacuum gave 15.07 g (yield 56.6%) of the crude product, which was used directly in the next reaction without any further purification. $^1$H NMR (CDCl$_3$, 400 MHz) δ 6.25 (s, 1H), 5.88 (s, 1H), 4.2 (q, 2H), 4.11 (s, 2H), 1.25 (t, 3H); $^{13}$C NMR (CDCl$_3$, 400 MHz) ☐166.7, 140.1, 125.3, 61.1, 53.9, 14.4.

EXAMPLE 32

2-tert-Butoxycarbonyl-4-methylene-pentanedioic acid 1-tert-butyl ester 5-ethyl ester Di-tert-butylmalonate (14.95 g, 77.50 mmol) was transferred at 0° C. to a suspension of sodium hydride (3.1 g, 77.50 mmol) in dry THF (78 mL). To this resulting mixture was added dropwise at 0° C., a solution of the compound of example 31 (14.96 g, 77.50 mmol) in dry THF (78 mL). The mixture was then stirred at room temperature until complete consumption of the starting material (30 minutes as confirmed by TLC: 15% hexane-85% ethyl acetate). The solvent was then evaporated and the residue was taken-up into 400 mL of water followed by extraction with ether (4×300 ml). The organic extracts were combined and washed with brine. Drying and evaporation of the solvent gave the crude product. Purification by flash chromatography (SiO$_2$, 10% hexane-90% ethyl acetate) afforded 22.62 g (89% yield) of the desired compound as an oil: $^1$H NMR (CDCl$_3$, 300 MHz) δ 6.21 (s, 1H, CH), 5.62 (s, 1H), 4.25 (q, 2H), 3.51 (t, 1H), 2.83 (d, 2H), 1.45 (s, 18H), 1.31 (t, 3H).

EXAMPLE 33

2-tert-Butoxycarbonyl-4-tritylsulfanylmethyl-pentanedioic acid 1-tert-butyl ester 5-ethyl ester Triphenylmethanethiol (20.58 g, 74.5 mmol) in dry THF (40 mL) was first added drop wise at 0° C. to a suspension of sodium hydride (3.00 g, 74.5 mmol) in dry THF (60 mL). After the addition was complete, the mixture was stirred for 15 min at 0° C. followed by 45 minutes at room temperature. To the resulting suspension, the compound of example 32 (20.58 g, 62.4 mmol) dissolved in dry THF (40 ml) was added drop wise at 0° C. The mixture was then stirred at room temperature until complete consumption of the starting material (2 hours as confirmed by TLC: 97% hexane-3% ethyl acetate). The crude product was isolated as in example 32 and was then purified by flash chromatography (SiO$_2$, 5% hexane-95% ethyl acetate) to afford 28.28 g (75.5% yield) of the desired compound as an oil: $^1$H NMR (CDCl$_3$, 400 MHz) δ 7.31 (m, 15H), 4.17 (q, 2H), 3.03 (m, 1H), 2.49 (m, 1H), 2.42 (m, 1H), 2.31 (m, 2H), 2.21 (m, 1H), 1.44 (s, 18H), 1.29 (t, 3H); $^{13}$C NMR (CDCl$_3$, 400 MHz) ☐176.3, 167.9, 144.4, 129.4, 127.7, 126.5, 81.5, 66.6, 60.6, 51.4, 42.6, 33.6, 30.4, 27.7, 14.1.

EXAMPLE 34

2-tert-Butoxycarbonyl-4-tritylsulfanylmethyl-pentanedioic acid 1-tert-butyl ester To a stirred solution of the ester of example 33 (2.1 g, 3.31 mmol) in ethanol (11 mL) was added 17.4 ml of a 10% aqueous solution of potassium hydroxide. The resulting mixture was stirred for 24 hours. After evaporation of the solvent, the obtained residue was taken-up into 50 ml of water and washed with diethyl ether (2×50 mL). The aqueous layer was then acidified to pH 3 with a 10% aqueous solution of hydrochloric acid at 0° C. and immediately extracted with ethyl acetate (5×50 ml). The organic extracts were combined, washed with water, and dried over anhydrous magnesium sulfate. Evaporation under vacuum gave the crude product which was purified by flash chromatography (SiO$_2$, 70% hexane-30% ethyl acetate) to afford 880 mg of the desired compound: $^1$H NMR (CDCl$_3$, 400 MHz) δ 7.31 (m, 15H), 3.04 (t, 1H), 2.95 (m, 1H), 2.25 (m, 2H), 1.85 (m, 1H), 1.44 (s, 18H); $^{13}$C NMR (CDCl$_3$, 400 MHz) ☐173.9, 168.5, 144.9, 129.7, 128.3, 128.0, 82.0, 51.9, 43.3, 33.7, 30,5, 27.2.

EXAMPLE 35

2-(3',4'-Dimethoxy-biphenyl-4-yl)-ethylamine

To a solution of 4-bromophenethylamine (10 g, 48.98 mmol) in anhydrous DMF (150 mL), containing anhydrous triethylamine (35 mL, 244.9 mol), was added Boc$_2$O. The reaction mixture was heated for 15 minutes at 50° C. After cooling to room temperature, brine (100 mL) and HCl (1N, 100 mL) were added subsequently, and the mixture was extracted several times with ether. The recombined organic layer was washed again with brine, dried over sodium sulfate, filtered and evaporated. The crude was flashed with 10% ethyl acetate in hexanes to give the [2-(4-bromo-phenyl)-ethyl]-carbamic acid tert-butyl ester. $^1$H NMR (CDCl$_3$, 300 MHz: 1.41(s, 9H); 2.22(t, J=7.1 Hz, 2H); 3.31(m, 2H); 4.67(s, broad, 1H); 7.03(d, J=8.2 Hz, 2H); 7.38(d, J=8.2 Hz, 2H).

A mixture of the above mentioned compound (1.00 g, 3.33 mmol), 3,4-dimethoxyphenylboronic acid (1.21 g, 6.66 mmol), and potassium hydroxide (2N, 5 mL, 10 mmol) in THF (15 mL) was degassed using argon for 5 minutes. Palladium tetrakis-triphenylphosphine (200 mg, 0.167 mmol) was added and the mixture was heated at 85° C. After 24 hours, the reaction mixture was allowed to cool to room temperature. Brine (20 mL) was added and the reaction mixture was extracted several times with ether. The recombined organic phase was extracted with brine, dried over sodium sulfate, filtered, and evaporated. Silica gel chromatography of the crude using 20% ethyl acetate/n-hexane afforded [2-(3',4'-Dimethoxy-biphenyl-4yl)-ethylamine]-carbamic acid tert-butyl ester as a white solid. $^1$H-NMR (CDCl$_3$, 300 MHz: 1.44(s, 9H); 2.82(t, J=6.9 Hz, 2H); 3.39(m, 2H); 3.91(s, 3H); 3.93(s, 3H); 4.67(s, broad, 1H); 6.92(d, J=8.2 Hz, 1H); 7.11(m, 2H); 7.25(m, 2H); 7.48(d, J=8.1 Hz, 2H).

A solution of the above mentioned compound (1.14 g, 3.19 mmol) in anhydrous methanol (50 mL) was cooled in ice bath and then treated drop wise with acetyl chloride. Stirring was continued for 30 minutes at the same temperature followed by overnight stirring at room temperature. About 30 mL of the solvent was removed by evaporation and the mixture was diluted with 200 mL of ether. The entitled product was collected as a white solid by filtration, followed by washing with anhydrous ether and drying under high vacuum. $^1$H-NMR (D$_2$O, 300 MHz: 2.80(t, J=6.9 Hz, 2H); 3.40(m, 2H); 3.91(s, 3H); 3.93(s, 3H); 4.77(s, broad, 1H); 7.00(d, J=8.2 Hz, 1H); 7.15(m, 2H); 7.26(m, 2H); 7.50(d, J=8.1 Hz, 2H).

The amines of examples 36–42 were prepared by the Suzuki cross coupling method as illustrated above in example 35.

EXAMPLE 36

4'-(2-Amino-ethyl)-biphenyl-4-carbonitrile

EXAMPLE 37

2-(4-Pyridin-2-yl-phenyl)-ethylamine

EXAMPLE 38

(4'-(2-Amino-ethyl)-biphenyl-4-ol

Example 39

[4'-(2-Amino-ethyl)-biphenyl-4-yl]-dimethyl-amine

EXAMPLE 40

2-(3',4'-Dimethoxy-biphenyl-4yl)-ethylamine

EXAMPLE 41

2-(4'-Phenoxy-biphenyl-4-yl)-ethylamine

EXAMPLE 42

2-(4'-Methoxy-biphenyl-4-yl)-ethylamine

The following amines were prepared by reduction of the corresponding commercially available nitrites:

EXAMPLE 43

2-Naphthalen-1-yl-ethylamine

EXAMPLE 44

2-Naphthalen-2-yl-ethylamine

EXAMPLE 45

2-(3-Phenoxy-phenyl)-ethylamine

EXAMPLE 46

2,2-Diphenyl-ethylamine

EXAMPLE 47

4-Phenyl-butyric acid methyl ester

A solution of 4-phenyl-butyric acid (10 g, 60.29 mmol) in methanol (200 mL) was prepared. To this solution was added hafnium chloride-THF complex (0.6 g, 1.2 mmol) and the mixture was stirred overnight at room temperature. The solvent was evaporated and the residue was partitioned between water and diethyl ether. The aqueous phase was extracted again with ether. The recombined organic layer was extracted with saturated sodium hydrogen carbonate, brine, and water. The solvent was evaporated to dryness, after drying over sodium sulfate and filtration. The resultant oily product was used directly in the next reaction without any further purification. $^1$H-NMR (CDCl$_3$, 300 MHz: 1.97 (p, J=7.5 Hz, 2H); 2.35(3, J=7.4 Hz, 2H); 2.66(t, J=7.4 Hz, 2H); 3.67(s, 3H); 7.22(m, 5H).

EXAMPLE 48

2-Phenethyl-succinic acid 4-tert-butyl ester 1-methyl ester

A solution of 4-phenyl-butyric acid methyl ester (compound of example 47) (5 g, 28.05 mmol) in anhydrous THF (200 mL) was prepared and cooled to −78° C. To this solution was added by cannula a freshly prepared solution of LDA (28.05 mmol, ca. 1M) in anhydrous THF. The reaction mixture was stirred for 30 minutes, then treated drop wise with a cooled solution of tert-butyl bromoacetate (4.6 mL, 30.86 mmol) in anhydrous THF (30 mL). HMPA (1.2 mL) was added and stirring was continued at −78° C. for an additional 30 minutes followed by slowly warming to room temperature. Stirring was continued overnight. Saturated ammonium chloride was added and after stirring, the organic phase was separated. The aqueous phase was extracted several times with ethyl acetate. The recombined organic layer was washed with brine, dried over sodium sulfate and filtered. The solvent was evaporated and the crude product was flashed using 10% ethyl acetate in hexanes. Based on its $^1$H NMR spectrum, the flashed oily colorless product was considered sufficiently pure for the next step. $^1$H-NMR (CDCl$_3$, 300 MHz: 1.43(s, 9H); 1.99(m, 2H); 2.40(m, 1H); 2.73(m, 4H); 2.84(m, 1H); 3.71(s, 3H); 7.21(m, 5H).

EXAMPLE 49

2-Phenethyl-succinic acid 1-methyl ester

A solution of the compound of example 48 in dichloromethane (20 mL) and containing about 1 mL of water was prepared. The solution was cooled in an ice bath and treated with TFA (10 mL). The reaction mixture was stirred for 1 hour while in the ice bath, followed by 1 hour at room temperature. The solvent was evaporated and the residue was partitioned between water and dichloromethane. The aqueous phase was extracted twice with dichloromethane. The recombined organic layer was washed with brine, dried over sodium sulfate, filtered and evaporated. The crude oil was flashed using 10% ethyl acetate in hexanes followed by 2% methanol in chloroform to give the product as a colorless oil. $^1$H-NMR(CDCl$_3$, 300 MHz: 1.92(m, 2H); 3.70 (s, 3H); 2.62(m, 4H); 2.87(m, 1H); 3.72(s, 3H).

EXAMPLE 50

4-(4-Benzyl-2-oxo-oxazolidin-3-yl)-4-oxo-2-phenethyl-butyric acid methyl ester To a solution of the compound of example 49 (2.51 g, 10.62 mmol) in anhydrous THF (60 mL) and containing triethyl amine (1.8 mL, 12.74 mmol) at −70° C. was added drop wise trimethylacetyl chloride. After 15 minutes, the reaction mixture was placed in an ice bath and stirred for 45 minutes after which time, the reaction mixture was cooled to −78° C. In a separate flask, n-butyl lithium (2.5M in hexanes, 43 mL, 10.62 mmol) was added to a solution of R-4-benzyl-2-oxazolidinone in anhydrous THF at −78° C. After 15 minutes of stirring, this mixture was transferred by cannula to the former solution. The resultant mixture was stirred for 20 minutes at −78° C. followed by an additional 2 h in an ice bath. The reaction was quenched by the addition of a saturated solution of ammonium chloride. The mixture was extracted several times using ethyl acetate. The recombined organic layer was extracted with brine, saturated sodium hydrogen carbonate, brine, and water, respectively. The solvent was evaporated following drying over sodium sulfate and filtration. The resultant crude material was flashed using 30% ethyl acetate in hexanes to give the product as a white solid. $^1$H-NMR(CDCl$_3$, 300 MHz: 1.89 (m, 1H); 2.05(m, 1H); 2.75(m, 3H); 3.00(m, 1H); 3.68(m, 3H); 3.75(s, 3H); 4.18(m, 2H); 4.65(m, 1H); 7.21(m, 5H), 7.33(m, 5H).

EXAMPLE 51

3-(4-Benzyl-2-oxo-oxazolidine-3-carbonyl)-2-phenethyl-pentanedioic acid 5-tert-butyl ester 1-methyl ester A solution of the compound of example 50 (2.40 g, 6.07 mmol) in anhydrous THF (60 mL) was cooled to −78° C. A solution of NaHDMS in THF (1M, 6.7 mmol, 6.7 mL) was injected over 10 minutes. The reaction mixture was stirred for an additional 20 minutes, after which time, a solution of tert-butyl bromoacetate in anhydrous THF (5 mL) was slowly injected. After stirring for 1 h at −78° C., and 3 h at −48° C., the reaction was quenched by the addition of a saturated ammonium chloride solution. The mixture was extracted several times using ethyl acetate. The recombined organic layer was extracted successively with brine, saturated sodium hydrogen carbonate, brine and water. The solvent was evaporated following drying over sodium sulfate and filtration. The resultant crude material was flashed using 20% ethyl acetate in hexanes to give the product as a white solid. $^1$H-NMR(CDCl$_3$, 300 MHz: 1.40, 1.41(2s, 9H); 1.74–1.92(m, 5H); 2.45–2.95(m, 4H); 3.31(m, 1H); 3.69, 3.73(2 s, 3H); 4.11(m, 2H); 4.50, 4.66(2 m, 1H); 7.25(m, 10H).

EXAMPLE 52

3-Benzyloxycarbonyl-2-phenethyl-pentanedioic acid 5-tert-butyl ester 1-methyl ester To a stirred solution of benzyl alcohol (0.5 mL, 4.41 mmol) in anhydrous THF (16 mL) at −70° C., was added n-butyl lithium (2.5M, 1.4 mL, 3.53 mmol). After 10 minutes of stirring, the solution was transferred by means of a cannula to a solution of the compound of example 51 in anhydrous THF (15 mL) at −70° C. The reaction was allowed to warm to −10° C. over a period of 2 h, after which time, it was placed in an ice bath and stirred for another 50 minutes. Finally, the reaction was quenched by the addition of a saturated ammonium chloride solution. The mixture was extracted several times using ethyl acetate. The recombined organic layer was extracted with brine, dried over sodium sulfate, filtered and evaporated. The resultant crude was flashed using 10% ethyl acetate in hexanes to give the product as a colorless oil. $^1$H-NMR(CDCl$_3$, 300 MHz: 1.39, 1.40(2 s, 9H); 1.70(m, 1H); 2.01(m, 1H); 2.31–2.74(m, 4H); 2.83(m, 1H); 3.21(m, 1H); 3.61, 3.64(2s, 3H); 5.11(m, 2H); 7.08–7.35(m, 10H).

EXAMPLE 53

3-Carboxy-2-phenethyl-pentandioic acid 5-tert-butyl ester 1-methyl ester

A solution of the compound of example 52 (700 mg, 1.59 mmol) in ethanol (95%, 100 mL) was hydrogenated in the presence of a catalytic amount palladium (10% on charcoal). After 24 h of stirring, the reaction was complete. The mixture was filtered over a celite pad and the solvent was evaporated. The residue was distributed between ethyl acetate and water. The aqueous phase was extracted twice more with ethyl acetate. The recombined organic layer was washed with brine, dried over sodium sulfate, filtered, and evaporated.

EXAMPLE 54

3-(2-Biphenyl-4-yl-ethylcarbamoyl)-2-phenethyl-pentanedioic acid 5-tertbutyl ester 1-methyl ester A solution of the compound of example 53 (590 mg, 1.68 mmol) and HOBt (272 mg, 2.016 mmol) in anhydrous DMF was stirred in an ice bath for 10 minutes. Biphenyl ethylamine (404 mg, 2.02 mmol) was added followed by the addition of DIC (320 μL, 2.01 mmol). After 20 minutes, the ice bath was removed and stirring was continued at room temperature. After 24 h of stirring, the reaction mixture was partitioned between ethyl acetate and HCl (1M, excess). The aqueous phase was extracted several times with ethyl acetate. The recombined organic layer was extracted with brine, saturated sodium hydrogen carbonate, and brine. The solvent was evaporated following drying over sodium sulfate and filtration. The crude was flashed using 25% EtOAc in hexanes. $^1$H-NMR(CDCl$_3$, 300 MHz: 1.41(s, 9H); 1.82 (m, 2H); 2.23(m, 1H); 2.55(t, J=8.1 Hz, 2H); 2.75(m, 5H); 3.54(m, 1H); 3.70(s, 3H); 6.09(t, J=5.7 Hz, 1H); 7.13–7.36, 7.41–7.49, 7.55–7.58(m, 14H).

EXAMPLE 55

3-(Biphenyl-4-yl-ethylcarbamoyl)-2-phenethyl-pentanedioic acid 5-tert-butyl ester A solution of the compound of example 54 (344 mg, 0.65 mmol) in methanol was placed in an ice bath and treated slowly with a solution of sodium hydroxide (1N, 1.3 mL, 1.3 mmol). After finishing the addition, the reaction mixture was stirred for 24 h at room temperature. The solvent was removed and the residue was portioned between ether and water. After separation, the aqueous phase was acidified using HCl (1N) to pH 1 and extracted three times with ethyl acetate. The recombined organic phase was dried over sodium sulfate, filtered, and evaporated to give the product as colorless oil.

EXAMPLE 56

N-[1-tert-Butoxycarbonyl-2-(1H-indol-3-yl)-ethyl]-3-(9H-fluoren-9-ylmethoxycarbonylamino)-succinamic acid tert-butyl ester To H-Trp-OBut (2.00 g, 6.75 mmol) in DMF (50 mL) was added sequentially Fmoc-Asp(OBut)-OH (2.78 g, 6.75 mmol), HOBt (0.91 g, 6.75 mmol), BOP (2.99 g, 6.75 mmol) and DIPEA (2.35 mL, 13.50 mmol) at room temperature. The mixture was stirred for 2 h at room temperature. The reaction mixture was then diluted with ethyl acetate (300 mL) and washed with diluted KHSO$_4$ (5%), NaHCO$_3$ (5%), H$_2$O, and brine. Drying (Na$_2$SO$_4$) and concentration under vacuum gave the title dipeptide, 4.2 g (97%), as a white foam which was pure as indicated by its spectroscopic data: $^1$H NMR (CDCl$_3$, 300 MHz) d 7.90 (br s, 1H), 7.71 (br d, 2H), 7.57 (br d, 1H), 7.50 (t, 1H), 7.49–7.0 (m, 8H), 5.80 (d, 1H), 4.7 (q, 1H), 4.61–4.02 (m, 4H), 3.22 (m, 2H), 2.8 (dd, 1H), 2.55 (dd, 1H), 1.39 (s, 9H), 1.27 (s, 9H); $^{13}$C NMR (CDCl$_3$, 75 MHz) d 170.2, 169.8, 143.6, 141.1, 135.8, 127.6, 127.5, 127.0, 125.0, 122.6, 122.0, 119.9, 119.3, 118.8, 110.9, 110.1, 81.9, 81.6, 67.1, 60.3, 53.5, 50.9, 46.9, 27.9, 27.7, 27.3, 14.1; MS (PosFAB) 653, 654 (MH)+.

EXAMPLE 57

3-Amino-N-[1-tert-butoxycarbonyl-2-(1H-indol-3-yl)-ethyl]-succinamic acid tert-butyl ester This compound was prepared by Fmoc deprotection of the compound of Example 56 using diethylamine in dichloromethane. Isolation by flash chromatography gave the title compound (73%): $^1$H NMR (CDCl$_3$, 300 MHz) d 8.42 (br s, 1H), 7.88 (d, 1H), 7.62 (d, 1H), 7.42–7.11 (m, 3H), 4.81 (dt, 1H), 3.57 (dd, 1H), 3.32 (m, 2H), 2.70 (dd, 1H), 2.32 (dd, 1H), 1.43 (s, 9H), 1.38 (s, 9H).

EXAMPLE 58

2-Ethoxycarbonyl-succinic acid 4-tert-butyl ester

To the tri-ester of example 21 (38 g, 0.14 mol) in ethanol (456 mL) was added 77.6 mL of a 10% aqueous solution of potassium hydroxide. The resulting mixture was refluxed for 3 hours. The isolated product was purified by flash chromatography (SiO$_2$, 90% dichloromethane-10% methanol) to afford 20.68 g (60.6% yield) of the title compound: $^1$H NMR (CDCl$_3$, 400 MHz) 4.16 (q, 2H), 3.72 (t, 1H), 2.80 (d, 2H), 1.35 (s, 9H), 1.20 (t, 3H); $^{13}$C NMR (CDCl$_3$, 400 MHz) 170.0, 168.9, 81.6, 62.4, 47.7, 34.5, 28.2, 14.5.

EXAMPLE 59

2-tert-Butoxycarbamoyl-succinic acid 4-tert-butyl ester 1-ethyl ester

To a stirring solution of O-tert-butyl hydroxylamine hydrochloride (3.67 g, 29.3 mmol) in dry THF (30 mL) at room temperature was added diisopropylethyl amine (3.60 g, 27.9 mmol). To the resulting mixture was transferred the compound of example 58 (6.87 g, 27.9 mmol), as a solution in dry THF (30 mL), followed by HOBt (5.35 g, 27.9 mmol). The mixture was cooled to 0° C. and EDC (5.35 g, 27.9 mmol) was added in one portion. The reaction mixture was then allowed to warm to room temperature and was stirred for 24 h. The solvent was evaporated and the residue was taken-up into 500 ml of ethyl acetate and subsequently washed with a 5% aqueous solution of KHSO$_4$ (2×200 mL), with a 5% aqueous solution of NaHCO$_3$ (2×200 mL), and finally with water. After drying (anhydrous MgSO$_4$) and evaporation, the crude product was purified by flash chromatography (SiO$_2$, 60% hexane-40% ethyl acetate) to afford 5.93 g (66.0% yield) of the desired product: $^1$H NMR (CDCl$_3$, 400 MHz) 8.61 (s, 1H), 4.20 (q, 2H), 3.55 (t, 1H), 2.93 (d, 3H), 1.43 (s, 9H), 1.28 (s, 9H); $^{13}$C NMR (CDCl$_3$, 400 MHz) 195.8, 171.2, 169.7, 83.1, 81.9, 62.4, 46.8, 34.1, 28.4, 26.6, 14.5.

EXAMPLE 60

2-tert-Butoxycarbamoyl-succinic acid 4-tert-butyl ester

To 2-tert-butoxycarbamoyl-succinic acid 4-tert-butyl ester 1-ethyl ester (5.92 g, 18.6 mmol) in ethanol (224 mL) was added 20.91 mL of a 10% aqueous solution of potassium hydroxide. The resulting mixture was then stirred at room temperature for 3 hours and then worked up. The crude product was purified by flash chromatography (SiO$_2$, 90% dichloromethane-10% methanol) to afford 3.06 g (57.0% yield) of the desired mono acid: 1H NMR (CDCl3, 400 MHz) 3.65 (t, 1H), 2.78 (dd, 3H), 1.45 (s, 9H), 1.25 s, 9H); 13C NMR (CDCl3, 400 MHz) 171.2, 169.7, 84.0, 82.0, 46.8, 34.5, 28.5, 26.5.

EXAMPLE 61

3-Methoxycarbonyl-pentanedioic acid mono-tert-butyl ester

A solution of anhydrous diisopropylamine (22.3 mL, 158.9 mmol) in dry THF (250 mL) was prepared. To this solution at −78° C. was added drop wise n-butyl lithium (2.5 M in n-hexane, 66.6 mL, 166.5 mmol). Stirring was continued at the same temperature for an additional 15 minutes followed by 20 minutes at room temperature. The reaction mixture was next cooled to −78° C. and was transferred via cannula to a solution of succinic acid monomethyl ester (10 g, 75.7 mmol) in dry THF (100 mL) at −78° C. HMPA (3.3 mL, 18.9 mmol) was added, followed, after about 10 minutes, with the slow introduction of a solution of tert-butyl bromoacetate (11.2 mL, 75.7 mmol) in dry THF (100 mL). After 30 minutes at −78° C., the reaction mixture was allowed to warm up and stirring was continued for 48 hours at room temperature. The crude reaction mixture was then distributed between ethyl acetate (500 mL), HCl (1N, excess), and brine (200 mL). The aqueous layer was extracted several times with fresh ethyl acetate. The recombined organic extracts were washed with brine, dried over sodium sulfate, filtered, and evaporated. Purification by flash chromatography (SiO$_2$, 100% CHCl$_3$ to 2% methanol in CHCl$_3$) afforded the product (12.5 g, 67%) as a light yellow oil: $^1$H NMR(CDCl$_3$, 400 MHz) : 3.67 (s, 3H), 3.18 (m, 1H), 2.47–2.82 (m, 4H), 1.49 (s, 9H).

EXAMPLE 62

2-(Trityloxycarbamoyl-methyl) succinic acid 4-tert-butyl ester 1-methyl ester

A solution of the compound of example 61 (10 g, 40.6 mmol) in anhydrous DMF (50 mL) was successively treated with HOBt (5.5 g, 40.6 mmol) and O-trityl hydroxalamine (11.2 g, 40.6 mmol). The reaction mixture was stirred first in an ice bath for 15 minutes and then treated with DIC (6.4 mL, 40.6 mmol). After stirring for 20 minutes, the ice bath was removed and the reaction mixture was stirred for 24 hours at room temperature. The reaction mixture was distributed between ethyl acetate (200 mL) and a mixture of potassium hydrogen sulfate (1N, 45 mL, 1.5 eq) and brine (excess). The aqueous phase was extracted several times with fresh ethyl acetate. The combined organic extracts were washed with brine, sodium hydrogen carbonate (10%, excess), brine, and finally dried over sodium sulfate. Evaporation and then purification by flash chromatography ($SiO_2$, 20% to 30% of ethyl acetate/n-hexane) afforded the product (12.8, 63%) as a white solid: $^1$H NMR ($CDCl_3$, 400 MHz) ☐ 7.71 (d, 1H), 7.31–7.45 (m, 15H), 3.63 (s, 3H), 2.95 (m, 1H), 2.05–2.40 (m, 4H), 1.40 (s, 9H).

EXAMPLE 63

2-(Trityloxycarbamoyl-methyl) succinic acid 4-tert-butyl ester

A solution of the diester of example 62 (10.5 g, 20.8 mmol) in methanol (100 mL) was cooled in an ice bath and was treated drop wise with a solution of sodium hydroxide (1N, 42 mL). Stirring was continued for 30 minutes and then for an additional 48 hours at room temperature. The methanol was evaporated in a rotary evaporator and the alkaline reaction mixture was diluted with water followed by extracting with ether. The pH was adjusted to 4 by the addition of HCl (2N) and the acidic solution was extracted several times with ethyl acetate. The combined organic extracts were washed with brine, dried over sodium sulfate, filtered and evaporated to give the desired product (10.2, 100%) as a white foam: $^1$H NMR ($CDCl_3$, 400 MHz) ☐7.70 (d, 1H), 7.26–7.46 (m, 16H), 2.72–2.99 (m, 1H), 1.99–2.42 (m, 4H), 1.42 (s, 9H).

EXAMPLE 64

3-Methoxycarbonyl-hexanedioic acid 1-tert-butyl ester

To a solution of n-BuLi (2.5M, 2.6 mL, 71.5 mmol) in anhydrous THF (200 mL) was added anhydrous diisopropyl amine (9.6 mL, 68.30 mmol) at –78° C. After 20 minutes of stirring, a solution of monomethyl glutarate (5 g, 32.5 mmol) in anhydrous THF (20 mL) was added drop wise under controlled temperature. After 30 minutes, a solution of tert-butyl bromoacetate (4.9 mL, 32.50 mmol) in anhydrous THF (20 mL) was slowly added followed by the addition of HMPA (8 mL). The reaction mixture was stirred at –78° C. for an additional 2 h followed by 24 h at room temperature. The reaction mixture was partitioned between HCl (2N, excess) and ethyl acetate. The organic phase was separated and the aqueous phase was extracted several times with ethyl acetate. The recombined organic layer was extracted with brine, dried over sodium sulfate, filtered, and evaporated. The residue was first flashed with chloroform and then with 2–5% methanol in chloroform. The product was obtained as a light yellow oil. $^1$H-NMR($CDCl_3$, 400 MHz): 1.42(s, 9H); 1.89(m, 2H); 2.24(m, 2H); 2.64(m, 2H); 2.84 (m, 1H); 3.69(s, 3H).

EXAMPLE 65

2-(2-Trityloxycarbamoyl-ethyl-succinic acid 4-tert-butyl ester 1-methyl ester

To a solution of the compound of example 64 (1.10 g, 4.19 mmol) and HOBt (0.70 g, 5.03 mmol) in DMF (5 mL) were added O-trityl hydroxylamine (1.82 g, 6.28 mmol) and DIC (800 μL), respectively. The reaction mixture was stirred for 24 h at room temperature. The reaction mixture was partitioned between HCl (1N, excess) and ethyl acetate. The aqueous phase was extracted several times with ethyl acetate. The recombined organic layer was washed with brine, saturated sodium bicarbonate, and brine. The solvent was evaporated following drying over sodium sulfate, and the crude was flashed with 20–30% ethyl acetate in hexanes. $^1$H-NMR($CDCl_3$, 400 MHz: 1.42(s, 9H); 1.58, 2.14, 2.47(3 m, 7H); 3.69(s, 3H); 7.34(m, 15H); 7.88(d, broad, 1H).

EXAMPLE 66

2-(2-Trityloxycarbamoyl-ethyl)-succinic acid 4-tert-butyl ester

To a solution of the compound of example 65 (2.27 g, 4.39 mmol) in a mixture of methanol/water (4:1, 50 mL) was added a solution of sodium hydroxide (1N, 9 mL). The resulting mixture was stirred for 24 h at room temperature. The solvent was evaporated and the residue was partitioned between water and ether. The alkaline phase acidified using HCl (6N) and extracted with ethyl acetate followed by drying over sodium sulfate, filtration and evaporation. The product was converted to an off-white foam under high vacuum. $^1$H-NMR($CDCl_3$, 400 MHz: 1.42(s, 9H); 1.59(m, 3H); 1.88–2.54(m, 4H); 7.33(m, 15H); 7.46(s, broad, 1H).

EXAMPLE 67

4-(4-Benzyl-2-oxo-oxazolidin-3-yl)-4-oxo-butyric acid ethyl ester

A solution of R-(+)-4-benzyl-2-oxazolidine (25 g, 144.3 mmol) in anhydrous THF (800 mL) was cooled to –70° C. and treated drop wise with n-BuLi (2.5M in hexanes, 52.5 mL, 131.2 mmol). After 20 minutes of stirring, ethyl 4-chloro-4-oxobutyrate (neat, 23.5 mL, 131.2 mmol) was added drop wise. The reaction mixture was stirred for 15 minutes at –70° C., followed by 1 h in an ice bath. The reaction was quenched by the addition of a saturated ammonium chloride solution. The organic layer was extracted three times with ethyl acetate. The recombined organic layer was extracted with a saturated sodium bicarbonate solution, brine and water. After drying over sodium sulfate and filtration, the solvent was evaporated and the crude product was flashed using 20–40% ethyl acetate/hexanes. The product was obtained as a white solid. $^1$H-NMR($CDCl_3$, 400 MHz: 1.27(t, J=7.1, 3H); 2.71(m, 3H); 3.26(m, 3H); 4.18(m, 4H); 4.6(m, 1H); 7.19–7.36(m 5H).

EXAMPLE 68

4-(4-Benzyl-2-oxo-oxazolidine-3-carbonyl)-pentanedioic acid tert-butyl ester ethyl ester A solution of the compound of example 67 (5.0 g, 16.38 mmol) in anhydrous THF (160 mL) was cooled to −78° C. A solution of NaHDMS in THF (1M, 16.4 mL, 16.4 mmol) was injected over 10 minutes. The reaction mixture was stirred for an additional 20 minutes, after which time, a solution of tert-butyl bromoacetate in anhydrous THF (10 mL) was slowly injected. After stirring for 1 h at −78° C. and 3 h at −48° C., the reaction was quenched by the addition of a saturated ammonium chloride solution. The mixture was extracted several times with ethyl acetate. The recombined organic layer was successively extracted with brine, a saturated sodium hydrogen carbonate solution, brine and water. The solvent was evaporated following drying over sodium sulfate and filtration. The resultant crude product was flashed with 20% ethyl acetate in hexanes to give the product as a white solid. $^1$H-NMR(CDCl$_3$, 400 MHz): 1.24(t, J=7.2, 3H); 1.44(s, 9H); 2.54(m, 2H); 2.77(m, 3H); 3.31(m, 1H); 4.14(m, 4H); 4.43(m, 1H); 4.69(m, 1H); 7.26(m 5H).

EXAMPLE 69

3-Benzyloxycarbonyl-pentandioic acid tert-butyl ester ethyl ester

To a stirred solution of benzyl alcohol (1.3 mL, 12.3 mmol) in anhydrous THF (50 mL) at −70° C., was added n-butyl lithium (2.5M, 4 mL, 10 mmol). After 10 minutes of stirring, the solution was transferred via cannula to a solution of example 65 (3.44 g, 8.20 mmol) in anhydrous THF (50 mL) at −70° C. The reaction was allowed to warm to −10° C. over a period of 2 h, after which time, it was placed in an ice bath and stirred for another 50 minutes. Finally, the reaction was quenched by the addition of a saturated ammonium chloride solution. The mixture was extracted several times with ethyl acetate. The recombined organic layer was extracted with brine, dried over sodium sulfate, filtered and evaporated. The resultant crude product was flashed with 10% ethyl acetate in hexanes to give the product as a colorless oil. $^1$H-NMR(CDCl$_3$, 400 MHz): 1.21(t, J=7.2, 3H); 1.41(s, 9H); 2.49–2.86(m, 4H); 3.28(q, J=6.9 Hz, 1H); 4.13(m, 2H); 5.1(m, 2H); 7.32(m 5H).

EXAMPLE 70

3-Carboxy-pentanedioic acid tert-butyl ester ethyl ester

A solution of the compound of example 69 (2.29 g, 6.54 mmol) in ethanol (95%, 500 mL) was hydrogenated in the presence of a catalytic amount of palladium (10% on charcoal). After 24 h of stirring, the reaction was complete. The mixture was filtered over a celite pad and the solvent evaporated. The residue was distributed between ethyl acetate and water. The aqueous phase was extracted twice more with ethyl acetate. The recombined organic layer was washed with brine, dried over sodium sulfate, filtered, and evaporated. The product was sufficiently pure on the basis of its $^1$H-NMR spectrum to be used in the next step. $^1$H-NMR (CDCl$_3$, 400 MHz): 1.23(t, J=7.1, 3H); 1.41(s, 9H); 2.53–2.81(m, 4H); 3.25(m, 1H); 4.13(m, 2H).

EXAMPLE 71

3-(2-Biphenyl-4-yl-ethylcarbamoyl)-pentanedioic acid tert-butyl ester ethyl ester A solution of the compound of example 70 (1.55 g, 5.96 mmol) in anhydrous DMF (5 mL) was treated successively with DIEA (5.2 mL), 4-biphenylethyl amine (2.40 g, 11.92 mmol) and TBTU (2.76 g, 8.34 mmol). The reaction mixture was stirred for 24 h at room temperature. The reaction mixture was treated with HCl (1M, excess) and the mixture was extracted several times with ethyl acetate. The recombined organic layer was washed with brine, dried over sodium sulfate, filtered and evaporated. The residue was flashed with 30% ethyl acetate in hexanes and the desired product was obtained as a white solid. $^1$H-NMR(CDCl$_3$, 400 MHz): 1.22(t, J=7.2, 3H); 1.42(s, 9H); 2.32–2.42(m, 2H); 2.60–2.75(m, 2H); 2.83(t, J=7.1 Hz, 2H); 3.02(m, 1H); 3.53(m, 2H); 4.11(m, 2H); 6.25(m, t, 5.1 Hz, 1H); 7.30(m, 3H); 7.43(m, 2H); 7.57(m, 4H).

EXAMPLE: 72

3-(2-Biphenyl-4-yl-ethylcarbamoyl)-pentandioic acid mono-tert-butyl ester

To a solution of the compound of example 71 (1.09 g, 2.48 mmol) in methanol (50 mL) was added drop wise a sodium hydroxide solution (1N, 5 mL, 5 mmol). After stirring the reaction mixture for 24 h, the solvent was evaporated. The residue was partitioned between water and ether. The aqueous phase was acidified with concentrated HCl, and then extracted with ethyl acetate. The organic phase was washed with brine, dried, filtered and evaporated to give the product as a white solid. 1H-NMR(CDCl3, 400 MHz): 1.37(s, 9H); 2.28–2.61(m, 4H); 2.79(t, J=7.3 Hz, 2H); 3.08(m, 1H); 3.27(m, 1H); 3.39 (m, 2H); 6.25(m, t, 5.1 Hz, 1H); 7.26(m, 3H); 7.36(m, 2H); 7.52(m, 4H).

EXAMPLE 73

4-(Bis-benzyloxy-phosphoryl)-butyric acid ethyl ester

To a suspension of NaH (60%, 2.52 g, 63 mmol) in DMF (60 mL) was added dibenzyl phosphite (12 mL, 48.45 mmol). After 15 minutes of stirring, ethyl-4-bromobutyrate was added and the mixture was stirred for 48 h at room temperature. The DMF was removed by evaporation. The residue was partitioned between brine, ammonium chloride and ether. The water phase was extracted several times with ether. The recombined organic layer was extracted with brine, dried over sodium sulfate, filtered and evaporated. The residue was flashed using 50% ethyl acetate in hexanes to afford the product as a colorless oil. $^1$H-NMR(CDCl$_3$, 400 MHz): 1.23(t, J=7.2 Hz, 3H); 1.77–2.04(m, 4H); 2.37(m, 2H); 4.10(q, J=7.2 Hz, 2H), 5.03(m, 4H); 7.31(m, 10H). $^{31}$P-NMR(CDCl$_3$, 400 MHz): 32.78.

EXAMPLE 74

4-(Bis-benzyloxy-phosphoryl)-butyric acid

A solution of the compound of example 73 (8.66 g, 23.02 mmol) in THF (150 mL) was treated drop wise with a solution of lithium hydroxide-mono hydrate (1.97 g, 46.04 mmol) in water (150 mL). The reaction was complete after about 1 h, according to TLC analysis. Most of the solvent was evaporated. The residue was partitioned between water and ether. The organic phase was separated and the alkaline phase was extracted again with ether. It was next acidified with HCl (6M) to pH~1 followed by several extractions with ethyl acetate. The recombined organic layer was dried over sodium sulfate, filtered, and evaporated to give the product as colorless oil. 1H-NMR(CDCl3, 400 MHz: 1.88(m, 4H); 2.40(t, J=6.9 Hz, 2H); 4.97,4.96, 5.05(2dd, J1=11.8 Hz. J2=8.1 Hz, 4H); 7.35(m, 10H). 31P-NMR(CDCl3, 400 MHz): 33.15.

EXAMPLE 75

[4-(4-Benzyl-2-oxo-oxazolidin-3-yl)-4-oxo-butyl]-phosphonic acid dibenzyl ester

To a stirred solution of the compound of example 74 (6.45 g, 18.52 mmol) in anhydrous THF (100 mL) was added triethyl amine. The reaction mixture was then cooled to −70° C. After 10 minutes, trimethyl acetyl chloride (2.5 mL, 20.37 mmol) was added and stirring was continued for another 15 minutes at −70° C. followed by 1 h in an ice bath. In a separate flask, n-BuLi (7.5 mL) was added drop wise to a solution of R-4-benzyl-2-oxazolidine in anhydrous THF (60 mL) at −70° C. After 15 minutes, this mixture was transferred by cannula to the former solution cooled to −70° C. Stirring was continued for 20 minutes at −70° C., followed by 2 h in an ice bath. A saturated ammonium chloride solution was added (excess), and the mixture was extracted several times with ethyl acetate. The recombined organic layer was washed with brine, with a saturated sodium bicarbonate solution and brine, followed by drying over sodium sulfate, filtration and evaporation. The residue was flashed starting with 40% ethyl acetate, followed by 60% ethyl acetate in hexanes. The product was obtained as a white solid. 1H-NMR(CDCl3, 400 MHz: 1.84–2.04(, 4H); 2.70(m, 1H); 2.86(m, 1H); 3.03(m, 1H), 3.24(m, 1H); 4.15 (m, 2H); 4.63(m, 1H); 4.99(m, 4H); 7.32(m, 15H). 31P-NMR(CDCl3, 400 MHz): 33.23. FAB:508.1 (MH+).

EXAMPLE 76

3-(4-Benzyl-2-oxo-oxazolidine-3-carbonyl)-5-(bis-benzyloxy-phosphoryl)-pentanoic acid tert-butyl ester A solution of the compound of example 75 (5.42 g, 10.70 mmol) in anhydrous THF (100 mL) was prepared and cooled to −70° C. A solution of NaHDMS in THF (1M, 40.2 mL, 40.2 mmol) was added drop wise. The reaction mixture was stirred for 1 h at −70° C. and for 4 h at −48° C., after which time, the reaction was not complete according to TLC analysis. The reaction was allowed to stir for another 1 h at −30° C. At this stage, the completion of the reaction could not yet be confirmed by TLC analysis. The reaction was quenched by the addition of a saturated solution of ammonium chloride. The mixture was extracted several times with ethyl acetate. The recombined organic layer was washed with brine, filtered and evaporated. The residue was flashed using 50% ethyl acetate in hexanes and the product was obtained as a colorless oil. $^1$H-NMR(CDCl$_3$, 400 MHz: 1.41(s, 9H); 1.83(m, 3H); 2.34(m, 1H); 2.71(m, 2H); 3.29 (m, 1H); 3.15(m, 2H); 4.59(m, 1H); 4.94, 5.05(2m, 4H); 7.17–7.37(m, 15H). $^{31}$P-NMR (CDCl$_3$, 400 MHz): 33.23.

EXAMPLE 77

2[2-(Bis-benzyloxy-phosphoryl)-ethyl]-succinic acid 4-tert-butyl ester

A solution of the compound of example 76 (1.03 g, 1.66 mmol) in a mixture of THF/water (4:1, 20 mL) was cooled in an ice bath and treated drop wise with a hydrogen peroxide solution (30%, 0.7 mL). After 5 minutes, a solution of lithium hydroxide monohydrate (1M, 6.6 mL, 6.6 mmol) was added over a period of 10 minutes. The reaction was completed following 2 h of stirring in the ice bath. At this stage, an aqueous solution of sodium sulfite (850 mg, 6.64 mmol, 5 mL) was added. The ice bath was removed and the reaction mixture was stirred for another 30 minutes. Most of the solvent was removed by evaporation and the residue was extracted with ether. The alkaline phase was acidified with HCl (6M) to pH~1 and extracted three times with ethyl acetate. The recombined organic layer was washed with brine, dried over sodium sulfate, filtered and evaporated. The desired product was obtained as a colorless oil. $^1$H-NMR (CDCl$_3$, 400 MHz: 1.40(s, 9H); 1.85(m, 4H); 2.27, 2.58(2dd, J$_1$=16.5 Hz. J$_2$=5.6 Hz, 4H); 2.84(m, 1H); 4.98(m, 4H); 7.31(m, 10H). $^{31}$P-NMR (CDCl$_3$, 400 MHz): 33.14.

EXAMPLE 78

2-(Diethoxy-phosphoryl)-4-phenyl-butyric acid tert-butyl ester

Diethylphosphonoacetate (1.00 g, 3.96 mmol) was added drop wise at 0° C. to a stirring suspension of sodium hydride (0.095 g, 3.96 mmol) in anhydrous THF (50 mL). The mixture was then allowed to stir for 10 minutes at 0° C. and then for 1 hour at room temperature before it was cooled again to 0° C. followed by the addition of phenethyl bromide (0.73 g, 3.96 mmol). The mixture was then allowed to proceed for 24 hours at room temperature. The solvent was evaporated and the residue was taken-up in water and extracted 4 times with ethyl acetate. The organic extracts were combined, washed with water and brine, dried using magnesium sulfate, filtered and evaporated. The crude residue was purified by flash chromatography (ethyl acetate in hexanes, 10%–50%) to afford the desired compound as a colorless oil. $^1$H NMR (CDCl$_3$, 400 MHz) δ 7.18 (m, 2H), 7.09 (m, 2H), 4.07–3.99 (m, 4H), 2.82–2.72 (m, 1H), 2.69–2.60 (m, 1H), 2.54–2.45 (m, 1H), 2.25–2.12 (m, 1H), 2.08–1.94 (m, 1H), 1.41 (s, 9H), 1.24–1.18 (m, 6H); $^{13}$C (CDCl$_3$, 400 MHz) δ 167.7, 140.4, 128.3, 128.2, 125.9, 81.5, 62.2, 46.3, 45.0, 34.1, 28.5, 27.7, 16.1; $^{31}$P (CDCl$_3$, 400 MHz) δ 23.7. HRMS calcd. for C$_{18}$H$_{29}$O$_5$P 356.1753. found 356.1757.

EXAMPLE 79

2-(Diethoxy-phosphoryl)-4-phenyl-butyric acid

Trifluoroacetic acid (4 mL) was added drop wise to a stirring solution of 2-(diethoxy-phosphoryl)-4-phenyl-butyric acid tert-butyl ester (1.00 g, 2.81 mmol) in anhydrous dichloromethane (16 ml). The mixture was stirred for 2 hours at room temperature followed by the removal of the solvent. The crude residue was purified by flash chromatography (100% dichloromethane-2.5% methanol in dichloromethane) to afford the desired compound as a yellowish oil. $^1$H NMR (CDCl$_3$, 400 MHz) δ 11.21 (br s, 1H), 7.29–7.14 (m, 5H), 4.24–4.12 (m, 4H), 3.09–3.00 (m, 1H), 2.82–2.75 (m, 1H), 2.64–2.57 (m, 1H), 2.35–2.27 (m, 1H), 2.15–2.11 (m, 1H), 1.31–1.25 (m, 6H); $^{13}$C (CDCl$_3$, 100 MHz) δ 170.4, 140.4, 128.4, 128.3, 126.1, 63.4, 63.2, 45.1, 43.8, 34.0, 28.5, 16.0; $^{31}$p (CDCl$_3$, 400 MHz) δ 24.3; HRMS calcd. for C$_{14}$H$_{21}$O$_5$P 300.1127. found 300.1129.

EXAMPLE 80

(4-Phenyl-butyl)-phosphinic acid

To a solution of NaH$_2$PO$_2$.H$_2$O (2.65 g, 25 mmol) and 4-phenyl 1-butene (1.5 mL, 10 mmol) in methanol (40 mL) was added triethylborane (10 mL, 10 mmol, 1.0 M solution in hexanes). The clear colorless solution was stirred at room temperature for a period of 4 hours, with the reaction vessel open to the atmosphere. The reaction mixture was diluted with ethyl acetate (100 mL) and washed with an aqueous KHSO$_4$ solution (100 mL, 2.0 M). The aqueous layer was extracted three times with ethyl acetate and the combined organic extracts were dried (Na$_2$SO$_4$) and concentrated to provide the crude product (1.78 g) as a pale yellow oil which was carried on to the next step without any further purification. $^{31}$P NMR (CDCl$_3$) δ 37.5.

EXAMPLE 81

(4-Phenyl-butyl)-phosphinic acid benzyl ester

To a solution of the compound of example 80 (1.75 g, 8.83 mmol) in dry CH2Cl2 (40 mL) was added benzyl alcohol (1.83 mL, 17.7 mmol), DMAP (108 mg, 0.88 mmol) and EDC (1.91 g, 10.0 mmol). The mixture was then stirred at room temperature for 18 h. The mixture was concentrated in vacuum, taken-up in ethyl acetate and washed with NaHCO3 (5%) and H2O. Drying (Na2SO4) and concentration gave 2.8 g of a pale yellow oil which was purified by flash chromatography (SiO$_2$, ethyl acetate:hexane (1:1)) to give 1.92 g of the title compound.

EXAMPLE 82

N-[1-Benzyloxycarbonyl-2-(1H-indol-3-yl)-ethyl]-3-tert-butoxycarbonyl amino-succinamic acid benzyl ester To a commercially available solution of H$_2$N-Trp-OBn (3.15 g, 9.76 mmol) in dry DMF (50 mL) was added neat DIPEA (1.7 mL, 9.76 mmol). The slightly yellow solution was then cooled to 0° C. and Boc-Asp (OBn) OSu was added in one portion. After 10 min at 0° C., the ice bath was removed and the mixture was allowed to warm to room temperature followed by an additional 5 hours of stirring. The reaction mixture was treated as previously described in example 56. Drying (Na$_2$SO$_4$) and concentration under vacuum gave the title dipeptide (5.46 g; 96%) as white foam: m.p: 46–48° C., R$_f$ (ethyl acetate)=0.32. The spectroscopic data was consistent with the structure.

EXAMPLE 83

3-Amino-N-[1-benzyloxycarbonyl-2-(1H-indol-3-yl)-ethyl]-succinamic acid benzyl ester To a round-bottomed flask (1L) was added a solution of (HCl) dioxane (180 mL. 4.0 M). This solution was cooled to 0° C. followed by the addition of the compound of example 82 in one portion while stirring. The ice bath was removed and the reaction was further stirred for 30 min at room temperature before it was concentration under vacuum at <25° C. Washing the residue with dry ether gave the product (4.39 g) as a tanned solid. This product was used for the next reactions without further purification.

EXAMPLE 84

3-(2-Biphenyl-4-yl-ethylcarbamoyl)-6-tritylsulfanyl-hexanoic acid tert-butyl ester To a solution of the compound of example 29 (200 mg, 0.41 mmol) and HOBt (66 mg, 0.49 mmol) in DMF (2 mL), were added 4-biphenylethylamine (124 mg, 0.62 mmol) and DIC (78 μL) respectively. The reaction mixture was stirred for 24 h at room temperature. The reaction mixture was partitioned between HCl (0.5N, excess) and ethyl acetate. The aqueous phase was extracted several times with ethyl acetate. The recombined organic layer was washed with brine, with a saturated sodium hydrogen carbonate solution, and again with brine. The solvent was evaporated following drying over sodium sulfate, and the crude was flashed using 30% ethyl acetate in hexanes. $^1$H-NMR (CDCl$_3$, 400 MHz): 1.55(s, 9H); 1.41–1.57(m, 2H); 2.04–2.28(m, 6H); 2.54(m, 1H); 2.80(m, 2H); 3.45–3.55(m, 2H), 5.66(m, 1H); 7.19–7.57(m, 24H).

EXAMPLE 85

3-(2-Biphenyl-4-yl-ethylcarbamoyl)-6-mercapto-hexanoic acid

This compound was obtained by standard deprotection of the compound of example 84, followed by HPLC purification.

EXAMPLE 86

3-{2-[3-tert-Butoxycarbonyl-2-(2-tritylsulfanyl-acetylamino)-propionyl amino]-2-carboxy-ethyl}-indole-1-carboxylic acid tert-butyl ester To Fmoc-Asp (O$^t$But)-OH (987 mg, 2.40 mmol) in 1-methyl-2-pyrrolidinone (NMP, 10 mL) was added HOBT (324 mg) and the clear colorless solution was cooled to 0° C. Diisopropyl carbodiimide (DIC, 375 μL, 2.4 mmol) was then added drop wise. After the addition was complete, the clear solution was left to warm to room temperature and was further stirred for 30 minutes. Concurrently, H-Trp (Boc)-2-Cl-Trt resin (1.0 g, 0.4 mmol) was swelled in just enough NMP for 30 min. The active ester solution was then cannulated to the solid phase peptide synthesis vessel, containing the resin, and the mixture was gently stirred at room temperature for 2 hours. The mixture was then filtered and the resin was washed with DMF (3×), DCM (3×), MeOH (3×), DCM (3×), and finally with MeOH (3×). At this stage, the resin had a loading of 0.32 mmol/g. The Fmoc group was removed using 25% piperidine in DMF. To access the purity, a small portion (20 mg) of the resin was cleaved to give H-Asp (OBut)-Trp(Boc)-OH with purity exceeding 98% according to NMR and HPLC. $^1$H NMR (CD$_3$OD, 400 MHz) δ 8.06 (d, 1H), 7.7 (d, 1H), 7.51 (s, 1H), 7.25 (dt, 2H), 4.6 (dd, 1H), 3.94 (dd, 1H), 3.12 (dd, 1H), 2.95 (dd, 1H), 2.65 (dd, 1H), 1.67 (s, 9H), 1.45 (s, 9H).

The rest of the resin was coupled to S-trityl thioglycolic acid (6 equivalents) in the same manner as mentioned above.

After 2 hours at room temperature, the resin was filtered, washed, dried and cleaved using cocktail B (DCM:HFIP, 4:1) to give the title compound (200 mg, 85% based on initial loading of resin) as a white foam: $^1$H NMR (CD$_3$OD, 300 MHz) δ 8.14 (d, 1H), 7.60–7.15 (m, 20H), 4.75 (m, 1H), 4.40 (m, 1H), 3.30 (dd, 1H), 3.16 (dd, 1H), 3.0 (dd, 2H), 2.60 (dd, 1H), 2.30 (dd, 1H), 1.67 (s, 9H), 1.42 (s, 9H); $^{13}$C NMR (CDCl$_3$, 300 MHz) δ 175.1, 171.5, 170.8, 169.7, 150.1, 144.2, 135.7, 130.7, 129.9, 128.5, 127.5, 125.0, 124.8, 123.2, 119.3, 115.7, 115.2, 84.3, 82.5, 68.3, 53.9, 53.1, 49.5, 36.9, 36.0, 28.6, 28.2; MS (PosFAB) 814.1 (MH)$^+$, HRMS calcd for C$_{45}$H$_{49}$O$_8$N$_3$SNa (MNa$^+$) 814.3139. found 814.3157.

EXAMPLE 87

N-[1-Carboxy-2-(1H-indol-3-yl)-ethyl]-3-(2-mercapto-acetylamino)-succinamic acid The fully protected peptide of example 86 was subjected to cleavage cocktail A to remove the protecting groups, and to liberate the crude target peptidic thioglycolylamide which was isolated as mentioned above (general procedures) and purified by preparative HPLC (49% overall yield): $^1$H NMR (CD$_3$OD, 300 MHz) δ 7.55 (d, 1H), 7.32 (d, 1H), 7.14–6.98 (m, 3H), 4.72 (ddd, 2H), 3.35 (dd, 1H), 3.31 (dd, 1H), 2.79 (dd, 1H), 2.65 (dd, 1H); $^{13}$C NMR (CDCl$_3$, 300 MHz) δ 172.1, 171.3, 170.6, 169.8, 135.3, 126.3, 122.1, 119.8, 117.3, 116.9, 109.7, 107.9, 52.0, 48.6, 33.7, 25.6, 25.4; MS (Pos. FAB) 394.1 (MH)$^+$ The following non-limiting examples wherein the □-substituent (P1 substituent) is the variable, were prepared in a manner analogous to that presented in Examples 86 and 87. Thus, the resin-bound dipeptide H$_2$N-Asp(O$^t$But)-Trp (Boc)-O-2-Cl-Tritylchloride resin (example 86) was coupled to various substituted-2-tritylsulfanyl-propionic acid derivatives (Examples 4 to 20) using the coupling, cleavage/deprotection, purification protocols as previously described, to provide the following derivatives of which the preparation of the derivative carrying a phenmethyl □-substituent is described in detail.

EXAMPLE 88

3-{2-[3-tert-Butoxycarbonyl-2-(3-phenyl-2-tritylsulfanyl-propionylamino)-propionylamino]-2-carboxyethyl}-indole-1-carboxylic acid tert-butyl ester This compound was prepared using the same protocol mentioned above for example 86. Thus, the resin-bound dipeptide, H$_2$N-Asp(O$^t$But)-Trp (Boc)-O-2-Cl-Tritylchloride resin (example 86) was coupled to 3-phenyl-2-tritylsulfanyl-propionic acid (example 4) using the DIC/HOBT method. To ensure complete coupling, the reaction was repeated with 2 equivalents of the S-trityl acid derivative. After standard washing and drying, the resin was cleaved using cocktail B to give the title compound as a crispy white foam: $^1$H NMR (CD$_3$OD, 400 MHz) δ 8.12 (d, 1H), 6.91–7.52 (m, 25H), 4.66 (t(d), 1H), 4.20 (t(d), 1H), 3.25 (dd, 1H), 3.08 (dd, 1H), 2.92 (m, 2H), 2.61 (dd, 1H), 2.59 (dd, 1H), 2.12 (dd, 1H), 1.67 (s, 9H), 1.35 (s, 9H).

EXAMPLE 89

N-[1-Carboxy-2-(1H-indol-3-yl)-ethyl]-3-(2-mercapto-3-phenyl-propionyl amino)-succinamic acid The fully protected peptide obtained above was subjected to cleavage cocktail A to remove the protecting groups and liberate the crude target peptide thioglycolylamide, which was isolated as mentioned above (general procedures), and purified by preparative HPLC: MS (Neg. FAB, NBA) 481.9 (M−2H).

EXAMPLE 90

N-[1-Carboxy-2-(1H-indol-3-yl)-ethyl]-3-(2-mercapto-propionylamino)-succinamic acid MS (Pos. FAB) 508 (MH$^+$).

EXAMPLE 91

N-[1-Carboxy-2-(1H-indol-3-yl)-ethyl]-3-(2-mercapto-4-methyl-pentanoylamino)-succinamic acid MS (Pos. FAB) 534 (MH$^+$).

EXAMPLE 92

N-[1-Carboxy-2-(1H-indol-3-yl)-ethyl]-3-(2-mercapto-3-methyl-butyrylamino)-succinamic acid MS (Pos. FAB) 436 (MH$^+$).

EXAMPLE 93

N-[1-Carboxy-2-(1H-indol-3-yl)-ethyl]-3-(3-hydroxy-2-mercapto-propionylamino)-succinamic acid MS (Pos. FAB) 424 (MH$^+$).

EXAMPLE 94

N-[1-Carboxy-2-(1H-indol-3-yl)-ethyl]-3-(3-hydroxy-2-mercapto-butyrylamino)-succinamic acid MS (Pos. FAB) 438 (MH$^+$), 460 (MNa$^+$).

EXAMPLE 95

N-[1-Carboxy-2-(1H-indol-3-yl)-ethyl]-3-(2-mercapto-hexanoylamino)-succinamic acid MS (Pos. FAB) 450 (MH$^+$).

EXAMPLE 96

N-[1-Carboxy-2-(1H-indol-3-yl)-ethyl]-3-(2-mercapto-4-phenyl-butyrylamino)-succinamic acid MS (Pos. FAB) 498 (MH$^+$)

EXAMPLE 97

N-[1-Carboxy-2-(1H-indol-3-yl)-ethyl]-3-(2-mercapto-2-phenyl-acetylamino)-succinamic acid MS (Pos. FAB) 470 (MH$^+$).

EXAMPLE 98

3-(3-Biphenyl-4-yl-2-mercapto-propionylamino)-N-[1-Carboxy-2-(1H-indol-3-yl)-ethyl]-succinamic acid MS (Pos. FAB) 560 (MH$^+$).

EXAMPLE 99

3-(3-(4-Benzyloxy-phenyl)-2-mercapto-propionylamino)-N-[1-Carboxy-2-(1H-indol-3-yl)-ethyl]-succinamic acid MS (Pos. FAB) 590 (MH$^+$).

EXAMPLE 100

N-[1-Carboxy-2-(1H-indol-3-yl)-ethyl]-3-[3-(4-fluoro-phenyl)-2-mercapto-propionylamino]-succinamic acid MS (Pos. FAB) 502 (MH$^+$).

EXAMPLE 101

N-[1-Carboxy-2-(1H-indol-3-yl)-ethyl]-3-[2-mercapto-3-(4-methoxy-phenyl)-propionylamino]-succinamic acid MS (Pos. FAB) 534 (MH$^+$).

EXAMPLE 102

N-[1-Carboxy-2-(1H-indol-3-yl)-ethyl]-3-(3-cyclohexyl-2-mercapto-propionylamino)-succinamic acid MS (Pos. FAB) 490 (MH$^+$).

EXAMPLE 103

N-[1-Carboxy-2-(1H-indol-3-yl)-ethyl]-3-[3-(1H-indol-3-yl)-2-mercapto-propionylamino]-succinamic acid MS (Pos. FAB) 502 (MH$^+$).

EXAMPLE 104

N-[1-Carboxy-2-(1H-indol-3-yl)-ethyl]-3-(2-mercapto-3-naphthalen-2-yl-propionylamino]-succinamic acid MS (Pos. FAB) 534 (MH$^+$).

The following non-limiting examples wherein the P'2 subsistent is the variable, were prepared in a manner analogous to that presented in Examples 86 and 88. Thus, in each case, the required amino acid (or amino alcohol) was first loaded onto the 2-Cl-Trt resin followed by Fmoc deprotection, coupling with Fmoc-Asp (OBut)-OH, Fmoc deprotection and finally coupling with (S)-3-phenyl-2-tritylsulfanyl-propionic acid. Employing the same cleavage/deprotection, and purification protocols as previously described, provided the following non-limiting examples of which the preparation of the naphthyl derivative is described in detail.

EXAMPLE 105

N-(1-Carboxy-2-naphthalen-2-yl-ethyl)-3-(3-phenyl-2-tritylsulfanyl-propionylamino)-succinamic acid tert-butyl ester This compound was assembled by first loading the first amino acid, Fmoc-2-Nal-OH onto 2-Cl-Trt resin. Thus, to Fmoc-2-Nal-OH (0.26 g, 0.59 mmol) in dry DCM (5 mL) was added diisopropylethylamine (311 □L, 1.78 mmol) drop wise at room temperature. This solution was then added drop wise to the 2-Cl-Trt resin (0.50 g, 0.54 mmol, pre-swelled in dry DCM for 30 minutes). After the addition was complete, the reaction mixture was gently stirred at room temperature for 90 minutes. HPLC grade methanol (1 mL) was then added and gentle stirring continued for 10 more minutes. The resin was filtered and washed with DCM (3×), DMF (3×), 2-propanol (3×), DMF (3×), DCM (3×) and MeOH (3×), and dried to give 0.7 g of the Fmoc-2-Nal-O-2Cl-Trt resin as yellow granules. At this stage the resin loading was determined to be 0.7 mmol/g.

After removal of the Fmoc groups, Fmoc-Asp(OBut)-OH was coupled to H-2-Nal-O-2Cl-Trt-resin in the same manner mentioned above for example 86. After removal of the Asp Fmoc group followed by the standard washing and drying of the resin, a small portion (15 mg) was cleaved to give H-Asp(OBut)-2-Nal-OH with purity exceeding 98% according to NMR and HPLC: $^1$H NMR (CD$_3$OD, 400 MHz) δ 7.95 (m, 3H), 7.71 (s, 1H), 7.42 (m, 3H), 4.62 (dd, 1H), 3.97 (dd, 1H), 3.42 (dd, 1H), 3.15 (dd, 1H), 2.92 (dd, 1H), 2.64 (dd, 1H), 1.45 (s, 9H).

The rest of the resin was coupled to (s)-3-phenyl-2-tritylsulfanyl-propionic acid as mentioned above (Example 4) using the DIC/HOBT method. After isolation and cleavage using cocktail B the title compound was obtained (262 mg, 87% yield based on the initial loading of the resin) as a white foam: $^1$H NMR (CD$_3$OD, 400 MHz) δ 7.71 (m, 5H), 7.4 (m, 4H), 6.8–7.32 (m, 18H), 4.65 (m, 1H), 4.18 (m, 1H), 3.31 (dd, 1H), 3.05 (dd, 1H), 2.88 (m, 2H), 2.57 (m, 2H), 2.1 (dd, 1H).

EXAMPLE 106

N-(1-Carboxy-2-naphthalen-2-yl-ethyl)-3-(2-mercapto-3-phenyl propionylamino)-succinamic acid The fully protected peptide obtained above was subjected to cocktail A to remove the protecting groups and liberate the crude target peptidic thioglycolylamide which was isolated as mentioned above (general procedures) and purified by preparative HPLC (45% overall yield): $^1$H NMR (CD$_3$OD, 300 MHz) δ 7.82 (m, 4H), 7.41 (m, 3H), 7.15 (m, 5H), 6.98 (ddd, 1H), 3.48 (t, 1H), 3.31 (dd, 1H), 3.15 (dd, 1H), 3.03 (dd, 1H), 2.76 (m, 2H), 2.63 (dd, 1H); $^{13}$C NMR (CDCl$_3$, 300 MHz) δ 171.4, 176.5, 176.1, 174.8, 141.9, 138.0, 137.3, 136.3, 132.6, 131.8, 131.5, 131.4, 131.2, 131.0, 130.1, 129.4, 129.0, 57.5, 53.7, 46.7, 45.4, 44.7, 40.8, 38.9; MS (Neg FAB, NBA) 492.9 (M−2H).

EXAMPLE 107

N-(1-Carboxy-2-hydroxy-ethyl)-3-(2-mercapto-3-phenyl-propionyl amino)-succinamic acid MS (Pos. FAB) 385 (MH+), 407 (MNa+).

EXAMPLE 108

N-[1-Carboxy-2-(4-hydroxy-phenyl)-ethyl]-3-(2-mercapto-3-phenyl-propionylamino)-succinamic acid $^1$H NMR (MeOD-4, 400 MHz) □ 7.32–7.12 (m, 5H), 7.05 (d, 1H), 6.73 (d, 1H), 4.70 (dd, 1H), 4.55 (dd, 1H), 3.61 (t, 1H), 3.19 (dd, 1H), 3.07 (dd, 1H), 2.95 (m, 2H), 2.78 (dd, 1H), 2.65 (dd, 1H); $^{13}$C NMR (CDCl$_3$, 100 MHz) □ 175.2, 173.4, 173.1, 172.2, 157.2, 139.1, 131.2, 130.3, 129.2, 128.1, 127.5, 115.8, 55.2, 51.3, 44.2, 42.1, 37.6, 36.6. MS (Pos. FAB) 461 (MH+).

EXAMPLE 109

N-[1-Carboxy-2-phenyl-ethyl]-3-(2-mercapto-3-phenyl-propionyl amino)-succinamic acid $^1$H NMR (MeOD-4, 400 MHz) □ 7.32–7.05 (m, 10H), 4.70 (dd, 1H), 4.59 (dd, 1H), 3.61 (t, 1H), 3.15 (m, 2H), 2.92 (dd, 1H), 2.85 (dd, 1H), 2.78 (dd, 1H), 2.63 (dd, 1H); $^{13}$C NMR (CDCl$_3$, 100 MHz) □ 175.1, 173.4, 173.1, 172.2, 138.7, 137.8, 130.2, 130.1, 129.2, 127.4, 55.1, 51.9, 44.4, 42.8, 38.1, 36.1. MS (Pos FAB) 445 (MH+)

EXAMPLE 110

N-(2-Biphenyl-4-yl-1-Carboxy-ethyl)-3-(2-mercapto-3-phenyl-propionyl amino)-succinamic acid MS (Neg. FAB) 518(M+−2H); (65%).

EXAMPLE 111

N-(1-Benzyl-2-hydroxy-ethyl)-3-(2-mercapto-3-phenyl-propionyl amino)-succinamic acid MS (Pos. FAB) 431(MH)+; (82%).

Following the same solid phase protocols as described above, the following non-limiting examples wherein the P'1 L-Asp of the compound of Example 31 has been replaced with D-Asp, L-Glu, or L-Gla, were prepared.

EXAMPLE 112

N-[1-Carboxy-2-(1H-indol-3-yl)-ethyl]-3-(2-mercapto-3-phenyl-propionylamino)-succinamic acid. (83%).

EXAMPLE 113

2-[2-[1-Carboxy-2-(1H-indol-3-yl)-ethylcarbamoyl]-2-(2-mercapto-3-phenyl-propionylamino)-ethyl]-malonic acid (Pos. FAB) 542.7 (MH+); (45%)

EXAMPLE 114

4-[1-Carboxy-2-(1H-indol-3-yl)-ethylcarbamoyl]-4-(2-mercapto-3-phenyl-propionylamino)-ethyl]-butyric acid (75%)

The preferred method for preparing the following compounds in which the tryptophan residue (Examples 87 and 89) has either been completely replaced by a variety of amine moieties, or only its carboxyl function has been transformed to amides and esters, involves fragment condensation strategy. Thus, after assembly of the desired peptide on the solid support, cleavage from the resin was conducted using cocktail B as in Example 86 (see also the section of general procedures) in order to only liberate the carboxy terminus for further elaboration. Example 115, illustrating the preparation of the methyl amide, is a representative example.

EXAMPLE 115

N-[2-(1H-indol-3-yl)-methylcarbamoyl-ethyl]-3-(2-mercapto-acetyl amino)-succinamic acid To a solution of the protected dipeptide of Example 86 (100 mg, 0.13 mmol), methylamine hydrochloride (8.5 mg, 0.13 mmol), and HOBt (17 mg, 0.13 mmol) in DMF (2 mL), was added EDCI (24 mg, 0.13 mmol) at 0° C., followed by NMM (14 μL, 0.13 mmol) under argon. The ice bath was removed and the mixture was further stirred at room temperature for 16 h followed by the addition of an aqueous NaHCO$_3$ (5%) solution. The mixture was extracted with EtOAc and the combined organic extracts were sequentially washed with NaHCO$_3$ (5%), water, KHSO$_4$ (5%) and finally with water. Drying (Na$_2$SO$_4$) and concentration yielded the desired methylamide (100 mg, 96%) which exhibited the following data: $^1$H NMR (CDCl$_3$, 300 MHz) d 8.15 (br s, 1H), 7.63 (d, 1H), 7.42–7.18 (m, 18H), 6.81 (d, 1H), 6.62 (d, 1H), 4.62 (m, 1H), 4.25 (m, 1H), 3.22 (dd, 1H), 3.18 (dd, 1H), 2.92 (m, 2H), 2.64 (d, 3H), 2.58 (dd, 1H), 2.42 (dd, 1H), 1.63 (s, 9H), 1.41 (s, 9H); $^{13}$C NMR (CDCl$_3$, 75 MHz) d 171.3, 171.1, 170.3, 169.2, 149.9, 144.3, 135.8, 130.6, 129.9, 128.6, 128.3, 127.5, 125.1, 124.9, 123.2, 119.6, 115.7, 84.1, 82.5, 68.3, 53.9, 50.2, 36.6, 36.0, 28.6, 28.4, 27.5, 26.9; MS(Pos. FAB) 805 (MH+). The methylamide was deprotected to provide the title compound (72%); MS (Pos. FAB) 407 (MH+), 429 (MNa+).

EXAMPLE 116

N-[1-(1-Carboxy-2-hydroxy-ethylcarbamoyl)-2-(1H-indol-3-yl)-ethyl]-3-(2-mercapto-3-phenyl-propionylamino)-succinamic acid The title compound was prepared by condensing H-Ser (But)OBut with the protected dipeptide of Example 88, followed by deprotection and purification by HPLC (40%): (Pos. FAB) ? (MH+).

EXAMPLE 117

N-[2-(1H-indol-3-yl)-methoxycarbonyl-etjyl]-3-(2-mercapto-acetyl amino)-succinamic acid Esterification of the compound of Example 86 with methanol using EDCI, and in the presence of 10 mol % of DMAP gave, following deprotection, the title compound (41%): (Pos. FAB) 408 (MH+), 430 (MNa+).

EXAMPLE 118

N-[2-(1H-indol-3-yl)1-ethyl]-3-(2-mercapto-3-phenyl-propionylamino)-succinamic acid This compound was prepared by condensing tryptamine with 2-(3-phenyl-2-tritylsulfanyl-propionylamino)-succinic acid 4-tert-butyl ester using the same coupling conditions as previously described. Deprotection and purification then provided the title compound (39%): (Pos FAB) 440 (MH+).

EXAMPLE 119

2-(2-tert-Butoxycarbonylmethyl-5-tritylsulfanyl-pentanoylamino)-succinic acid di-tert-butyl ester To H-Asp (O$^t$Bu)-O$^t$Bu hydrochloride salt (28 mg, 0.10 mmol) in dry DMF (2 mL) was sequentially added at room temperature 2-(3-tritylsulfanyl-propyl)-succinic acid 4-tert-butyl ester (50 mg, 0.10 mmol), HOBt (14 mg, 0.10 mmol), PYBOP (56 mg, 0.11 mmol) and DIPEA (37 μL, 0.20 mmol). The usual aqueous work up yielded the title compound (62 mg, 86%) as a colorless residue: $^1$H NMR (CDCl$_3$, 400 MHz) δ 7.41–7.38 (m, 6H), 7.29–7.25 (m, 6H), 6.60–6.57 (m, 1H), 4.68–4.56 (m, 1H), 3.18–3.14 (m, 2H), 2.89–2.80 (m, 1H), 2.74–2.52 (m, 2H), 2.43–2.36 (m, 1H), 2.32–2.19 (m, 1H), 2.12–2.07 (m, 2H), 1.83–1.80 (m, 2H), 1.60–1.53 (m, 1H), 1.45–1.40 (m, 27H); $^{13}$C (DEPT) (CDCl$_3$, 100 MHz) δ 129.4, 127.7, 126.4, 49.0, 48.7, 46.1, 42.5, 37.8, 37.6, 37.2, 31.6, 31.5, 29.6, 27.9, 27.8, 27.7, 26.3, 26.2, 26.0.

EXAMPLE 120

2-(2-Carboxymethyl-5-mercapto-pentanoylamino) succinic acid

To the protected thiolate of Example 119 in CH$_2$Cl$_2$ (1 mL) was added at 0° C. a solution of 60% TFA in CH$_2$Cl$_2$, containing 2% of ethanedithiol. Triisopropyl silane (1%) was then added and the reaction mixture was stirred at room temperature for 1 hour after which it was first concentrated using a stream of argon and then under vacuum. The obtained white solid was washed several times with a mixture of diethyl ether/hexanes (3:1). The obtained white solid was purified by semi-preparative HPLC to provide the desired compound.

EXAMPLE 121

3-(1-tert-Butoxycarbonyl-2-phenyl-ethylcarbamoyl)-6-tritylsulfanyl-hexanoic acid tert-butyl ester The same peptide coupling protocol as described for Example 119 was used and provided the title compound (70 mg, 100%): $^1$H NMR (CDCl$_3$, 400 MHz) δ 7.40–7.39 (m, 5H), 7.31–7.12 (m, 15H), 6.15 (d, 1H), 4.74–4.68 (m, 1H), 3.20–3.15 (m, 2H), 3.11–2.98 (m, 2H), 2.55–2.49 (dd, 1H), 2.44–2.29 (m, 1H), 2.24–2.16 (m, 1H), 2.12–2.05 (m, 2H), 1.84–1.81 (m, 2H),1.35 (4s, 18H); $^{13}$C (DEPT) (CDCl$_3$, 400 MHz) δ 129.5, 129.4, 129.3, 128.2, 127.7, 126.7, 126.4, 53.4, 53.3, 46.2, 46.1, 42.3, 42.2, 38.2, 38.1, 37.7, 37.5, 31.5, 31.4, 31.3, 29.6, 27.9, 27.8, 26.3, 26.2, 26.0, 25.9.

EXAMPLE 122

2-(2-Carboxymethyl-5-mercapto-pentanoylamino) succinic acid

The deprotection leading to the final product was the same as that of Example 120. Purification by semi-preparative HPLC gave the title compound as a white powder.

EXAMPLE 123

3-(Biphenyl-4-yl-ethylcarbamoyl)-2-phenethyl-pentanedioic acid

To an ice cooled solution of TFA (30%) in DCM (5 mL) containing water (5%) was added the compound of Example 55. The reaction mixture was stirred for 2 h at room temperature, after which time, the solvent was removed. The residue was triturated with ether and evaporated. The residue was partitioned between sodium hydroxide (1N) and ether. Following separation, the alkaline phase was acidified to pH 1 using HCl (1N) and extracted with ethyl acetate. The recombined organic layer was dried over sodium sulfate, filtered and evaporated. FAB: 460.1(MH$^+$), FAB(M–H$^+$): 458.0.

EXAMPLE 124

N-[1-tert-Butoxycarbonyl-2-(1H-indol-3-yl)-ethyl]-3-(methoxycarbonyl methyl-amino)-succinamic acid tert-butyl ester To a suspension of the dipeptide of Example 57 (100 mg, 0.23 mmol) in dry THF (2 mL) was added DIPEA (40 μL, 0.46 mmol). After the mixture became a homogenous solution, it was cooled to 0° C. and methyl bromoacetate (22 μL, 0.23 mmol) was introduced as a solution in dry THF (0.5 mL). The light suspension, which appeared shortly after, was stirred at 0° C. for 10 min and then at room temperature for 5 hours. The mixture was then concentrated in vacuum, dissolved in ethyl acetate and washed with H$_2$O and brine. Drying (Na$_2$SO$_4$) and evaporation gave the title compound (92 mg) as a yellow foam. Flash chromatography (CH$_2$Cl$_2$ to 5% methanol in CH$_2$Cl$_2$) gave the desired product in 62% yield: $^1$HNMR (CDCl$_3$, 300 MHz) □ 8.52 (br s, 1H), 7.82 (d, 1H), 7.59 (d, 1H), 7.38–7.02 (m, 4H), 4.75 (m, 1H), 4.18 (m, 1H), 3.68 (s, 3H), 3.61–3.21 (m and dd, 3H), 3.14 (dd, 1H), 2.85 (m, 2H), 1.42 (s, 9H), 1.36 (s, 9H); MS (Pos. FAB) 504.5 (MH)$^+$.

EXAMPLE 125

3-(2-Biphenyl-4-yl-ethylcarbamoyl)-4-trityloxycarbamoyl butyric acid tert-butyl ester Standard coupling between the building block of Example 63 and 2-biphenyl-4-yl-ethylamine gave the crude product. Silica gel chromatography of the crude using 20–40% ethyl acetate/n-hexanes afforded the desired product in 50% yield as a white solid.

$^1$H-NMR(CDCl$_3$, 400 MHz)□1.39(s, 9), 1.87–2.48(m, 4H), 2.76–2.87(m, 3H), 3.45(m, 2H), 6.32(d, 1H), 7.32(m, 15H), 7.43(m, 5H), 7.52–7.59(m, 4H), 7.82(d, 1H). FAB: 668.9(MH$^+$).

EXAMPLE 126

3-(2-Biphenyl-4-yl-ethylcarbamoyl)-4-hydroxycarbamoyl-butyric acid

Deprotection of the compound of Example 125 by standard procedures, followed by HPLC purification, gave the title compound. $^1$H-NMR (DMSO-d$_6$, 400 MHz): 1.98 (dd, 1H), 2.21(m, 2H), 2.44 (dd, 1H), 2.71 (t, 2H), 2.93 (m, 1H), 3.24 (dd, 2H), 7.31 (m, 3H), 7.44 (t, 2H), 7.57 (d, 2H), 7.62 (d, 2H), 8.77 (s, 1H), 8.80 (t, 1H), 10.42 (s, 1H); $^{13}$C-NMR (DMSO-d$_6$, 400 MHz, DEPT): 34.71, 35.4 29.3, 37.9, 40.2, 126.4, 127.2, 126.5, 128.9; FAB: 371(MH$^+$).

The compounds of Examples 127, 128–149 and 150 have all been prepared using the same methods as described for the compounds of Examples 125 and 126.

EXAMPLE 127

3-[2-(1H-Indol-3-yl)-ethylcarbamoyl]-4-trityloxycarbamoyl-butyric acid tert-butyl ester This compound was prepared by reacting the compound of Example of 63 with tyramine. $^1$H NMR (CDCl$_3$, 400 MHz):. 1.37(s, 9H), 1.39(s, 9H), 1.89–2.37(m, 4H), 2.84(m, 1H), 3.20(m, 2H), 4.69(m, 1H), 6.77(m, 1H), 7.23 (m, 21H), 8.25 (m, 1H); FAB: 731(MH$^+$).

EXAMPLE 128

4-Hydroxycarbamoyl-3-[2-(1H-indol-3-yl)-ethylcarbamoyl]-butyric acid

This compound was prepared by deprotection of the compound of Example 127.

EXAMPLE 129

3-[2-(4'-Cyano-biphenyl-4-yl)-ethylcarbamoyl]-4-trityloxycarbamoyl-butyric acid tert-butyl ester This compound was prepared by reacting the compound of Example 63 with the compound of Example 36.

EXAMPLE 130

3-[2-(4'-Cyano-biphenyl-4-yl)-ethylcarbamoyl]-4-hydroxycarbamoyl-butyric acid

This compound was prepared by deprotection of the compound of Example 129.

EXAMPLE 131

3-[2-(4-Pyridin-2-yl-phenyl)-ethylcarbamoyl]-4-trityloxycarbamoyl-butyric acid tert-butyl ester This compound was prepared by reacting the compound of Example 63 with the compound of Example 37.

EXAMPLE 132

4-Hydroxycarbamoyl-3-[2-(4-pyridin-2-yl-phenyl)-ethylcarbamoyl]-butyric acid

This compound was prepared by deprotection of the compound of Example 131.

EXAMPLE 133

3-(4-Phenyl-butylcarbamoyl)-4-trityloxycarbamoyl-butyric acid tert-butyl ester

This compound was prepared by reacting the compound of Example 63 with 4-phenyl butylamine.

EXAMPLE 134

4-Hydroxycarbamoyl-3-(4-phenyl-butylcarbamoyl)-butyric acid

This compound was prepared by deprotection of the compound of Example 133.

EXAMPLE 135

3-(2-Naphthalen-1-yl-ethylcarbamoyl)-4-trityloxycarbamoyl-butyric acid tert-butyl ester This compound was prepared by reacting the compound of Example 63 with the compound of Example 43.

EXAMPLE 136

4-Hydroxycarbamoyl-3-(2-naphthalen-1-yl-ethylcarbamoyl)-butyric acid

This compound was prepared by deprotection of the compound of Example 135.

EXAMPLE 137

3-(2-Phenoxy-ethylcarbamoyl)-4-trityloxycarbamoyl-butyric acid tert-butyl ester

This compound was prepared by reacting the compound of Example 63 with 2-phenoxy ethylamine.

EXAMPLE 138

4-Hydroxycarbamoyl-3-(2-phenoxy-ethylcarbamoyl)-butyric acid

This compound was prepared by deprotection of the compound of Example 137.

EXAMPLE 139

3-[2-(4'-Hydroxy-biphenyl-4-yl)-ethylcarbamoyl]-4-trityloxycarbamoyl-butyric acid tert-butyl ester This compound was prepared by reacting the compound Example of 63 with the compound of Example 38.

EXAMPLE 140

3-[2-(4'-Hydroxy-biphenyl-4-yl)-ethylcarbamoyl]-4-hydroxycarbamoyl-butyric acid

This compound was prepared by deprotection of the compound of Example 139.

EXAMPLE 141

3-(2,2-Diphenyl-ethylcarbamoyl)-4-trityloxycarbamoyl-butyric acid tert-butyl ester This compound was prepared by reacting the compound of Example 63 with the compound of Example 46.

EXAMPLE 142

3-(2,2-Diphenyl-ethylcarbamoyl)-4-hydroxycarbamoyl-butyric acid

This compound was prepared by deprotection of the compound of Example 141.

EXAMPLE 143

3-[2-(4'-Dimethylamino-biphenyl-4-yl)-ethylcarbamoyl]-4-trityloxycarbamoyl-butyric acid tert-butyl ester This compound was prepared by reacting the compound of Example 63 with the compound of Example 39.

EXAMPLE 144

3-[2-(4'-Dimethylamino-biphenyl-4-yl)-ethylcarbamoyl]-4-hydroxycarbamoyl-butyric acid This compound was prepared by deprotection of the compound of Example 143.

EXAMPLE 145

3-[2-(3',4'-Dimethoxy-biphenyl-4-yl)-ethylcarbamoyl]-4-trityloxycarbamoyl-butyric acid tert-butyl ester This compound was prepared by reacting the compound of Example 63 with the compound of Example 35.

EXAMPLE 146

4-Hydroxycarbamoyl-3-[2-(3',4'-dimethoxy-biphenyl-4-yl)-ethylcarbamoyl]-butyric acid This compound was prepared by deprotection of the compound of Example 145.

EXAMPLE 147

3-(5-Hydroxy-pentylcarbamoyl)-4-trityloxycarbamoyl-butyric acid tert-butyl ester This compound was prepared by reacting the compound of Example 63 with 5-amino-pentan-1-ol.

EXAMPLE 148

4-Hydroxycarbamoyl-3-(5-hydroxy-pentylcarbamoyl)-butyric acid

This compound was prepared by deprotection of the compound of Example 147.

EXAMPLE 149

3-[(Biphenyl-4-ylmethyl)-carbamoyl]-4-trityloxycarbamoyl-butyric acid tert-butyl ester This compound was prepared by reacting the compound of Example 63 with biphenylmethylamine.

EXAMPLE 150

3-[(Biphenyl-4-ylmethyl)-carbamoyl]-4-hydroxycarbamoyl-butyric acid

This compound was prepared by deprotection of the compound of Example 149.

EXAMPLE 151

3-(2-Biphenyl-4-yl-ethylcarbamoyl)-5-trityloxycarbamoyl-pentanoic acid tert-butyl ester To a solution of the compound of Example 66 (300 mg, 0.6 mmol) in anhydrous acetonitrile (3 mL) were successively added DIEA (528 µL, 3 mmol), 2-(4-biphenyl) ethylamine hydrochloride (280 mg, 1.2 mmol), and TBTU (234 mg, 0.72 mmol). The reaction mixture was stirred under argon for 24 h. The mixture was partitioned between brine and ethyl acetate. The aqueous phase was extracted several times with ethyl acetate. The recombined organic layer was extracted with HCl (1N, excess), brine, a saturated sodium bicarbonate solution, and brine followed by drying over sodium sulfate, filtration, and evaporation. The residue was flashed with 40% ethyl acetate/hexanes to give the product as a white solid. $^1$H NMR (CDCl$_3$, 400 MHz: 1.43(s, 9H); 1.57–1.81(m, 4H); 2.06(m, 1H); 2.36(m, 1H); 2.54(m, 1H); 2,82(m, 2H); 3.48(m, 2H); 6.16(d, J=32.1 Hz, 1H); 7.34(m, 15H); 7.42–7.60(m, 9H); 7.76(d, J=23.8 Hz, 1H).

EXAMPLE 152

3-(2-Biphenyl-4-yl-ethylcarbamoyl)-5-hydroxycarbamoyl-pentanoic acid

This compound was prepared by deprotection of the compound of Example 151, as previously described for the compound of Example 128.

EXAMPLE 153

3-(Biphenyl-4-yl-ethylcarbamoyl)-6-phenyl-4-trityloxycarbamoyl-hexanoic acid tert-butyl ester WSC.HCl (683 mg, 3.49 mmol) was dissolved in water (1 mL) and the pH was adjusted to 4.8. The compound of Example 55 (300 mg, 0.582 mmol) was dissolved in the same amount of THF and added to the former solution. O-Trityl hydroxylamine (505 mg, 1.746 mmol) was added and the mixture was stirred for 24 h. The reaction mixture was partitioned between HCl (0.5N, excess) and ethyl acetate. The water phase was extracted several times with ethyl acetate. The recombined organic layer was washed with brine, a saturated sodium hydrogen carbonate solution, and brine. The solvent was evaporated, following drying over sodium sulfate, and the crude was flashed with 30% ethyl acetate in hexanes. $^1$H NMR(CDCl$_3$, 400 MHz: 1.32(s, 9H); 1.50(m, 1H); 1.74(m, 1H); 2.32(m, 6H); 2.53(m, 2H); 3.46(m, 2H); 7.00(m, 1H); 7.16–7.57(m, 30H); FAB: 774 (MH$^+$).

EXAMPLE 154

3-(2-Biphenyl-4-yl-ethylcarbamoyl)-4-hydroxycarbamoyl-6-phenyl-hexanoic acid

This compound was prepared by deprotection of the compound of Example 153.

EXAMPLE 155

4-Benzyloxycarbamoyl-3-(2-biphenyl-4-yl-ethylcarbamoyl)-butyric acid tert-butyl ester A solution of the compound of Example 72 (0.90 g, 2.19 mmol) in anhydrous DMF (3 mL) was treated successively with DIEA (1.9 mL), O-benzyl hydroxylamine hydrochloride (706 mg, 4.38 mmol), and TBTU (1.02 g, 3.07 mmol). The reaction mixture was stirred for 24 h at room temperature. HCl (1M, excess) was added and the mixture was extracted several times with ethyl acetate. The recombined organic layer was washed with brine, dried over sodium sulfate, filtered and evaporated. The residue was flashed with 30% ethyl acetate in hexanes and the desired product was obtained as a white solid. $^1$H NMR(CDCl$_3$, 400 MHz: 1.42(s, 9H); 2.33(m, 2H); 2.45(m, 1H); 2.63(m, 1H); 2.82 (m, 2H); 3.03(m, 1H); 3.47(m, 2H); 4.87(m, 2H); 6.02(s, broad, 1H); 7.25(m, 2H); 7.34–7.45(m, 8H); 7.56(m, 4H).

EXAMPLE 156

3-(2-Biphenyl-4-yl-ethylcarbamoyl)-4-hydroxycarbamoyl-butyric acid

A solution of TFA in DCM (30%, 5 mL) containing water (5%) was prepared. The solution was cooled in an ice bath and then the compound of the Example 155 (200 mg, 0.387 mmol) was added. The reaction mixture was first stirred for 5 minutes at ° C., followed by 1 h at room temperature. The solvent was evaporated and the residue was triturated several times with ether and then evaporated. The residue was dissolved in wet methanol and hydrogenated using 10% Pd on charcoal. After 24 h, the reaction mixture was filtered over a celite pad and washed repeatedly with methanol. The filtrate was evaporated and then subjected to HPLC-purification.

EXAMPLE 157

3-(2-Biphenyl-4-yl-ethylcarbamoyl)-5-(bis-benzyloxy-phosphoryl)-pentanoic acid tert-butyl ester A solution of the compound of Example 77 (770 mg, 1.67 mmol) in anhydrous DMF (2 mL) was treated with DIEA (1.5 mL), 4-biphenylethyl amine (672 mg, 3.34 mmol), and TBTU (775 mg, 2.34 mmol). The reaction mixture was stirred for 24 h at room temperature after which HCl (1M, excess) was added. The mixture was extracted several times with ethyl acetate. The recombined organic layer was washed with brine, dried over sodium sulfate, filtered and evaporated. The residue was flashed with 50% ethyl acetate in hexanes and the desired product was obtained as a white solid. $^1$H NMR (CDCl$_3$, 400 MHz: 1.41(s, 9H); 1.61–1.87 (m, 4H); 2.15, 2.59(2dd, J$_1$=16.4 Hz. J$_2$=4.2 Hz, 2H); 2.67(m, 1H); 2.80(m, 2H); 3.49(m, 2H); 4.96(m, 4H); 6.35(t, J=5.6 Hz); 7.32(m, 13H); 7.42(m, 2H); 7.55(m, 4H); $^{31}$P NMR(CDCl$_3$, 400 MHz): 33.05.

EXAMPLE 158

3-(2-Biphenyl-4-yl-ethylcarbamoyl)-5-phosphono-pentanoic acid

This compound was prepared by deprotection of the compound of Example 157 using a procedure similar to that of the synthesis of the compound of Example 156.

EXAMPLE 159

N-[1-benzyloxycarbonyl-2-(1H-indol-3-yl)-ethyl]-3-[2-(diethoxy-phosphoryl)-4-phenyl-butyrylamino]-succinamic acid benzyl ester To a stirred solution of the peptide of Example 83 (536 mg, 1.00 mmol) in DMF (3 mL) was sequentially added phosphonoacetic acid 79 (1.00 mmol), HOBt (135 mg, 1.00 mmol) and PYBOP (520 mg, 1.00 mmol) at room temperature. DIPEA (523 µL, 3.00 mmol) was then added and the mixture was stirred at room temperature for 18 h. The reaction mixture was poured onto an aqueous solution of NaHCO$_3$ (5%) and extracted several times with ethyl acetate. The combined organic extracts were washed with NaHCO$_3$ (5%), H$_2$O, KHSO$_4$ (5%) and H$_2$O. Drying (Na$_2$SO$_4$) and evaporation gave the crude product (780 mg) as a light oil. Flash chromatography (SiO$_2$, ethyl acetate: hexane (2:1) to 100% ethyl acetate) gave a separable pair of diastereoisomers in a combined yield of 71%. The less polar diastereoisomer had the following spectroscopic data: $^1$H NMR (CDCl$_3$, 400 MHz) □ 8.03 (br d, 2H), 7.61 (br d, 1H), 7.40–7.11 (m, 19H), 6.82 (d, 1H), 5.15–4.82 (m, 5H), 4.87 (dd, 1H), 4.01 (m, 4H), 3.31 (d, 2H), 3.08 (dd, 1H), 2.78–2.43 (m, 4H), 2.35 (m, 1H), 2.00 (m, 1H), 1.26 (dt, 6H); $^{31}$P NMR (CDCl$_3$) δ 25.1; MS (Pos. FAB) 780.8 (M$^+$).

The more polar diastereoisomer had the following spectroscopic data: $^1$H NMR (CDCl$_3$, 400 MHz) □ 8.00 (br s, 1H), 7.58 (d, 1H), 7.39–7.17 (m, 19H), 6.84 (d, 1H), 5.15–4.98 (s and dd, 4H), 4.91 (m, 2H), 4.03 (m, 4H), 3.30 (d, 2H), 3.12 (dd, 1H), 2.65 (dd, 1H), 2.52 (m, 2H), 2.32–1.92 (m, 2H), 1.78 (br s, 1H), 1.25 (q, 6H); $^{31}$P NMR (CDCl$_3$) δ 24.6; MS (Pos. FAB) 780.8 (M$^+$).

EXAMPLE 160

N-[1-Carboxy-2-(1H-indol-3-yl)-ethyl]-3-(4-phenyl-2-phosphono-butyrylamino]-succinamic acid The more polar peptide phosphonate of Example 159 (54 mg, 69 µmol) was dissolved in dry CH$_2$Cl$_2$ (2 mL) followed by the addition of TMSBr (73 µL, 552 µmol). The resulting pale yellow solution was stirred for 40 h. The volatile materials were evaporated in vacuum at room temperature and the obtained residue was suspended in a water/methanol mixture (20:1) and vigorously stirred for 2 h after which it was lyophilized to give the crude phosphonic acid intermediate. This crude product was taken up in methanol (5 mL) and treated with Pd/C powder (10%, 25 mg). The mixture was stirred under an H$_2$ atmosphere (45 PSI) for 12 h and then the catalyst was removed by filtration through a celite pad. The resulting mixture was concentrated to give the crude title compound which was purified by HPLC.

EXAMPLE 161

N-[1-benzyloxycarbonyl-2-(1H-indol-3-yl)-ethyl]-3-[1-(dimethoxy-phosphoryl)-3-phenyl-propylamino]-succinamic acid benzyl ester To a stirred solution of H-AspTrp(OBn)-Trp(OBn) (536 mg, 1.00 mmol) in CH$_2$Cl$_2$ (4 ml) under argon atmosphere, was added DIPEA (175 µL, 1.00 mmol) followed by the addition of hydrocinnamaldehyde (158 µL, 1.2 mmol) and Na$_2$SO$_4$ (0.71 g, 5.00 mmol). The heterogeneous mixture was stirred at room temperature for 6 h and was filtered into another dry flask with the Na$_2$SO$_4$ cake being washed with CH$_2$Cl$_2$ (1 ml). The solution was maintained under argon while being cooled to 0° C. To this stirring solution was added trimethyl phosphate (208 µL, 1.76 mmol), followed by BF$_3$.Et$_2$O (150 µL, 1.20 mmol). The solution was allowed to warm slowly to ambient temperature and was further stirred for an additional 15 h. The reaction mixture was then diluted with CH$_2$Cl$_2$ and washed with ice-cold water. The organic extracts were dried (Na$_2$SO$_4$) and then concentrated to give 700 mg of a yellow foam. Purification by flash chromatography using a gradient of EtOAc in hexane (50% to 100%) provided a 1:1 mixture of diastereoisomers (0.31 g, 43%): $^1$H NMR (CDCl$_3$) δ 8.10 (s, 1H), 8.06 (d, 1H), 7.61 (d, 1H), 7.38–7.05 (m, 18H), 6.99 (d, 1H), 5.18–5.03(dd and s, 4H), 4.90 (dd, 1H), 3.68 (m, 1H), 3.63 (d, 3H), 3.55 (d, 3H), 3.33 (m, 2H) 2.90 (m, 1H), 2.75–2.52 (m, 4H), 2.01 (m, 2H), 1.75 (m, 2H); $^{31}$P NMR (CDCl$_3$) δ 29.6; MS (Pos. FAB) 725.4 (M$^+$).

EXAMPLE 162

N-[1-carboxy-2-(1H-indol-3-yl)-ethyl]-3-(3-phenyl-1-phosphono-propylamino)-succinic acid This compound was deprotected by catalytic hydrogenation using the same protocol as presented for the compound of Example 160. MS(Pos. FAB): 540(MNa$^+$).

EXAMPLE 163

N-[1-Benzyloxycarbonyl-2-(1H-indol-3-yl)-ethyl]-3-{[benzyloxy-(4-phenyl-butyl)-phosphinoyl]-amino}-succinamic acid benzyl ester To a stirred solution of the phosphinate of Example 81 (144 mg, 0.50 mmol) in dry degassed acetonitrile (1.5 mL), was added bis-(trimethylsilyl)acetamide (73 μL, 0.30 mmol) followed immediately by the addition of a solution of H-Asp(OBn)-Trp(OBn), [Example 83 (322 mg, 0.60 mmol)] and Et$_3$N (209 μL, 1.5 mmol) in CCl$_4$/CH$_3$CN (3:1, 2 mL). The reaction mixture was stirred at room temperature for 14 h and then concentrated in vacuum. Purification by flash chromatography using a gradient of EtOAc in hexane (50% to 100%) provided the title compound (0.175 g, 44%) as a white residue: R$_f$ (100% EtOAc)=0.5; $^1$H NMR (CDCl$_3$) δ 8.5 (d, 1H), 7.6 (d, 1H), 7.5–6.9 (m, 25), 5.2–4.9 (m, 6H), 4.83 (dd, 1H), 4.63 (dd, 1H), 4.22 (m, 1H), 3.91(d, 1H), 3.36 (dt, 1H), 3.28 (dt,1H), 3.01 (dd, 1H), 2.65 (dt, 1H), 2.50 (m, 2H), 1.71–1.25 (m, 6H); $^{31}$P NMR (CDCl$_3$) δ 35.6.

EXAMPLE 164

N-[1-Carboxy-2-(1H-indol-3-yl)-ethyl]-3-{[hydroxy-(4-phenyl-butyl)-phosphinoyl]-amino}-succinamic acid This compound was prepared using catalytic hydrogenation, following the same protocol as presented above for the compound of Example 160. MS(Pos. FAB): 538(MNa$^+$).

EXAMPLE 165

(5-tert-Butoxycarbonylmethyl-2,2-dimethyl-4,6-dioxo-[1,3] dioxan-5-yl)-acetic acid tert-butyl ester To a solution of 2,2-dimethyl-1,3-dioxane-4,6-dione (5 g, 33 mmol) in chloroform (100 mL) was added potassium carbonate (27.6 g, 120 mmol) and benzyltriethylammoniumchloride (16.6 g, 120 mmol). The reaction mixture was stirred for 15 minutes and then treated drop wise with a solution of tert-butyl bromoacetate (18 mL, 120 mmol) in chloroform (50 mL). The resultant mixture was stirred for 5 h at 50° C. After cooling to room temperature, water was added (100 mL). After shaking, the organic phase was separated and the water phase was extracted two times with chloroform. The recombined organic layer was washed with brine, dried over sodium sulfate, filtered and evaporated. The resultant light yellow solid was dissolved in ether (50 mL) and washed several times with water followed by drying over sodium sulfate, filtration, and evaporation. Most of the solvent was evaporated and the residue was triturated with hexanes (20 mL). After about 30 minutes standing at room temperature, crystallization of the desired product began. The mixture was refrigerated. After 24 h, the product was filtered and washed with ice cold ether followed by drying under high vacuum. $^1$H NMR(CDCl$_3$, 300 MHz): 1.39(s, 18H); 1.90(s, 6H); 2.95(s, 4H).

EXAMPLE 166

3,3-Dicarboxy-pentanedioic acid di-tert-butyl ester

The compound of Example 165 (200 mg, 0.54 mmol) was dissolved in a mixture of THF(10 mL) and water (2 mL). Lithium hydroxide monohydrate (46 mg, 1.07 mmol) was added and the mixture was stirred for 24 h at room temperature. The solvent was evaporated and the residue was dissolved in water (5 mL) and extracted with ether. The water phase was acidified by HCl to pH1 and extracted with ethyl acetate. After drying over sodium sulfate, filtration and evaporation, the solvent was evaporated to dryness. $^1$H NMR(CDCl$_3$, 300 MHz): 1.43(s, 18H); 3.10(s, 4H).

EXAMPLE 167

3-Carboxy-pentanedioic acid di-tert-butyl ester

The compound of Example 166 (170 mg, 0.512 mmol) was dissolved in ethyl acetate. Formic acid (61 μL, 1.53 mmol) was added and the mixture was heated at 80° C. for 3 h. After cooling to room temperature, the reaction mixture was extracted three times with water, dried (sodium sulfate), filtered and evaporated to dryness. $^1$H NMR(CDCl$_3$, 300 MHz): 1.43(s, 18H); 2.50, 2.65(2dd, J$_1$=16.7 Hz, J$_2$=6.2 Hz, 4H); 3.20(p, J=6.2 Hz, 1H).

EXAMPLE 168

3-(2-Naphthalen-2-yl-ethylcarbamoyl)-pentanedioic acid di-tert-butyl ester

A solution of the compound of Example 166 (144 mg, 0.5 mmol) in anhydrous DMF (2 mL) was treated successively with triethylamine (92 μL, 0.65 mL), the compound of example 43 (140 mg, 0.6 mmol), DIC(96 μL, 0.6 mmol), and HOBt (82 mg, 0.6 mmol). The reaction mixture was stirred for 24 h at room temperature. HCl (1M, excess) was added and the mixture was extracted several times with ethyl acetate. The recombined organic layer was washed with brine, dried over sodium sulfate, filtered and evaporated. The residue was flashed with 20–25% ethyl acetate in hexanes and the desired product was obtained as a white solid. $^1$H NMR(CDCl$_3$, 300 MHz1.40(s, 18H); 2.31, 2.62 (2dd, J$_1$=16.5 Hz, J$_2$=4.2 Hz, 4H); 2.96(m, 3H); 3.59(m, 2H); 6.25(m, 1H); 7.34–7.49(m,3H); 7.69(s, 1H); 3.82(m, 3H).

EXAMPLE 169

3-(2-Naphthalen-2-yl-ethylcarbamoyl)-pentanedioic acid

Deprotection of the compound of example 168 by standard procedure followed by HPLC purification gave the title compound.

General Procedure to Determine PHEX Enzymatic Activity

The soluble form of the metallopeptidase PHEX (sPHEX) was purified to homogeneity according to the methods of Boileau and Crine (WO 00/50580). sPHEX quantity was measured with the Bradford assay (BioRad) using BSA as a standard.

EXAMPLE 170

Determination of sPHEX Enzymatic Activity sPHEX enzymatic activity was determined using an HPLC method (WO 00/50580).

EXAMPLE 171

Determination of sPHEX Activity Using a Fluorogenic Substrate sPHEX activity was determined using a fluorogenic substrate in which an increase of fluorescence was proportional to substrate conversion to products.

Three fluorogenic substrates were proven to be particularly good sPHEX substrates: Abz-GFRDWK-Dnp (S1), Abz-DHLSDTSTQ-edDnp (S2) and Abz-GFSDYK-Dnp (S3). sPHEX showed the best kinetic parameters for S3 that was therefore the commonly used substrate. S3 was synthesized at Dr. Gilles Lajoie's laboratories (University of Western Ontario, Canada) by standard solid phase peptide synthesis. The fluorescent reaction product was excited at 320 nm to fluoresce at 420 nm. Fluorescence was recorded at 420 nm every five minutes over a one-hour period on a fluorescence plate reader (Perkin-Elmer, HTS-7000) to calculate the initial rate of the reaction. Typically, the reaction was carried out in 200 µl of buffer M (50 mM Mes(NaOH) pH 6.5, 150 mM NaCl) containing 100 ng of purified sPHEX and 20 µM of fluorigenic substrate to initiate the reaction. Enzymatic activity was determined by subtracting either the initial rate of substrate in buffer (solvolysis), or the typical reaction rate in which 5 mM EDTA was added prior to initiating the reaction.

sPHEX inhibitor IC50 determinations were done using the tested inhibitor at various concentrations coming from a serial dilution (usually ranging from $10^{-3}$ M to $10^{-12}$ M) in the reaction described above. IC50 values were calculated using the iterative four parameters non-linear regression formula from the GraphPad™ software (Prism).

To establish the relationship between recorded fluorescence and molar yield of the enzymatic reaction, a standard curve of fluorescence versus the concentration of the reaction fluorescent adduct was established by measuring the fluorescence of the Abz-GFS peptide at different concentration in buffer M.

The assessment of sPHEX biological activity using one of the above-mentioned substrates, or another one, need not be limited to an enzymatic activity of sPHEX. In accordance with one embodiment, the binding of sPHEX to at least one of its substrates, and in particular one of S1, S2 and S3 could be carried-out. Such determination of sPHEX biological activity could provide the means to screen and identify modulators of sPHEX biological activity (e.g. binding, enzymatic activity and otherwise).

In accordance with such embodiment, there is provided a kit for screening and identifying sPHEX modulation of sPHEX biological activity comprising a sPHEX and a sPHEX substrate selected from the group consisting of S1, S2 and S3.

Abbreviations used: Abz: aminobenzoic acid; Dnp: dinitrophenyl; edDnp: ethylenediamine-Dnp; G: glycine; F: phenylalanine; R: arginine; D: aspartic acid; W: tryptophan; K: lysine; H: histidine; L: leucine; S: serine; T: threonine; Q: glutamine; Y: tyrosine; BSA: bovine serum albumin; IC50: inhibitor concentration at which 50% of the enzyme is inhibited.

The following table (Table 1) lists a series of exemplary compounds as described herein as well as their respective biological activity ($IC_{50}$).

TABLE 1

Exemplary in vitro activity.

| Identification (Example No) | Structure | $IC_{50}$ (µM) |
|---|---|---|
| 87 | 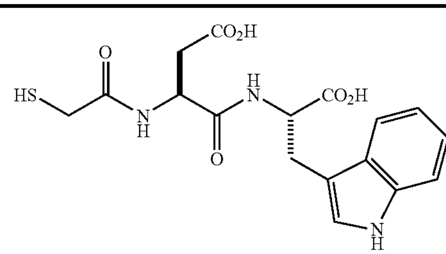 | 0.600 |
| 89 | 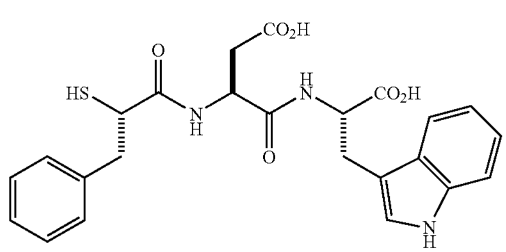 | 0.011 |

TABLE 1-continued

Exemplary in vitro activity.

| Identification (Example No) | Structure | IC$_{50}$ (μM) |
|---|---|---|
| 90 | HS-CH(CH$_3$)-C(O)-NH-CH(CH$_2$CO$_2$H)-C(O)-NH-CH(CH$_2$-indolyl)-CO$_2$H | 0.068 |
| 91 | HS-CH(CH$_2$CH(CH$_3$)$_2$)-C(O)-NH-CH(CH$_2$CO$_2$H)-C(O)-NH-CH(CH$_2$-indolyl)-CO$_2$H | 0.094 |
| 92 | HS-CH(CH(CH$_3$)$_2$)-C(O)-NH-CH(CH$_2$CO$_2$H)-C(O)-NH-CH(CH$_2$-indolyl)-CO$_2$H | 0.005 |
| 93 | HS-CH(CH$_2$OH)-C(O)-NH-CH(CH$_2$CO$_2$H)-C(O)-NH-CH(CH$_2$-indolyl)-CO$_2$H | 0.048 |
| 94 | HS-CH(CH(OH)CH$_3$)-C(O)-NH-CH(CH$_2$CO$_2$H)-C(O)-NH-CH(CH$_2$-indolyl)-CO$_2$H | 0.004 |
| 95 | HS-CH(n-butyl)-C(O)-NH-CH(CH$_2$CO$_2$H)-C(O)-NH-CH(CH$_2$-indolyl)-CO$_2$H | 0.007 |

TABLE 1-continued

Exemplary in vitro activity.

| Identification (Example No) | Structure | IC$_{50}$ (µM) |
|---|---|---|
| 96 | (structure) | 0.004 |
| 97 | (structure) | 0.003 |
| 98 | (structure) | 0.008 |
| 99 | (structure) | 0.008 |
| 100 | (structure) | 0.006 |
| 101 | (structure) | 0.018 |

TABLE 1-continued

Exemplary in vitro activity.

| Identification (Example No) | Structure | IC$_{50}$ (μM) |
|---|---|---|
| 102 | HS-CH(CH$_2$-cyclohexyl)-C(O)-NH-CH(CH$_2$CO$_2$H)-C(O)-NH-CH(CH$_2$-indol-3-yl)-CO$_2$H | 0.020 |
| 103 | HS-CH(CH$_2$-indol-3-yl)-C(O)-NH-CH(CH$_2$CO$_2$H)-C(O)-NH-CH(CH$_2$-indol-3-yl)-CO$_2$H | 0.022 |
| 104 | HS-CH(CH$_2$-naphth-2-yl)-C(O)-NH-CH(CH$_2$CO$_2$H)-C(O)-NH-CH(CH$_2$-indol-3-yl)-CO$_2$H | 0.015 |
| 106 | HS-CH(CH$_2$-Ph)-C(O)-NH-CH(CH$_2$CO$_2$H)-C(O)-NH-CH(CH$_2$-naphth-2-yl)-CO$_2$H | 0.006 |
| 107 | HS-CH(CH$_2$-Ph)-C(O)-NH-CH(CH$_2$CO$_2$H)-C(O)-NH-CH(CH$_2$OH)-CO$_2$H | 0.170 |
| 108 | HS-CH(CH$_2$-Ph)-C(O)-NH-CH(CH$_2$CO$_2$H)-C(O)-NH-CH(CH$_2$-C$_6$H$_4$-4-OH)-CO$_2$H | 0.007 |

TABLE 1-continued

Exemplary in vitro activity.

| Identification (Example No) | Structure | IC$_{50}$ (μM) |
|---|---|---|
| 109 | HS-CH(CH2Ph)-C(O)-NH-CH(CH2CO2H)-C(O)-NH-CH(CH2Ph)-CO2H | 0.007 |
| 110 | HS-CH(CH2Ph)-C(O)-NH-CH(CH2CO2H)-C(O)-NH-CH(CH2-C6H4-Ph)-CO2H | 0.038 |
| 111 | HS-CH(CH2Ph)-C(O)-NH-CH(CH2CO2H)-C(O)-NH-CH(CH2Ph)-CH2OH | 0.090 |
| 112 | HS-CH(CH2Ph)-C(O)-NH-CH(CH2CO2H)-C(O)-NH-CH(CH2-indolyl)-CO2H | 0.015 |
| 114 | HS-CH(CH2Ph)-C(O)-NH-CH(CH2CH2CO2H)-C(O)-NH-CH(CH2-indolyl)-CO2H | 0.320 |
| 115 | HS-CH2-C(O)-NH-CH(CH2CO2H)-C(O)-NH-CH(CH2-indolyl)-CONHMe | 1.3 |

TABLE 1-continued

Exemplary in vitro activity.

| Identification (Example No) | Structure | IC$_{50}$ (μM) |
|---|---|---|
| 116 | 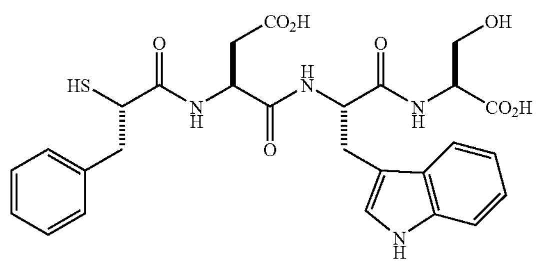 | 0.004 |
| 117 | 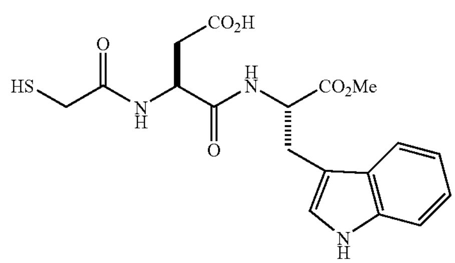 | 2.6 |
| 118 | 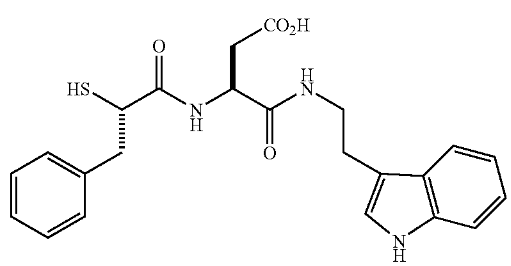 | 0.140 |
| 126 | 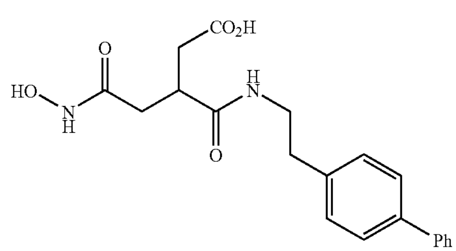 | 0.017 |
| 130 | 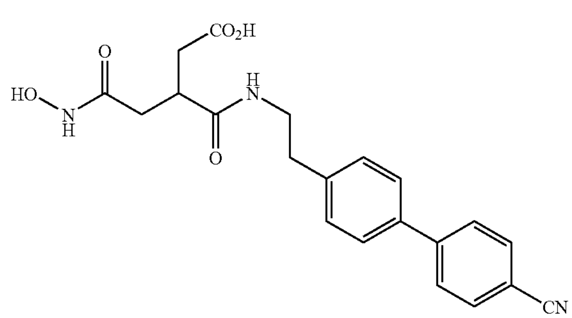 | 0.190 |

TABLE 1-continued

Exemplary in vitro activity.

| Identification (Example No) | Structure | IC$_{50}$ (µM) |
|---|---|---|
| 132 | HO-NH-C(O)-CH$_2$-CH(CH$_2$CO$_2$H)-C(O)-NH-CH$_2$CH$_2$-(4-(2-pyridyl)phenyl) | 0.240 |
| 134 | HO-NH-C(O)-CH$_2$-CH(CH$_2$CO$_2$H)-C(O)-NH-(CH$_2$)$_4$-Ph | 0.560 |
| 138 | HO-NH-C(O)-CH$_2$-CH(CH$_2$CO$_2$H)-C(O)-NH-CH$_2$CH$_2$-OPh | 0.860 |
| 140 | HO-NH-C(O)-CH$_2$-CH(CH$_2$CO$_2$H)-C(O)-NH-CH$_2$CH$_2$-(4'-hydroxybiphenyl-4-yl) | 0.360 |
| 142 | HO-NH-C(O)-CH$_2$-CH(CH$_2$CO$_2$H)-C(O)-NH-CH$_2$-CH(Ph)$_2$ | 0.054 |

TABLE 1-continued

Exemplary in vitro activity.

| Identification (Example No) | Structure | IC$_{50}$ (µM) |
|---|---|---|
| 144 | 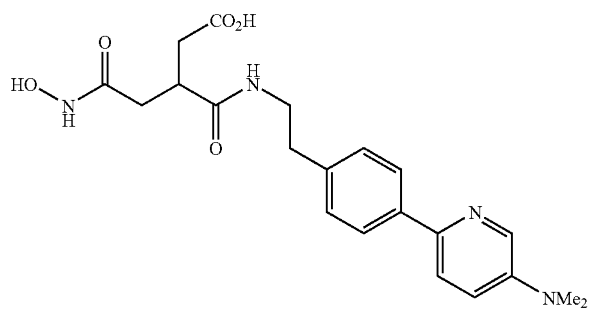 | 5.0 |
| 148 | 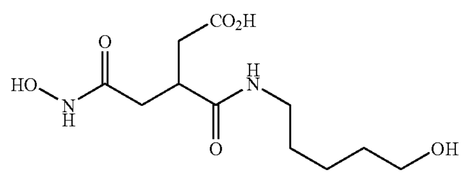 | 1.7 |
| 150 | 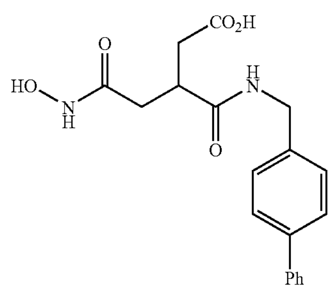 | 0.270 |
| 152 | 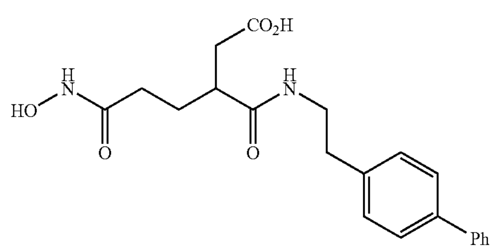 | 1.3 |
| 162 | 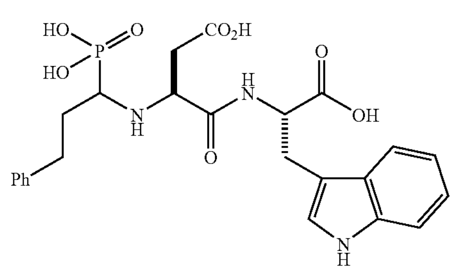 | 9.7 |
| 169 | 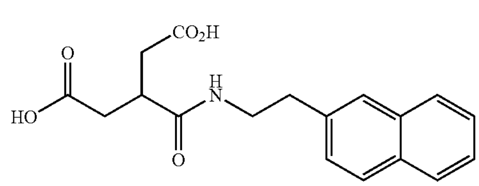 | 19 |

General Procedure to Monitor Protection of a PHEX Substrate by a PHEX Inhibitor.

EXAMPLE 172

Inhibition of sPHEX

In general, in order to show inhibition of sPHEX, the enzyme is incubated in the absence or the presence of the inhibiting compound, and a substrate is added in conditions that are suitable for sPHEX enzymatic activity. Hydrolysis of the substrate in the absence or the presence of the inhibiting compound is monitored.

For example, 1.0 µg of purified sPHEX was first incubated at 37° C. for 15 min with or without $1\times10^{-5}$M of compound MH-2-64C (FIG. 1) in 90 µl 50 mM MES (2-(N-morpholino)ethanesulfonic acid) pH 6.5, 150 mM NaCl. Then, 2.5 µg of peptide $PTHrP_{107-139}$ in 10 µl of the same buffer were added and the incubation continued for 30 min. The reaction mixture also contained 1.3 µg of the amino acid Phe which was used as an internal standard. After the incubation period, the reaction was stopped by the addition of EDTA to a final concentration of 5 mM. Detection of cleavage products was performed by reverse phase high performance liquid chromatography (RP-HPLC) on a C18 µBondapak™ analytical column (Waters, Mississauga, ON, Canada) with a UV detector set at 220 nm. Peptides were resolved with a linear gradient of 10% to 50% mobile phase B in 15 min at 40° C. with a flow rate of 1.0 ml/min [mobile phase A=0.1% trifluoroacetic acid; mobile phase B=80% acetonitrile ($CH_3CN$), 0.1% trifluoroacetic acid]. Results were quantified by comparing the area under the undigested peak of $PTHrP_{107-139}$, after normalization for the amount of Phe present in the sample.

Figure 2:
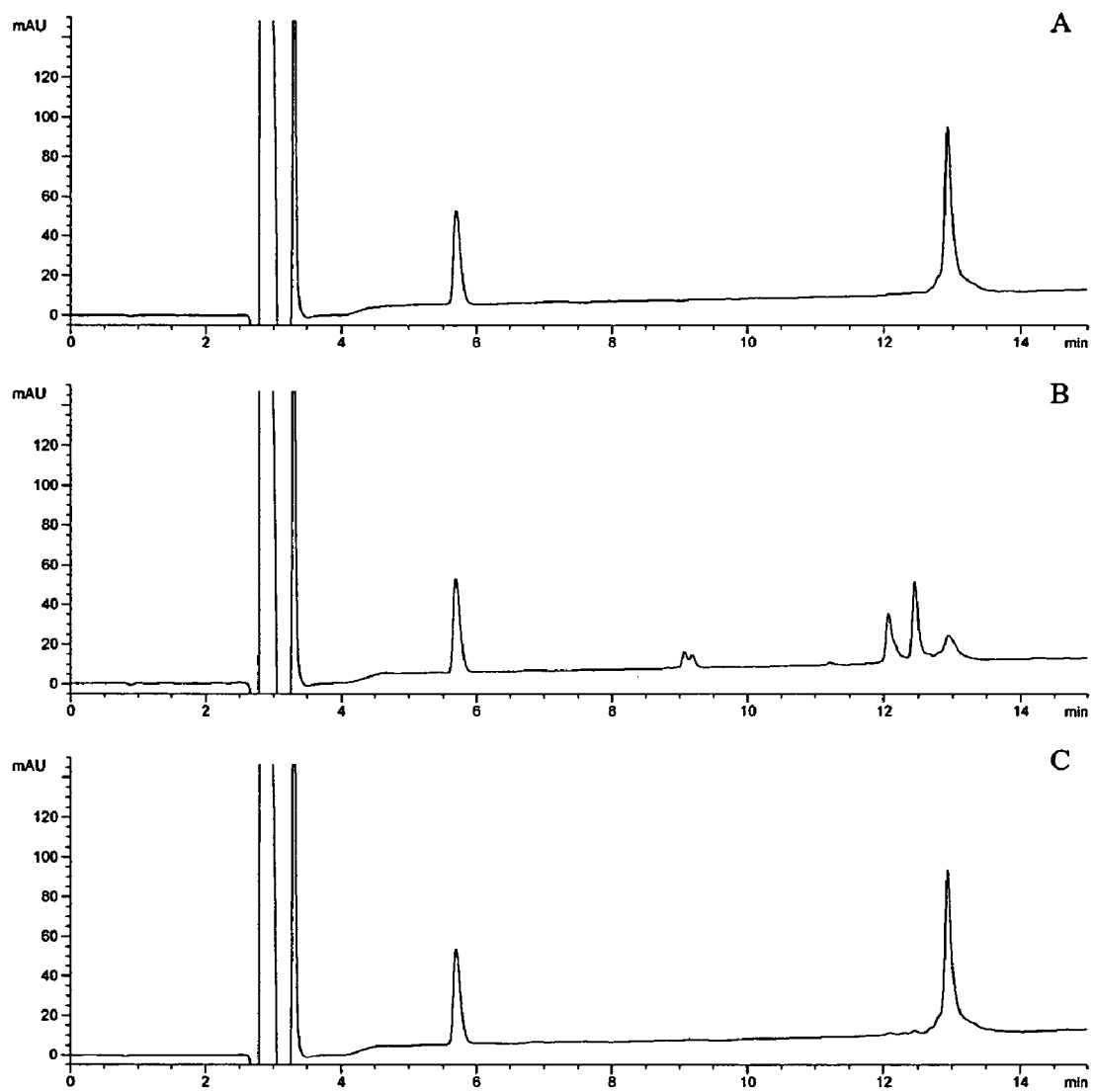
FIG. 2 illustrates in vitro protection of PHEX substrate PTHrP(107-132) by inhibitor MH-2-64C (compound of Example 126)

In the absence of sPHEX, no digestion of $PTHrP_{107-139}$ (elution time 12.9 min) was evident (FIG. 2A). In the presence of sPHEX, however, degradation of approximately 75% of the peptide was observed (FIG. 2B). (The peak eluting at 5.7 min corresponds to the Phe used as internal standard). Digestion of $PTHrP_{107-139}$ by sPHEX resulted in the production of four degradation products eluted at 9.1, 9.2, 12.1, and 12.5 min (FIG. 2B). In the presence of compound MH-2-64C (compound of Example 126), a PHEX inhibitor, degradation of $PTHrP_{107-139}$ was fully prevented (FIG. 2C). It can be concluded that a PHEX inhibitor can protect a PHEX substrate from degradation and thus be useful in the identification of such substrates.

General Procedure to Test the Effects of PHEX Inhibitor on Mineralization by Cultured Cells.

EXAMPLE 173

Stimulation of Mineralization in Cultured Cells by PHEX Inhibitors

In general, to show stimulation of mineralization in cultured cells by PHEX inhibitors, cells of osteoblast lineage are incubated in conditions that favors the mineralization process in the absence and the presence of the PHEX inhibiting compound. This cellular model is used to study osteoblasts proliferation and differentiation, and to follow the mineralization process.

Mineralization can be monitored by standard techniques such as von Kossa staining or 45Ca incorporation in the extracellular matrix.

For example, cells were enzymatically isolated from the calvaria of 21-day old Wistar rat fetuses by sequential digestion with collagenase as described previously (Bellows et al., 1986). Cells obtained from the last four of the five digestion steps were plated in T-75 flasks in α-MEM containing 15% FBS (Cansera) and antibiotics comprising 100 µg/ml penicillin G (Sigma-Aldrich), 50 µg/ml gentamycin (Life Technologies), and 0.3 µg/ml fungizone (Life Technologies). After 24 h incubation, attached cells were washed with PBS to remove nonviable cells and other debris, and then collected by trypsinization using 0.2% trypsin in citrate saline. Cells were plated in 12-well plates at $9.0\times10^3$ cells/well in α-MEM containing 10% FBS and antibiotics. After 24 h incubation, the medium was changed and supplemented with 50 µg/ml ascorbic acid, 10 mM sodium β-glycerophosphate and $1\times10^{-8}$M dexamethasone (day 1). Cells were treated with varying concentrations of PHEX inhibitor or vehicle from day 1 to 25 of culture. Medium was changed every 2–3 days. All dishes were incubated at 37° C. in a humidified atmosphere in 95% air 5% $CO_2$ incubator.

At day 18, 21 and 25 of rat calvaria osteoblasts culture, mineralization was determined by $^{45}$Ca incorporation assay as described previously (Ecarot et Desbarats, 1999). Culture medium was replaced by fresh □-MEM medium containing 10% FBS, 1 □Ci/ml $^{45}CaCl_2$ (5–30 Ci/g Ca, ICN), and varying concentrations of PHEX inhibitor or vehicle. Cells were labelled for 5 h at 37° C. in a humidified atmosphere in 95% air 5% $CO_2$ incubator. Labelling medium was then removed and cells were incubated with unlabeled culture medium for 15 min and rinsed three times with 0.9% NaCl. Cell layers were solubilized in 12.5% trichloroacetic acid and aliquots counted for radioactivity.

Figure 3:
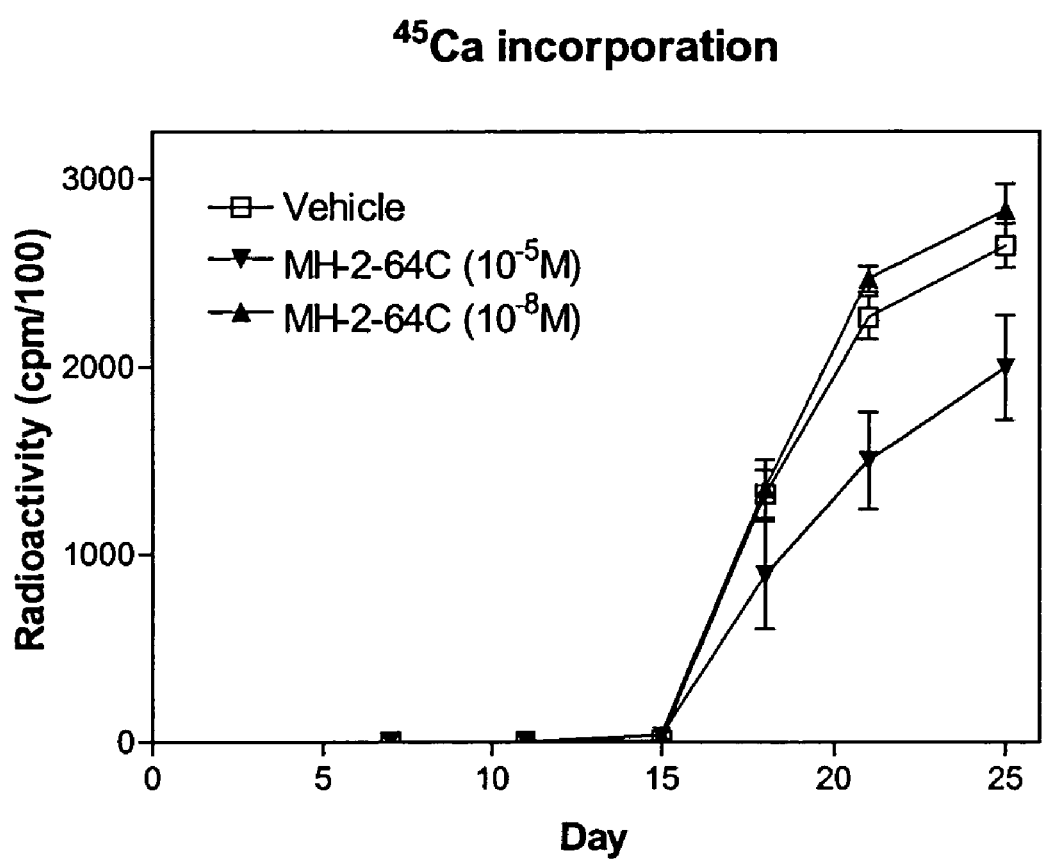
FIG. 3 illustrates the effect of adding decreasing concentrations of the PHEX inhibitor MH-2-64C (compound of Example 126) to a culture medium of primary rat calvaria osteoblasts, on mineralization.

When cultured in the conditions described above, fetal rat calvaria cells show incorporation of $^{45}$Ca in the extracellular matrix around day 15 (FIG. 3). The addition of the PHEX inhibitor MH-2-64C (compound of Example 126) at a concentration of $1\times10^{-5}$M, a concentration that totally inhibits PHEX, reduced significantly $^{45}$Ca incorporation by the cells (FIG. 3), suggesting that the mineralization process has been negatively affected by this compound. This result is consistent with reports that cultured osteoblasts from the Hyp mouse, that lack an active PHEX protein (Beck et al. 1997), show impaired mineralization (Nesbitt et al. 1999). Surprisingly, lower concentrations of PHEX inhibitor significantly stimulated the incorporation of $^{45}$Ca by the cultured cells (FIG. 3). A biphasic effect of the inhibitor on the $^{45}$Ca incorporation rate was therefore observed: at high dose ($10^{-5}$ M) an inhibition of mineralization was observed whereas a low dose ($10^{-6}$ M) (Data not shown) of inhibitor increased the mineralization rate. These results suggest that low doses of PHEX inhibitors could be used to stimulate the mineralization process.

General Procedure to Show Stimulation of Bone Lesion Repair in the Presence of Low Doses of PHEX Inhibitor.

EXAMPLE 174

Osteogenic Properties of PHEX Inhibitors

Osteogenic properties of PHEX inhibitors can be shown in a model of rat mandibular defect. For example, a 2 mm size bone defect was created in the rat mandible as described previously (Vu et al., 1999). Rats were anesthetized and the vestibular surface of the right mandibular ramus was exposed as follow: an incision was made through the skin along an imaginary line forming a 90° angle with the lower lip to access the muscle layer. A scalpel blade was used to make an incision parallel to the fibers of the deep portion of masseter muscle, about 2 mm posterior to the facial artery (largest branch of the external carotid), in the portion where it gives rise to the labial mandibular artery. The periosteum was elevated and the underlying bony surface exposed. A 2 mm×2 mm bony window was drilled between the second and third molar using a slow-speed dental drill with a carbide round burr size 1.4 mm (Brasseler) and a drill size 2 mm (Straumann Canada Ltd). Saline irrigation was used during the drilling. Porous hydroxyapatite particles (Fin-Ceramica Faenza s.r.l.) with pore size ranged from 450 to 600 µm were accommodated in the bony hole and pushed into it. The particles had been incubated previously in solutions of varying concentrations of PHEX inhibitor or vehicle for 16 to 24 hours at 4° C. Once the bony window was filled the lesion was covered with a membrane of hydroxyapatite (Fin-Ceramica Faenza s.r.l.) which was fixed to the surrounding bone surface with topical tissue adhesive. The muscle fibers were carefully repositioned on the mandible and sutured with absorbable surgical sutures (Chromic Gut, Ethicon Inc.). The skin was sutured for total coverage with silk sutures (Sherwood Davis & Geck, Wayne). After 7 days of treatment the bone lesion was exposed and varying concentrations of PHEX inhibitor or vehicle was reapplied to hydroxyapatite particles. Treatment was continued for another 7 days.

After the 14 day healing period, bone formation at the defect was evaluated by scanning electron microscopy and microcomputed tomography. Animals were sacrificed by intravascular perfusion through the left ventricle with 4% paraformaldehyde and 0.1% glutaraldehyde solution. Treated hemimandibles were taken, immersed in the fixative overnight at 4° C. then washed and kept in 0.1 M cacodylate buffer pH 8.0 until analysis. Specimens for quantification by scanning electron microscopy were dehydrated in a graded alcohol series and embedded in LR White resin (Marivac) for further sectioning along their longitudinal axis. Computerized images of the sections were acquired using a JEOL, JSM-6460 LV scanning electron microscope operated in the backscattered mode at 20 kV. Amount of bone tissue present in the sections was quantified by manual tracing using the MOP-3 system (Carl Zeiss) and was expressed as a percentage of the total defect area.

Figure 4:
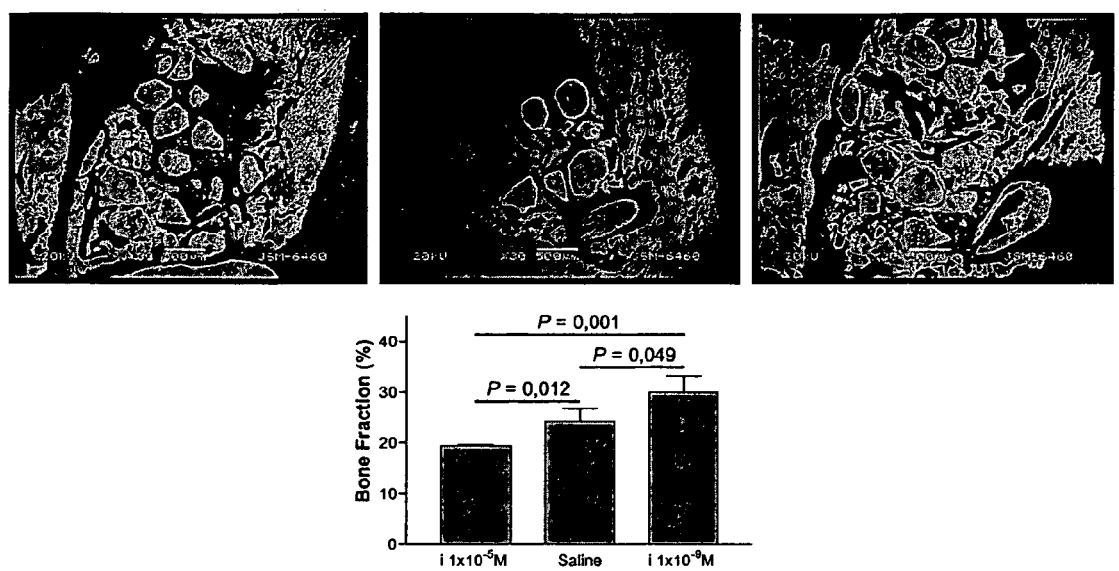
FIG. 4 represents scanning electron microscopy pictures of lesions in rat mandibles repaired in the presence or the absence of the PHEX inhibitor MH-2-64C (compound of Example 126), as well as illustrating quantification of bone fraction.
Figure 5:
FIG. 5 illustrates a 3D-reconstruction by micro computed tomography of lesions in the rat mandibles, repaired in the presence or the absence of the PHEX inhibitor MH-2-64C (compound of Example 126) presented in FIG. 4.

Analysis of the defects treated with implant of porous hydroxyapapatite in absence of PHEX inhibitor show bone formation after 14 days of healing (FIG. 4). The addition of the PHEX inhibitor MH-2-64C (compound of Example 126) to hydroxyapatite particles at a concentration of $1\times10^{-5}$ M, a concentration that totally inhibits PHEX, reduced significantly bone formation compared to saline (FIG. 4) suggesting that the rate of healing has been negatively affected by this compound. On the contrary, lower concentrations of PHEX inhibitor significantly stimulated bone formation (FIG. 4). These results are consistent with the observation that PHEX inhibitors have a biphasic effect on mineralization by cultured cells, and also suggest that low doses of PHEX inhibitors could be used in vivo as osteogenic agents in order to stimulate the bone healing process. These findings are supported by microcomputed tomography measurements made on one representative specimen from each group (FIG. 5). 3D reconstruction pictures of defect implanted with hydroxyapatite particles in presence of a high or a low dose of PHEX inhibitor show more bone around particles soaked in low dose of inhibitor than around particles soaked in saline. Again, a high inhibitor dose reduced bone formation. These observations strengthen the use of a low dose of PHEX inhibitor as an osteogenic agent in medical applications.

General Procedure to Use PHEX Inhibitors as Therapeutics.

EXAMPLE 175

Effect of a PHEX Inhibitor of the Present Invention on Circulating Phosphate

The administration of a therapeutically effective amount of a PHEX inhibitor of the present invention induces a normalization of circulating phosphate, thus reducing, or preferably preventing, hyperphosphatemia or hyperparathyroidism and the appearance of their consequences. Table 2 below lists examples of causes of hyperphosphatemia.

TABLE 2

| Causes Of Hyperphosphatemia |
|---|
| Binding to serum proteins |
| Plasma cell dyscrasias |
| Decreased renal excretion |
| Renal insufficiency |
| Hypoparathyroidism |
| Pseudohypoparathyroidism, types I and II |
| Tumoral calcinosis |
| Pseudoxanthoma elasticum |
| Infantile hypophosphatasia |
| Hyperostosis |
| Hyperthyroidism |
| Growth hormone activity |
| Adrenal insufficiency |
| Bisphosphonate therapy |
| Increased intestinal absorption |
| Phosphorus-containing cathartics |
| Vitamin D ingestion |
| Granulomatous diseases producing vitamin D |
| Sarcoidosis |
| Tuberculosis |
| Internal redistribution |
| Acute metabolic acidosis |
| Lactic acidosis |
| Acute respiratory acidosis |
| Lactic acid infusion |
| Reduced insulin level |
| Clonidine administration |
| Cellular release |
| Rhabdomyolysis |
| Organ infarction |
| Tumor lysis |
| Burkitt's lymphoma |
| Lymphoblastic lymphoma |
| Metastatic small cell carcinoma |
| Thyrotoxicosis |
| Acute hemolysis |
| Parenteral administration |
| Intravenous phosphate salts |
| Lipid (phospholipid) infusion |
| Spurious hyperphosphatemia |
| Thrombocytosis |
| Hyperlipidemia |

The PHEX inhibitors are administered to rats weighing about 250 g at a dose of 10 mg/kg. The control group consists of another group of rats where the same vehicle is administered but without the PHEX inhibitor. Serum and urine are obtained from the test animals using standard methods. The phosphate concentration in both serum and urine is measured by standard methods. PHEX inhibitors capable of inducing a change in phosphate concentration are said to be hypophosphatemic or phosphaturic. Such compounds are the preferred "hypophosphatemic or phosphaturic PHEX inhibitors" for the purpose of treating hyperphosphatemic patients or for treating patients requiring management of their phosphate levels through other means than normal physiological responses including hyperparathyroidism.

The term "effective amount" is used herein to refer to an amount sufficient to induce significant improvement in the disease or condition to be prevented or treated. Without being so limited, in specific embodiments, it refers to an amount in the range of 0.001 mg/Kg/day to 100 mg/Kg/day.

The "least effective dose" is the minimum dose that is required to induce a significant reduction in serum phosphate, PTH concentration or to normalize other known phosphate active agents including FGF23 (or other phosphatonins). Similarly, "the least significant dose" is the minimum dose required to maintain normal phosphate levels to prevent or reduce an increase in PTH or to normalize other known phosphate active agents including FGF23 (or other phosphatonins). Preferably, the therapy will be initiated with a least effective dose.

The treatment preferably involves the administration of a "phosphaturic PHEX inhibitor" for a period of time sufficient to either achieve a reduction in phosphate or PTH blood concentration, another known phosphate active agent including FGF23 concentration or phosphatonins (hereinafter the "blood parameters") or maintain the blood parameters at a normal level if the reduction was already successfully achieved. Preferably, when reduction of these parameters is sought, the net reduction is about 25% of the difference between the patient value and that of the normal population or, more preferably, at least about 50% of the difference between the patient's value and that of the normal population. The specific period of time sufficient to achieve this reduction in the subject blood parameters may depend on a variety of factors. Such factors include, for example, the specific phosphaturic inhibitor employed, the amount administered, the age and gender of the subject, the specific disorder to be treated, concomitant therapies employed (if any), the general physical health of the subject (including the presence of other disorders), the severity of the disease in the individual, and the nutritional habits of the individual.

As used herein "administering" includes any method which, in sound medical practice, delivers a hypophosphatemic inhibitor of the present invention to a patient in need thereof, in such a manner so as to be effective in achieving a reduction in the blood parameters. The hypophosphatemic PHEX enzyme inhibitor may be administered by any of a variety of known methods of administration, e.g., orally, dermatomucosally (for example, dermally, sublingually, intranasally, and rectally), parenterally (for example, by subcutaneous injection, intramuscular injection, intraarticular injection, intravenous injection), and by inhalation. Thus, specific modes of administration include, for example, oral, transdermal, mucosal, sublingual, intramuscular, intravenous, intraperitoneal, subcutaneous administration, and topical application. A preferred mode for delivering the hypophosphatemic PHEX enzyme inhibitors is orally, for as long and as frequently as medically required. The period and frequency is adjusted after regular measurement of serum phosphate, PTH and vitamin D metabolites.

The present invention also relates to a method of treating hyperphosphatemia Thus, a preferred method of this invention comprising the steps of performing a diagnostic on a human subject for the detection of hyperphosphatemia, including its most frequent manifestations, secondary hyperparathyroidism and renal osteodystrophy as well as other metabolic conditions requiring phosphate management and, upon obtaining a positive result from the diagnostic, administering a phosphaturic PHEX enzyme inhibitor according to the methods of this invention. Suitable diagnostics for the detection of hyperphosphatemia, including its most frequent manifestations, secondary hyperparathyroidism and renal osteodystrophy, are well known in the art. Such methods include the measurement of the blood, serum, plasma or urinary phosphate or the measurement of the blood, serum or plasma PTH as well as other diagnostic chemistries related to phosphate metabolism including FGF23 and phosphatonins.

EXAMPLE 176

Dosage Forms

The PHEX enzyme inhibitors as described herein may be administered in any of a variety of pharmaceutically acceptable compositions. Such compositions comprise an active ingredient and a pharmaceutically acceptable carrier. Accordingly, compositions for administering the PHEX enzyme inhibitor comprise:

(a) from about 1.0 mg to about 1 000.0 mg of a PHEX enzyme inhibitor; and (b) a pharmaceutically acceptable carrier.

Pharmaceutically-acceptable carriers include solid or liquid filler diluents or encapsulating substances, and mixtures thereof, that are suitable for administration to a human or lower animal. The term "compatible", as used herein, means that the components of the pharmaceutical composition are capable of being co-mingled with the hypophosphatemic PHEX enzyme inhibitor, and with each other, in a manner such that there is no interaction, which would substantially reduce the pharmaceutical efficacy of the pharmaceutical composition under ordinary use situations. Pharmaceutically acceptable carriers must, of course, be of sufficiently high purity and sufficiently low toxicity to render them suitable for administration to the humans or lower animals being treated.

Some examples of the substances which can serve as pharmaceutical carriers are: sugars, such as lactose, glucose and sucrose; starches, such as corn starch and potato starch; cellulose and its derivatives, such-as sodium carboxymethylcellulose, ethylcellulose, cellulose acetate; powdered tragacanth; malt; gelatin; talc; stearic acid; magnesium stearate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; phosphate buffer solutions; wetting agents and lubricants such as sodium lauryl sulfate; coloring agents; flavoring agents; and preservatives. Other compatible pharmaceutical additives and hypophosphatemic PHEX enzyme inhibitor may be included in the pharmaceutically acceptable carrier for use in the compositions of the present invention.

The choice of a pharmaceutically-acceptable carrier to be used in conjunction with the active substance is determined by the way the active substance is to be administered. If the active is to be injected, the preferred pharmaceutical carrier is sterile water, physiological saline, or mixtures thereof. The pH of such parenteral composition is preferably adjusted to about 7.4. Suitable pharmaceutically acceptable carriers for topical, anal or vaginal applications include those known in the art for use in creams, gels, tapes, patches, and similar topical delivery means. The active could also be administered intra-nasally or pulmonary with a suitable carrier as the conditions will require.

The pharmaceutically-acceptable carrier employed in conjunction with the phosphaturic PHEX enzyme inhibitor is used at a concentration sufficient to provide a practical size to dosage relationship. The pharmaceutically-acceptable carriers, in total, may comprise from about 0.1% to about 99.9% by weight of the pharmaceutical compositions of the present invention, preferably from about 5% to about 80%, and most preferably from about 10% to about 50%.

As indicated, the preferred method of administering a phosphaturic PHEX enzyme inhibitor of the present invention is dependent upon the class of active being administered. For the phosphaturic PHEX inhibitors, the preferred method of administration is orally, in a unit-dosage form (i.e., a dosage form containing an amount of active suitable for administration in one single dose, according to sound medical practice).

Preferred unit dosage forms include tablets, capsules, suspensions, and solutions, comprising a safe and effective amount of active. Pharmaceutically-acceptable carriers suitable for the preparation of unit dosage forms for oral administration are well known in the art. Their selection will depend on secondary considerations like taste, cost, shelf stability, which are not critical for the purposes of the present invention, and can be made without difficulty by a person skilled in the art. Preferably, oral unit dosage forms of the PHEX enzyme inhibitor comprise from about 1.0 mg to about 1000 mg of the inhibitor.

Although the present invention has been described hereinabove by way of preferred embodiments thereof, it can be modified without departing from the spirit and nature of the subject invention as defined in the appended claims.

REFERENCES

The following references, to the extent that they provide exemplary procedural or other details supplementary to those set forth herein, are specifically incorporated herein by reference.

U.S. Pat. No. 4,337,201
U.S. Pat. No. 5,362,727
U.S. Pat. No. 5,380,921
U.S. Pat. No. 4,168,267
ADHR Consortium, *Nat. Genetics*, 26:345–348, 2000.
Atherton and Sheppard, In: *The Peptides*, Udenfriend and Meienhofer (Eds.), 9:1, Academic Press, NY, 1987.
Beck et al., *J. Clin. Invest.*, 99:1200–1209, 1997.
Balkenhohl et al., *Angew. Chem. Int. Ed. Engl.*, 35:2288–2337, 1996.
Bellows et al., *Calcif. Tissue Int.*, 38:143–154, 1986.
Du et al., *Genomics*, 36:22–28, 1996.
Ecarot et al., *J. Bone. Miner. Res.*, 7:215–220, 1992.
Econs and Drezner, *N. Engl. J. Med.*, 330:1679–1681, 1994.
Furka. In: *Combinatorial Peptide and Nonpeptide Libraries*, Jung (Ed.), 4:111–137, VCH Verlagsgesellschaft, Weinheim, 1996.
Greene and Wuts, In: *Protective Groups in Organic Synthesis*, John Wiley & Sons, Inc., NY, 1999.
Grieff et al., *Biochem. Biophys. Res. Commun.*, 231:635–639, 1997.
Guo and Quarles, *J. Bone Miner. Res.*, 12:1009–1017, 1997.
Hermkens et al., *Tetrahedron*, 52:4527–4554, 1996.
Ikeuchi et al., *J. Biomed. Mater Res.*, 60:61–69, 2002.
Jan de Beur et al., *J. Bone Miner. Res.*, 17:1102–1110, 2002.
Jonsson et al., ASBMR 24th Annual Meeting in San Antonio, Tex., USA, Pres. # 1139, 2002.
Lajeunesse et al., *Kidney Int.*, 50:1531–1538, 1996.
Lipman et al., *J. Biol. Chem.*, 273:13729–13737, 1998.
Nesbitt et al., *J. Bone Miner. Res.*, 14:2027–2035, 1999. PCT Appln. WO 00/50580
Rivero et al., In: *A Practical Guide to Combinatorial Chemistry*, Czarnik (Eds.), 10:281–307, American Chem. Soc. Pub., Washington D.C., 1997.
Roques et al., *Pharmacological Reviews*, 45:87–146, 1993.
Rowe et al., *Genomics*, 67:54–68, 2000.
Ruchon et al., *J. Histochem. Cytochem.*, 46:1–10, 1998.
Ruchon et al., *J. Bone Miner. Res.*, 15:1440–1450, 2000.
Schiavi and Moe, *Curr. Opin. Nephrol. Hypertens.*, 11:423–430, 2002.
Shimada et al., *Proc. Natl. Acad. Sci. USA*, 98:6500–6505, 2001.
Strom et al., *Hum. Mol. Genet.*, 6:165–171, 1997.
Tenenhouse, *Nephrol. Dial. Transplant.*, 14:333–341, 1999.
Tenenhouse and Econs, In: *The Metabolic and Molecular Bases of Inherited Disease. Scriver et al. (Eds.)*, 197:5039–5067, McGraw Hill Book Co., NY, 2001.
Terrett et al., *Tetrahedron*, 51:8135–8173, 1995.
The HYP Consortium, *Nat. Genet.*, 11:130–136, 1995.
Thompson and Ellman, *Chem. Rev.*, 96:555–600, 1996.
Turner and Tanzawa, *FASEB J.*, 11:355–364, 1997.
Vehof et al., *Plast. Reconstr. Surg.*, 108:434–443, 2001.
Vu et al., et al., *J. Histochem. Cytochem.*, 47:323–336, 1999.
Whittaker et al., *Chem. Rev.*, 99:2735–2776, 1999.
Yoshida et al., *J. Dent. Res.*, 78:217–220, 1999.

What is claimed:

1. A compound of Formula (I), or a pharmaceutically acceptable salt thereof:

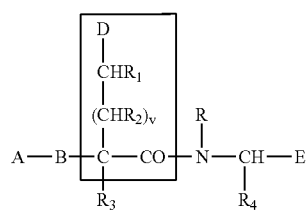

(I)

wherein
A is a zinc ligand or zinc ligand bearing moiety selected from the group consisting of:

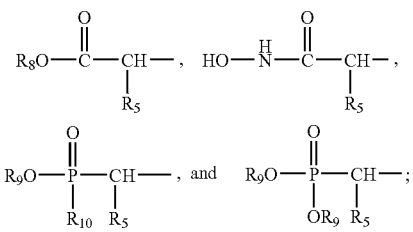

B is absent:
R is hydrogen or lower alkyl;
$R_1$ is hydrogen or lower alkyl;
$R_2$ is hydrogen, or lower alkyl;
$R_3$ is hydrogen or lower alkyl;

$R_4$ is lower alkyl, substituted lower alkyl, cycloalkyl-$(CH_2)_w$—, aryl-$(CH_2)_w$—, substituted aryl —$(CH_2)_w$— or heteroaryl-$(CH_2)_w$—;

$R_5$ is hydrogen, lower alkyl, substituted lower alkyl, cycloalkyl-$(CH_2)_x$—, aryl-$(CH_2)_x$—, substituted aryl-$(CH_2)_x$—, or heteroaryl-$(CH_2)_x$—;

$R_8$ and $R_9$ are independently selected from the group consisting of hydrogen, alkyl, substituted alkyl, aryl-$(CH_2)_y$—, substituted aryl-$(CH_2)_y$—, heteroaryl-$(CH_2)_y$—,

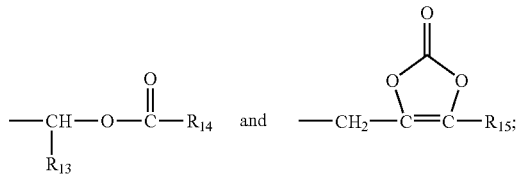

$R_{10}$ is alkyl, substituted alkyl, cycloalkyl-$(CH_2)_y$,, aryl-$(CH_2)_y$—, substituted aryl-$(CH_2)_y$— or heteroaryl-$(CH_2)_y$—;

$R_{13}$ is hydrogen, lower alkyl, cycloalkyl or phenyl;

$R_{14}$ is hydrogen, lower alkyl, lower alkoxy or phenyl;

$R_{15}$ is lower alkyl or aryl-$(CH_2)_y$—;

D is —COOH,

E is hydrogen, —COOH, —CONH$_2$, —CONH(lower alkyl), —CON(lower alkyl)$_2$, —CONH—$(CH_2)_z$-aryl, —CON(—$(CH_2)_z$-aryl)$_2$, —CO-amino acid, —CH$_2$COOH, CH$_2$OH, —CH$_2$CH$_2$OH, or —COOR$_{16}$;

$R_{16}$ is selected from the group consisting of hydrogen, alkyl, substituted alkyl, aryl-$(CH_2)_y$—, substituted aryl-$(CH_2)_y$—, heteroaryl-$(CH_2)_y$—,

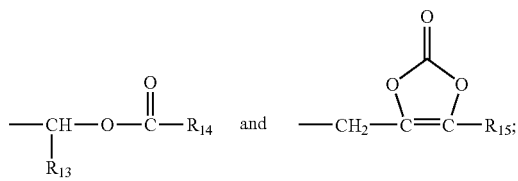

C is carbon;
H is hydrogen;
O is oxygen;
N is nitrogen;
S is sulfur;
P is phosphorus;
v is zero;
w is zero or an integer ranging from 1 to 4;
x is an integer ranging from 1 to 4;
y is zero or an integer ranging from 1 to 6; and
z is zero, one, two, or three.

2. The compound of claim 1, wherein $R_1$ and $R_3$, when v=0, are connected together to form an alkylene bridge of 3 carbon atoms representing with the carbon atoms to which they are attached a cyclopentane ring.

3. The compound of claim 1, wherein $R_1$ and $R_3$, when v=0, are connected together to form an alkylene bridge of 4 carbon atoms representing with the carbon atoms to which they are attached a cyclohexane ring.

4. The compound of claim 1, wherein R and $R_4$ are connected together to form an alkylene bridge of 3 carbon atoms representing with the nitrogen and carbon atoms to which they are attached a pyrrolidine ring.

5. The compound of claim 1, wherein R and $R_4$ are connected together to form an alkylene bridge of 4 carbon atoms representing with the nitrogen and carbon atoms to which they are attached a piperidine ring.

6. The compound of claim 1, wherein the compound is further defined as: 3-(2-Biphenyl-4-yl-ethylcarbamoyl)-4-hydroxycarbamoyl-butyric acid; 3-[2-(4'-Cyano-biphenyl-4-yl)-ethylcarbamoyl]-4-hydroxycarbamoyl-butyric acid; 4-Hydroxycarbamoyl-3-[2-(4-pyridin-2-yl-phenyl)-ethylcarbamoyl]-butyric acid; 4-Hydroxycarbamoyl-3-(4-phenyl-butylcarbamoyl)-butyric acid; 4-Hydroxycarbamoyl-3-(2-phenoxy-ethylcarbamoyl)-butyric acid; 3-[2-(4'-Hydroxy-biphenyl-4-yl)-ethylcarbamoyl]-4-hydroxycarbamoyl-butyric acid; 3-(2,2-Diphenyl-ethylcarbamoyl)-4-hydroxycarbamoyl-butyric acid; 3-[2-(4'-Dimethylamino-biphenyl-4-yl)-ethylcarbamoyl]-4-hydroxycarbamoyl-butyric acid; 4-Hydroxycarbamoyl-3-(5-hydroxy-pentylcarbamoyl)-butyric acid; 3-[(Biphenyl-4-ylmethyl)-carbamoyl]-4-hydroxycarbamoyl-butyric acid; N-[1-carboxy-2-(1H-indol-3-yl)-ethyl]-3-(3-phenyl-1-phosphono-propylamino)-succinic acid; or 3-(2-Naphthalen-2-yl-ethylcarbamoyl)-pentanedioic acid.

7. The compound of claim 6, wherein the compound is 3-(2-Biphenyl-4-yl-ethylcarbamoyl)-4-hydroxycarbamoyl-butyric acid.

8. A pharmaceutical composition comprising a therapeutically effective amount of a compound of claim 1 and a physiologically acceptable carrier or excipient.

9. The pharmaceutical composition of claim 8, wherein the compound is further defined as: 3-(2-Biphenyl-4-yl-ethylcarbamoyl)-4-hydroxycarbamoyl-butyric acid; 3-[2-(4'-Cyano-biphenyl-4-yl)-ethylcarbamoyl]-4-hydroxycarbamoyl-butyric acid; 4-Hydroxycarbamoyl-3-[2-(4-pyridin-2-yl-phenyl)-ethylcarbamoyl]-butyric acid; 4-Hydroxycarbamoyl-3-(4-phenyl-butylcarbamoyl)-butyric acid; 4-Hydroxycarbamoyl-3-(2-phenoxy-ethylcarbamoyl)-butyric acid; 3-[2-(4'-Hydroxy-biphenyl-4-yl)-ethylcarbamoyl]-4-hydroxycarbamoyl-butyric acid; 3-(2,2-Diphenyl-ethylcarbamoyl)-4-hydroxycarbamoyl-butyric acid; 3-[2-(4'-Dimethylamino-biphenyl-4-yl)-ethylcarbamoyl]-4-hydroxycarbamoyl-butyric acid; 4-Hydroxycarbamoyl-3-(5-hydroxy-pentylcarbamoyl)-butyric acid; 3-[(Biphenyl-4-ylmethyl)-carbamoyl]-4-hydroxycarbamoyl-butyric acid; N-[1-carboxy-2-(1H-indol-3-yl)-ethyl]-3-(3-phenyl-1-phosphono-propylamino)-succinic acid; or 3-(2-Naphthalen-2-yl-ethylcarbamoyl)-pentanedioic acid.

10. The pharmaceutical composition of claim 8, wherein the compound is 3-(2-Biphenyl-4-yl-ethylcarbamoyl)-4-hydroxycarbamoyl-butyric acid.

11. The compound of claim 1, wherein A is

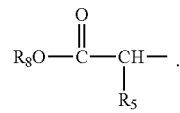

12. The compound of claim 1, wherein A is

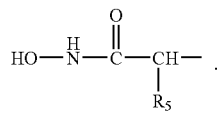

13. The compound of claim 1, wherein A is

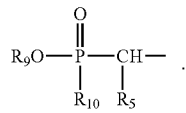

14. The compound of claim 1, wherein A is

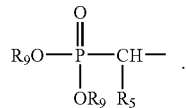

15. The compound of claim 1 having the formula:

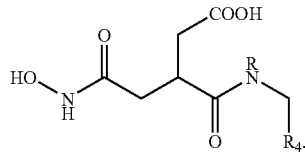

16. The pharmaceutical composition of claim 9, wherein the compound is further defined as 3-[2-(4'-Cyano-biphenyl-4-yl)-ethylcarbamoyl]-4-hydroxycarbamoyl-butyric acid.

17. The pharmaceutical composition of claim 9, wherein the compound is further defined as 4-Hydroxycarbamoyl-3-[2-(4-pyridin-2-yl-phenyl)-ethylcarbamoyl]-butyric acid.

18. The pharmaceutical composition of claim 9, wherein the compound is further defined as 4-Hydroxycarbamoyl-3-(4-phenyl-butylcarbamoyl)-butyric acid.

19. The pharmaceutical composition of claim 9, wherein the compound is further defined as 4-Hydroxycarbamoyl-3-(2-phenoxy-ethylcarbamoyl)-butyric acid.

20. The pharmaceutical composition of claim 9, wherein the compound is further defined as 3-[2-(4'-Hydroxy-biphenyl-4-yl)-ethylcarbamoyl]-4-hydroxycarbamoyl-butyric acid.

21. The pharmaceutical composition of claim 9, wherein the compound is further defined as 3-(2,2-Diphenyl-ethylcarbamoyl)-4-hydroxycarbamoyl-butyric acid.

22. The pharmaceutical composition of claim 9, wherein the compound is further defined as 3-[2-(4'-Dimethylamino-biphenyl-4-yl)-ethylcarbamoyl]-4-hydroxycarbamoyl-butyric acid.

23. The pharmaceutical composition of claim 9, wherein the compound is further defined as 4-Hydroxycarbamoyl-3-(5-hydroxy-pentylcarbamoyl)-butyric acid.

24. The pharmaceutical composition of claim 9, wherein the compound is further defined as 3-[(Biphenyl-4-ylmethyl)-carbamoyl]-4-hydroxycarbamoyl-butyric acid.

25. The pharmaceutical composition of claim 9, wherein the compound is further defined as N-[1-carboxy-2-(1H-indol-3-yl)-ethyl]-3-(3-phenyl-1-phosphono-propylamino)-succinic acid.

26. The pharmaceutical composition of claim 9, wherein the compound is further defined as 3-(2-Naphthalen-2-yl-ethylcarbamoyl)-pentanedioic acid.

* * * * *

UNITED STATES PATENT AND TRADEMARK OFFICE
CERTIFICATE OF CORRECTION

| | | |
|---|---|---|
| PATENT NO. | : 7,105,539 B2 | Page 1 of 1 |
| APPLICATION NO. | : 10/727119 | |
| DATED | : September 12, 2006 | |
| INVENTOR(S) | : Gravel et al. | |

It is certified that error appears in the above-identified patent and that said Letters Patent is hereby corrected as shown below:

Column 88, lines 57-58, delete "3-(2-Biphenyl-4-yl-ethylcarbamoyl)-4-hydroxycarbamoyl-butvric" and insert --3-(2-Biphenyl-4-yl-ethylcarbamoyl)-4-hydroxycarbamoyl-butyric-- therefor.

Signed and Sealed this

Twenty-sixth Day of December, 2006

JON W. DUDAS
*Director of the United States Patent and Trademark Office*